US012758653B2

(12) United States Patent
Kohn et al.

(10) Patent No.: US 12,758,653 B2
(45) Date of Patent: Oct. 13, 2026

(54) LENTIVIRAL VECTORS IN HEMATOPOIETIC STEM CELLS TO TREAT X-LINKED CHRONIC GRANULOMATOUS DISEASE

(71) Applicant: The Regents of the University of California, Oakland, CA (US)

(72) Inventors: Donald B. Kohn, Tarzana, CA (US); Ryan L. Wong, Los Angeles, CA (US); Roger Paul Hollis, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1156 days.

(21) Appl. No.: 17/775,857

(22) PCT Filed: Nov. 12, 2020

(86) PCT No.: PCT/US2020/060263
§ 371 (c)(1),
(2) Date: May 10, 2022

(87) PCT Pub. No.: WO2021/097109
PCT Pub. Date: May 20, 2021

(65) Prior Publication Data

US 2022/0378937 A1 Dec. 1, 2022

Related U.S. Application Data

(60) Provisional application No. 62/934,352, filed on Nov. 12, 2019.

(51) Int. Cl.

| | |
|---|---|
| ***A61K 48/00*** | (2006.01) |
| ***A61P 37/00*** | (2006.01) |
| ***C12N 9/02*** | (2006.01) |
| ***C12N 15/86*** | (2006.01) |

(52) U.S. Cl.
CPC ............ *A61K 48/005* (2013.01); *A61P 37/00* (2018.01); *C12N 9/0036* (2013.01); *C12N 15/86* (2013.01); *A61K 48/0066* (2013.01); *C12N 2740/16043* (2013.01); *C12N 2800/22* (2013.01); *C12N 2830/008* (2013.01); *C12N 2830/48* (2013.01); *C12Y 106/03001* (2013.01)

(58) Field of Classification Search
CPC .......... C12N 15/86; C12N 2740/16043; C12N 2800/22; A61K 48/0066
See application file for complete search history.

(56) References Cited

U.S. PATENT DOCUMENTS

| | | | |
|---|---|---|---|
| 4,522,811 | A | 6/1985 | Eppstein et al. |
| 5,686,279 | A | 11/1997 | Finer et al. |
| 5,994,136 | A | 11/1999 | Naldini et al. |
| 6,136,597 | A | 10/2000 | Hope et al. |
| 2003/0039636 | A1 | 2/2003 | Leboulch et al. |
| 2007/0054278 | A1 | 3/2007 | Cargill |
| 2007/0161031 | A1 | 7/2007 | Trinklein et al. |
| 2007/0271630 | A1 | 11/2007 | Boukharov et al. |
| 2017/0067079 | A1 | 3/2017 | Trono et al. |
| 2019/0201449 | A1 | 7/2019 | Li et al. |

FOREIGN PATENT DOCUMENTS

| | | |
|---|---|---|
| WO | WO-2009012959 A1 | 1/2009 |
| WO | WO 2010/125471 | 11/2010 |
| WO | WO 2017/191274 | 11/2017 |

OTHER PUBLICATIONS

Rae J, Newburger PE, Dinauer MC, Noack D, Hopkins PJ, Kuruto R, Curnutte JT. X-Linked chronic granulomatous disease: mutations in the CYBB gene encoding the gp91-phox component of respiratory-burst oxidase. Am J Hum Genet. Jun. 1998;62(6): 1320-31. doi: 10.1086/301874. PMID: 9585602; PMCID: PMC1377153. (Year: 1998).*

Grote et al., "JCat: a novel tool to adapt codon usage of a target gene to its potential expression host", Nucleic Acids Research, 2005, 33(suppl 2): W526-W531.

Zufferey et al., "Self-Inactivating Lentivirus Vector for Safe and Efficient In Vivo Gene Delivery", J. Virol., Dec. 1998; 72(12): 9873-9880.

Dull et al., "A Third-Generation Lentivirus Vector with a Conditional Packaging System", J. Virol., Nov. 1998; 72(11): 8463-8471.

Burgess-Beusse et al., "The insulation of genes from external enhancers and silencing chromatin", Proc. Natl. Acad. Sci. USA, Dec. 2002; 99(suppl 4): 16433-16437.

Zhan et al., "Insulator: from chromatin domain boundary to gene regulation", Hum Genet (2001) 109 :471-478.

Prioleau et al., "An insulator element and condensed chromatin region separate the chicken β-globin locus from an independently regulated erythroid-specific folate receptor gene", EMBO J., (1999) 18(14): 4035-4048.

Chung et al., "A 5' Element of the Chicken p-Globin Domain Serves as an Insulator in Human Erythroid Cells and Protects against Position Effect in *Drosophila*", Cell, Aug. 13, 1993; 74: 505-514.

Pikaart et al., "Loss of transcriptional activity of a transgene is accompanied by DNA methylation and histone deacetylation and is prevented by insulators", Genes Dev. (1998) 12: 2852-2862.

Wang et al., "Ligand-inducible and liver-specific target gene expression in transgenic mice", Nat. Biotechnol., Mar. 1997; 15(3): 239-243.

(Continued)

*Primary Examiner* — Fereydoun G Sajjadi
*Assistant Examiner* — Qinhua Gu
(74) *Attorney, Agent, or Firm* — Mark S. Cohen; PEARL COHEN LLP

(57) ABSTRACT

Described herein is a lentiviral vector (LV) for the treatment of X-linked chronic granulomatous disease (X-CGD). The vector comprises an expression cassette comprising a nucleic acid construct comprising a CYBB promoter or effective fragment thereof, and a nucleic acid that encodes gp91$^{phox}$ operably linked to the CYBB promoter or promoter fragment thereof.

12 Claims, 34 Drawing Sheets

Specification includes a Sequence Listing.

(56) References Cited

OTHER PUBLICATIONS

Taboit-Dameron et al., "Association of the 5' HS4 sequence of the chicken β-globin locus control region with human EF1α gene promoter induces ubiquitous and high expression of human CD55 and CD59 cDNAs in transgenic rabbits", Transgenic Res., (1999) 8: 223-235.
Chung et al., "Characterization of the chicken β-globin insulator", Proc. Natl. Acad. Sci., USA, Jan. 1997; 94: 575-580.
Bell et al., "The Protein CTCF Is Required for the Enhancer Blocking Activity of Vertebrate Insulators", Cell, Aug. 1999; 98: 387-396.
Ramezani et al., "Combinatorial Incorporation of Enhancer-Blocking Components of the Chicken β-Globin 5'HS4 and Human T-Cell Receptor α/δ BEAD-1 Insulators in Self-Inactivating Retroviral Vectors Reduces Their Genotoxic Potential", Stem Cell (2008) 26: 3257-3266.
Chen et al., "Gene therapy for brain tumors: Regression of experimental gliomas by adenovirus-mediated gene transfer in vivo", Proc. Natl. Acad. Sci. USA, Apr. 1994; 91: 3054-3057.
Barde et al., "Lineage- and stage-restricted lentiviral vectors for the gene therapy of chronic granulomatous disease", Gene Therapy (2011) 18:1087-1097.
Brendel, C. et al., "Non-Clinical Efficacy and Safety Studies on G1XCGD, a Lentiviral Vector for Ex Vivo Gene Therapy of X-Linked Chronic Granulomatous Disease", Human Gene Therapy Clinical Development, 2018, vol. 29, No. 2, pp. 69-79.
International Preliminary Report on Patentability dated May 27, 2022, in PCT Application No. PCT/US2020/060263.
International Search Report and Written Opinion dated Mar. 2, 2021, in PCT Application No. PCT/US2020/060263.
Kohn, D.B. et al., "Gene Therapy for X-Linked Chronic Granulomatous Disease", American Society of Gene & Cell Therapy, 2018, No. 340, 1 page.
Santilli, G. et al., "Biochemical Correction of X-CGD by a Novel Chimeric Promoter Regulating High Levels of Transgene Expression in Myeloid Cells", The American Society of Gene & Cell Therapy, Molecular Therapy, Jan. 2011, vol. 19, No. 1, pp. 122-132.
Stein, S. et al., "Genomic instability and myelodysplasia with monosomy 7 consequent to EVI1 activation after gene therapy for chronic granulomatous disease", Nature Medicine, Feb. 2010, vol. 16, No. 2, pp. 198-204.
Partial Supplementary European Search Report, dated Nov. 24, 2023, from corresponding European Patent Application No. 20886706.9.
Extended European Search Report, dated Feb. 14, 2024, from corresponding European Patent Application No. 20886706.9.
Farinelli et al., "Lentiviral Vector Gene Therapy Protects XCGD Mice from Acute *Staphylococcus aureus* Pneumonia and Inflammatory Response", Molecular Therapy, Oct. 2016, 24(10): 1873-1880.
Chiriaco et al., "Dual-regulated Lentiviral Vector for Gene Therapy of X-linked Chronic Granulomatosis", Molecular Therapy, Aug. 2014, 22(8): 1472-1483.

* cited by examiner

*B*

*A*

*B*
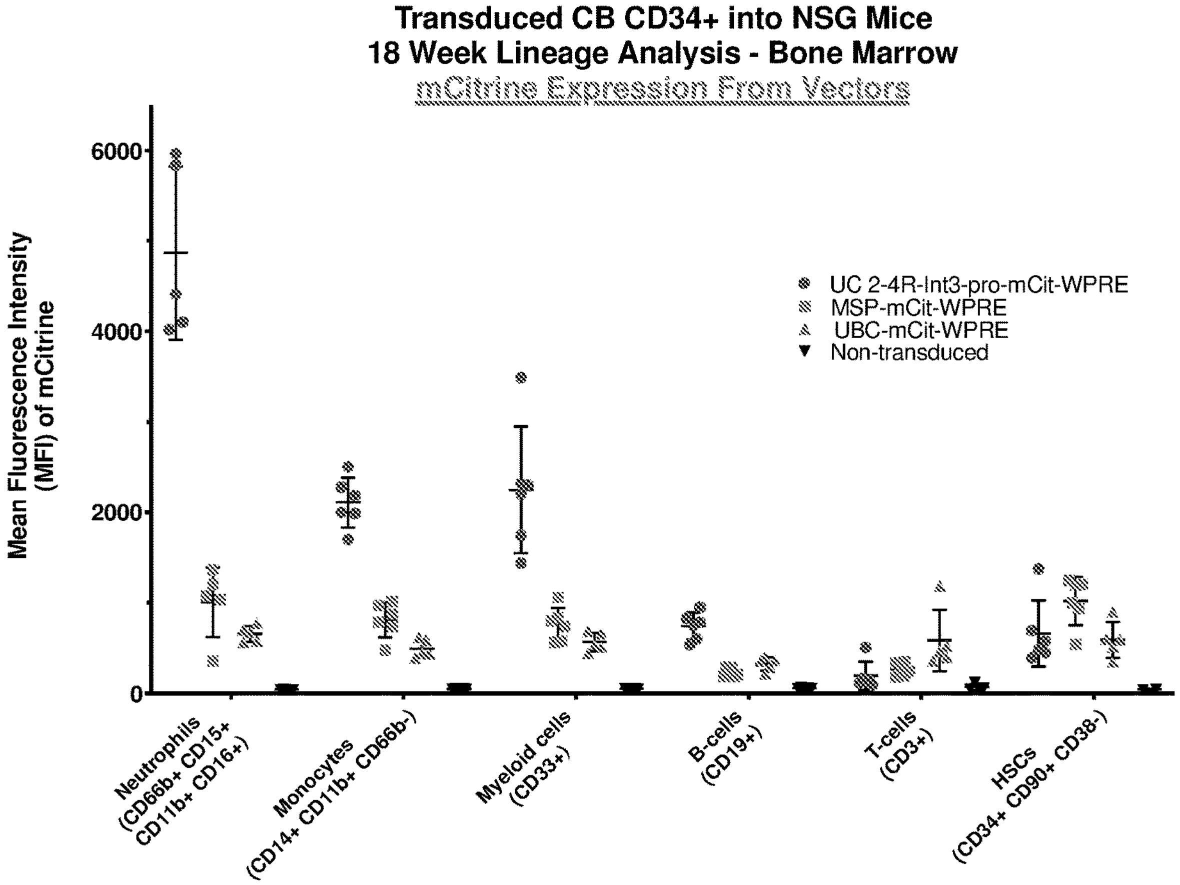
*Fig. 22, cont'd.*

LENTIVIRAL VECTORS IN HEMATOPOIETIC STEM CELLS TO TREAT X-LINKED CHRONIC GRANULOMATOUS DISEASE

CROSS-REFERENCE TO RELATED APPLICATIONS

This application is a U.S. 371 National Phase of International Application No. PCT/US2020/060263, filed on Nov. 12, 2020, which claims priority to and benefit of U.S. Ser. No. 62/934,352, filed on Nov. 12, 2019, both of which is are incorporated herein by reference in their entirety for all purposes.

STATEMENT OF GOVERNMENTAL SUPPORT

[Not Applicable]

INCORPORATION BY REFERENCE OF SEQUENCE LISTING PROVIDED AS A TEXT FILE

A Sequence Listing is provided herewith as a text file, "UCLA-P218P_ST25.txt" created on Nov. 11, 2019 and having a size of 46.4 kb. The contents of the text file are incorporated by reference herein in their entirety.

BACKGROUND

X-linked chronic granulomatous disease (X-CGD) is a primary immune deficiency caused by mutations in the CYBB gene which encodes for a vital subunit of the phagocyte NADPH Oxidase (PHOX) complex. A defective PHOX complex results in the inability of the phagocytic cells of the immune system to properly eliminate infections.

Patients are therefore highly susceptible and suffer from recurrent, life-threatening bacterial and fungal infections. In typical subjects, the immune system attempts to wall off the infection but is unable to eliminate it, leading to the characteristic formation of granulomas that can result in damage to those tissues. The features of chronic granulomatous disease usually first appear in childhood, although some individuals do not show symptoms until later in life.

People with chronic granulomatous disease typically have at least one serious bacterial or fungal infection every 3 to 4 years. The lungs are the most frequent area of infection and pneumonia is a common feature of this condition. Individuals with chronic granulomatous disease may develop a type of fungal pneumonia, called mulch pneumonitis, which causes fever and shortness of breath after exposure to decaying organic materials such as mulch, hay, or dead leaves. Exposure to these organic materials and the numerous fungi involved in their decomposition causes people with chronic granulomatous disease to develop fungal infections in their lungs. Other common areas of infection in people with chronic granulomatous disease include the skin, liver, and lymph nodes.

Inflammation can occur in many different areas of the body in people with chronic granulomatous disease. Most commonly, granulomas occur in the gastrointestinal tract and the genitourinary tract. In many cases the intestinal wall is inflamed, causing a form of inflammatory bowel disease that varies in severity but can lead to stomach pain, diarrhea, bloody stool, nausea, and vomiting. Other common areas of inflammation in people with chronic granulomatous disease include the stomach, colon, and rectum, as well as the mouth, throat, and skin. Additionally, granulomas within the gastrointestinal tract can lead to tissue breakdown and pus production (abscesses). Inflammation in the stomach can prevent food from passing through to the intestines (gastric outlet obstruction), leading to an inability to digest food. These digestive problems cause vomiting after eating and weight loss. In the genitourinary tract, inflammation can occur in the kidneys and bladder. Inflammation of the lymph nodes (lymphadenitis) and bone marrow (osteomyelitis), which both produce immune cells, can lead to further impairment of the immune system.

Rarely, people with chronic granulomatous disease develop autoimmune disorders, which occur when the immune system malfunctions and attacks the body's own tissues and organs.

Repeated episodes of infection and inflammation reduce the life expectancy of individuals with chronic granulomatous disease.

The PHOX complex is made of five different subunits encoded by five different genes. These are $gp91^{phox}$ encoded by CYBB, $p22^{phox}$ encoded by CYBA, $p47^{phox}$ encoded by NCF1, $p67^{phox}$ encoded by NCF2, and $p40^{phox}$ encoded by NCF4. Most common mutations are in the CYBB gene encoding for $gp91^{phox}$ which accounts for ~56%-70% of all cases of CGD. The condition is X-linked and accordingly primarily affects males.

The disease was initially terms "fatal granulomatous disease of childhood" and without treatment patient rarely lived past their first decade of life. Current standard of care utilizes routine prophylactic antibacterial and antifungal therapy and results in a mean age of survival around 30-40 years. These treatments do not provide a cure for the disease.

One potential curative therapy is an allogeneic hematopoietic stem cell transplantation from an HLA matched donor. However, this is not a viable option for many patients due to the unavailability of a suitable matched donor.

An alternative curative therapy is an autologous hematopoietic stem cell (HSC) transplantation with ex vivo gene therapy. In this approach, patients act as their own donor, eliminating the risk of immunological complications. The patient's own blood HSCs are harvested and are genetically engineered ex-vivo to introduce a functional copy of gene of interest, and gene modified cells are reinfused.

Previous viral-based therapies utilized a γ-retroviral vector driven by the spleen focus-forming virus (SFFV) promoter. This provided a promising clinical benefit. However, 2/2 patients developed myelodysplasia due to insertional oncogenesis. A current safer SIN lentiviral vector (pChim-CYBB; aka MSP-Gp91phox-WPRE) employs a chimeric "myeloid-specific promoter" (MSP) and initial results from current clinical trials indicate potential clinical benefits. However, the pChim-CYBB construct fails to recapitulate wildtype levels of expression and regulation of $Gp91^{phox}$. Thus, for example, patient's neutrophils post gene therapy under-express $Gp91^{phox}$ compared to normal heathy donor cells.

SUMMARY

Described herein is the development of novel lentiviral vector(s) (LVs) for the treatment of X-CGD. The vectors described herein show better (higher) expression than the current lentiviral vector. Additionally, the vectors described herein possesses strict lineage and stage specific expression that mimics the expression pattern of the native CYBB gene. This is in contrast to the MSP construct(s) that have off-target expression and fail to recapitulate the lineage specific expression pattern of the native CYBB gene.

Accordingly, various embodiments contemplated herein may include, but need not be limited to, one or more of the following:

Embodiment 1: A recombinant lentiviral vector (LV) for the treatment of chronic granulomatous disease, said vector comprising:

an expression cassette comprising a nucleic acid construct comprising:

a CYBB promoter or effective fragment thereof; and a nucleic acid that encodes gp91$^{phox}$ operably linked to said CYBB promoter or promoter fragment.

Embodiment 2: The vector of embodiment 1, wherein said CYBB promoter or effective fragment thereof comprises a full-length endogenous CYBB promoter (SEQ ID NO:1).

Embodiment 3: The vector of embodiment 1, wherein said CYBB promoter comprises an effective fragment of a CYBB promoter where said fragment comprises or consists of the minimal CYBB promoter (core) (SEQ ID NO: 2).

Embodiment 4: The vector of embodiment 3, wherein said CYBB promoter comprises an effective fragment of a CYBB promoter where said fragment consists of the minimal CYBB promoter (core) (SEQ ID NO: 2).

Embodiment 5: The vector of embodiment 1, wherein said CYBB promoter comprises an effective fragment of a CYBB promoter where said fragment comprises or consists of the minimal CYBB promoter (ultra core) (SEQ ID NO:3).

Embodiment 6: The vector of embodiment 5, wherein said CYBB promoter consists of an effective fragment of the CYBB promoter whose sequence consists of the minimal CYBB promoter (ultra core) (SEQ ID NO:3).

Embodiment 7: The vector according to any one of embodiments 1-6, wherein said expression cassette comprises an enhancer element 2 (SEQ ID NO:4) or an effective fragment thereof.

Embodiment 8: The vector of embodiment 7, wherein said expression cassette comprises an effective fragment of enhancer element 2 wherein said fragment comprises or consists of enhancer element 2 core (SEQ ID NO:5).

Embodiment 9: The vector of embodiment 8, wherein the sequence of said effective fragment of enhancer element 2 consists of the sequence of enhancer element 2 core (SEQ ID NO:5).

Embodiment 10: The vector of embodiment 7, wherein said expression cassette comprises an effective fragment of enhancer element 2 wherein said fragment comprises or consists of enhancer element 2 ultra core (SEQ ID NO:6).

Embodiment 11: The vector of embodiment 10, wherein the sequence of said effective fragment of enhancer element 2 consists of the sequence of enhancer element 2 ultra core (SEQ ID NO:6).

Embodiment 12: The vector according to any one of embodiments 1-11, wherein said expression cassette further comprises a RELA TF binding site or an effective fragment thereof.

Embodiment 13: The vector of embodiment 12, wherein said RELA TF binding site comprises or consists of the nucleic acid sequence of SEQ ID NO:7).

Embodiment 14: The vector according to any one of embodiments 1-11, wherein said expression cassette comprises enhancer element 4 or an effective fragment thereof.

Embodiment 15: The vector of embodiment 14, wherein said expression cassette comprises an enhancer element 4R or an effective fragment thereof.

Embodiment 16: The vector of embodiment 15, wherein said expression cassette comprises an effective fragment of enhancer element 4R where the nucleic acid sequence of said fragment comprises or consists of the nucleic acid sequence of enhancer element 4R core (SEQ ID NO:10).

Embodiment 17: The vector of embodiment 15, wherein said expression cassette comprises an effective fragment of enhancer element 4R where the nucleic acid sequence of said fragment comprises or consists of the nucleic acid sequence of enhancer element 4R ultra core (SEQ ID NO:11).

Embodiment 18: The vector of embodiment 16, wherein said expression cassette comprises an effective fragment of enhancer element 4R where the nucleic acid sequence of said fragment consists of the nucleic acid sequence of enhancer element 4R ultra core (SEQ ID NO:11).

Embodiment 19: The vector according to any one of embodiments 1-18, wherein said expression cassette comprises an enhancer element 4L or an effective fragment thereof.

Embodiment 20: The vector of embodiment 19, wherein said expression cassette comprises an effective fragment of enhancer element 4L where said fragment comprises or consists of the sequence of 4L core sequence (SEQ ID NO:13).

Embodiment 21: The vector according to any one of embodiments 1-20, wherein said expression cassette comprises an intron enhancer element 3 (SEQ ID NO:14) or an effective fragment thereof.

Embodiment 22: The vector of embodiment 21, wherein said expression cassette comprise an intron enhancer element 3 middle fragment comprising or consisting of the nucleic acid sequence of SEQ ID NO:15.

Embodiment 23: The vector according to any one of embodiments 21-22, wherein said expression cassette comprises an intron enhancer element 3 right fragment comprising or consisting of the nucleic acid sequence of SEQ ID NO: 16.

Embodiment 24: The vector according to any one of embodiments 1-23, wherein said nucleic acid that encodes a nucleic acid that encodes gp91$^{phox}$ is a CYBB cDNA or a codon-optimized CYBB.

Embodiment 25: The vector of embodiment 24, wherein said nucleic acid that encodes gp91$^{phox}$ is a CYBB cDNA (SEQ ID NO:17).

Embodiment 26: The vector of embodiment 24, wherein said nucleic acid that encodes gp91$^{phox}$ is a codon optimized CYBB.

Embodiment 27: The vector of embodiment 26, wherein the sequence of said nucleic acid that encodes gp91$^{phox}$ is a codon optimized CYBB selected from the group consisting of jCAT codon optimized CYBB (SEQ ID NO:18), GeneArt optimized CYBB (SEQ ID NO:20), IDT optimized CYBB SEQ ID NO:21), and previous clinical candidate (SEQ ID NO: 19).

Embodiment 28: The vector of embodiment 26, wherein the sequence of said nucleic acid that encodes gp91$^{phox}$ is a jCAT codon optimized CYBB (SEQ ID NO:18).

Embodiment 29: The vector according to any one of embodiments 1-28, wherein said vector comprises a ψ region vector genome packaging signal.

Embodiment 30: The vector according to any one of embodiments 1-29, wherein said vector comprise a 5' LTR comprising a CMV enhancer/promoter.

Embodiment 31: The vector according to any one of embodiments 1-30, wherein said vector comprises a Rev Responsive Element (RRE).

Embodiment 32: The vector according to any one of embodiments 1-31, wherein said vector comprises a central polypurine tract.

Embodiment 33: The vector according to any one of embodiments 1-32, wherein said vector comprises a post-translational regulatory element.

Embodiment 34: The vector of embodiment 33, wherein the posttranscriptional regulatory element is modified Woodchuck Post-transcriptional Regulatory Element (WPRE).

Embodiment 35: The vector according to any one of embodiments 1-34, wherein said vector is incapable of reconstituting a wild-type lentivirus through recombination.

Embodiment 36: The vector of embodiment 1, wherein said vector comprises the features of full-sized 2-4R-Int3-pro-mCit-WPRE shown in FIG. 19, where the mCit is replaced with a nucleic acid encoding Gp91$^{phox}$.

Embodiment 37: The vector of embodiment 1, wherein said vector comprises the features of UC 2-4R-Int3-pro-coGp91$^{phox}$-WRPE shown in FIG. 20, panel A.

Embodiment 38: The vector of embodiment 37, wherein said vector comprise the features shown in the vector represented in FIG. 20, panel B.

Embodiment 39: The vector of embodiment 38, wherein said vector comprises the nucleotide sequence of ultra core (UC) 2-4R-Int3-Pro-(GP91-jcat)-WPRE (SEQ ID NO: 22).

Embodiment 40: The vector according to any one of embodiments embodiment 1-39, wherein said vector shows high expression in CD33+(bulk myeloid cells), high expression in CD19+(B cells, high expression in CD66b+ CD15+ CD11b+ CD16+ (mature neutrophils), and low or no expression in CD3+ T cells.

Embodiment 41: A host cell transduced with a vector according to any one of embodiments 1-40.

Embodiment 42: The host cell of embodiment 41, wherein the cell is a stem cell.

Embodiment 43: The host cell of embodiment 42, wherein said cell is a stem cell derived from bone marrow, and/or from umbilical cord blood, and/or from peripheral blood.

Embodiment 44: The host cell of embodiment 41, wherein the cell is a human hematopoietic progenitor cell.

Embodiment 45: The host cell of embodiment 44, wherein the human hematopoietic progenitor cell is a CD34+ cell.

Embodiment 46: A method of treating a chronic granulomatous disease (X-CGD), in a subject, said method comprising:

- transducing a stem cell and/or progenitor cell from said subject with a vector according to any one of embodiments 1-40; and
- transplanting said transduced cell or cells derived therefrom into said subject where said cells or derivatives therefrom express said Gp91$^{phox}$.

Embodiment 47: The method of embodiment 46, wherein the cell is a stem cell.

Embodiment 48: The host cell of embodiment 46, wherein said cell is a stem cell derived from bone marrow.

Embodiment 49: The method of embodiment 46, wherein the cell is a human hematopoietic stem and progenitor cell.

Embodiment 50: The method of embodiment 49, wherein the human hematopoietic progenitor cell is a CD34+ cell.

Embodiment 51: A recombinant nucleic acid encoding one or more of the following:

- a CYBB promoter, or an effective fragment thereof; and/or
- a CYBB endogenous enhancer element 2 (CYBB B-cell enhancer), or an effective fragment thereof; and/or
- a CYBB endogenous enhancer 4R (CYBB endogenous myeloid enhancer), or an effective fragment thereof; and/or
- a CYBB endogenous enhancer 4L, or an effective fragment thereof; and/or
- a CYBB endogenous myeloid Intron 3 enhancer, or an effective fragment thereof; and/or
- a codon optimized nucleic acid encoding Gp91$^{phox}$.

Embodiment 52: The nucleic acid of embodiment 51, wherein said nucleic acid encodes a sequence comprising or consisting of a full-length endogenous CYBB promoter (SEQ ID NO:1).

Embodiment 53: The nucleic acid of embodiment 51, wherein said nucleic acid encodes a sequence comprising an effective fragment of a CYBB promoter where said fragment comprises or consists of the minimal CYBB promoter (core) (SEQ ID NO: 2).

Embodiment 54: The nucleic acid of embodiment 53, wherein said nucleic acid encodes a sequence comprising an effective fragment of a CYBB promoter where said fragment consists of the minimal CYBB promoter (core) (SEQ ID NO: 2).

Embodiment 55: The nucleic acid of embodiment 51, wherein said nucleic acid encodes a sequence comprising an effective fragment of a CYBB promoter where said fragment comprises or consists of the minimal CYBB promoter (ultra core) (SEQ ID NO:3).

Embodiment 56: The nucleic acid of embodiment 55, wherein said nucleic acid encodes a sequence comprising an effective fragment of a CYBB promoter where said fragment consists of the minimal CYBB promoter (ultra core) (SEQ ID NO:3).

Embodiment 57: The nucleic acid according to any one of embodiments 51-56, wherein said nucleic acid encodes an effective fragment of a CYBB endogenous enhancer element 2 (CYBB B-cell enhancer).

Embodiment 58: The nucleic acid of embodiment 57, wherein the nucleic acid sequence of said a CYBB endogenous enhancer element 2 comprises or consists of the sequence of enhancer element 2 core (SEQ ID NO:5).

Embodiment 59: The nucleic acid of embodiment 57, wherein the nucleic acid sequence of said a CYBB endogenous enhancer element 2 comprises or consists of the sequence of enhancer element 2 ultra core (SEQ ID NO: 6).

Embodiment 60: The nucleic acid according to any one of embodiments 51-59, wherein said nucleic acid comprises an effective fragment of a CYBB endogenous enhancer 4R (CYBB endogenous myeloid enhancer).

Embodiment 61: The nucleic acid of embodiment 60, wherein the nucleic acid sequence of said effective fragment of a CYBB endogenous enhancer 4R comprises or consists of the sequence of enhancer element 4R ultra core (SEQ ID NO:10).

Embodiment 62: The nucleic acid according to any one of embodiments 51-61, wherein said nucleic acid comprises an effective fragment of an enhancer element 4L.

Embodiment 63: The nucleic acid of embodiment 62, wherein said effective fragment of an enhancer element 4L comprises or consists of the sequence of the 4L core sequence (SEQ ID NO:13).

Embodiment 64: The nucleic acid according to any one of embodiments 51-63, wherein said nucleic acid comprises an effective fragment of a CYBB endogenous myeloid intron 3 enhancer.

Embodiment 65: The nucleic acid of embodiment 64, wherein the nucleic acid sequence of said effective fragment of a CYBB endogenous myeloid intron 3 enhancer comprises or consists of an element 3 middle fragment nucleic acid sequence (SEQ ID NO:15).

Embodiment 66: The nucleic acid according to any one of embodiments 64-65, wherein the nucleic acid sequence of said effective fragment of a CYBB endogenous myeloid intron 3 enhancer comprises or consists of an intron enhancer element 3 right fragment (SEQ ID NO: 16).

Embodiment 67: The nucleic acid according to any one of embodiments 51-66, wherein said nucleic acid comprises a jCAT codon optimized CYBB (SEQ ID NO:18).

Embodiment 68: The nucleic acid according to any one of embodiments 51-67, wherein said nucleic acid comprises an expression cassette.

Embodiment 69: The nucleic acid of embodiment 68, wherein said expression cassette is effective to express Gp91$^{phox}$ in vivo.

Embodiment 70: The nucleic acid according to any one of embodiments 51-69, wherein said nucleic acid comprises a lentiviral vector according to any one of embodiments 1-40.

Definitions

A "promoter" refers to a regulatory sequence in a nucleic acid required to initiate transcription of a gene (e.g., a gene operably coupled to the promoter).

An "enhancer" refers to a regulatory DNA sequence that, when bound by specific proteins called transcription factors, enhance the transcription of an associated gene.

An "effective fragment" when used with respect to a promoter (e.g., an effective fragment of a CYBB promoter) refers to a fragment of the full-length promoter that is sufficient to initiate transcription of a gene operably linked to that promoter.

An "effective fragment" when used with respect to an enhancer (e.g., an effective fragment of a CYBB enhancer) refers to a fragment of the full-length enhancer that is sufficient to provide regulate expression of an operably linked gene when bound by a transcription factor. In certain embodiments the regulation is comparable with respect to expression level and/or lineage offered by the full-length enhancer.

The term "operably linked" refers to a nucleic acid sequence placed into a functional relationship with another nucleic acid sequence. For example, a promoter is operably linked to a gene when that promoter is placed in a location that permits that promoter to initiate transcription of that gene. An enhancer is operably linked to a gene when that enhancer, when bound by an appropriate transcription factor, is able to regulate (e.g., to upregulate) expression of that gene.

"Recombinant" is used consistently with its usage in the art to refer to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus is one that comprises a recombinant nucleic acid. A recombinant cell is one that comprises a recombinant nucleic acid.

As used herein, the term "recombinant lentiviral vector" or "recombinant LV) refers to an artificially created polynucleotide vector assembled from an LV and a plurality of additional segments as a result of human intervention and manipulation.

By "an effective amount" is meant the amount of a required agent or composition comprising the agent to ameliorate or eliminate symptoms of a disease relative to an untreated patient. The effective amount of composition(s) used to practice the methods described herein for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

DETAILED DESCRIPTION

Figure 1:
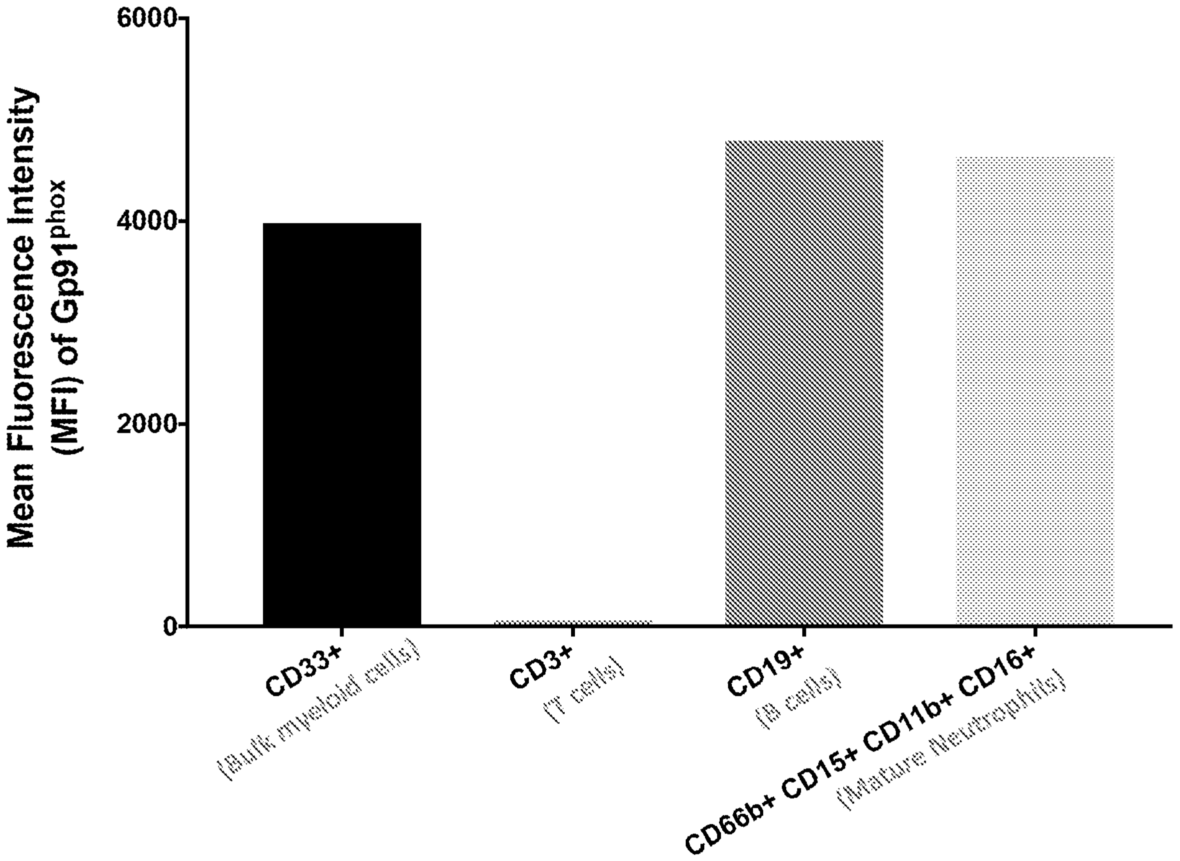
FIG. 1 illustrates the endogenous expression pattern of gp91$^{phox}$ in human blood cells.

In various embodiments, lentiviral vectors are provided for the treatment (or prophylaxis) of X-linked Chronic Granulomatous Disease (X-CGD) are provided. In certain embodiments the vectors are optimized to reduce vector size, increase expression level and titer. Additionally, In various embodiments the vectors recapitulate the lineage specific expression pattern of the native CYBB gene, e.g., as described herein (see, e.g., FIG. 1).

As described herein (see, e.g., Example 1), analysis of bioinformatics information about the CYBB gene, which produces the gp91$^{phox}$ component of the phagocytic cell anti-microbial oxidase system, identified several putative transcriptional regulatory domains, based on histone marks, DNAse hypersensitivity sites and sequence motifs for binding transcriptional factor.

Fifteen putative endogenous enhancer elements were identified within the native CYBB topologically associated domain (TAD). In order to experimentally identify the critical enhancer elements that regulate the CYBB gene, each putative enhancer element was cloned upstream of the endogenous CYBB promoter to drive expression of a reporter gene (mCitrine) (see, e.g., FIG. 2). To elucidate the function of each putative enhancer element, we assayed the activity of each of the vectors in cord blood (CB) CD34+ differentiated mature neutrophils and monocytes as well as RAMOS cells (B-lymphocyte cell line) which are 3 on-target cell lineages.

It was discovered that enhancer element 4 drives high levels of expression in mature neutrophils and in monocytes, with no expression in B-cells. It was also discovered that enhancer element 2 drives high levels of lineage specific expression in B-cells with no expression in neutrophils. None of the enhancer elements express in Jurkats (T-cells), suggesting lineage specific expression of each enhancer element.

It was also discovered that enhancer element 4 is made of two distinct enhancer modules (4L and 4R) and these were evaluated to determine if one of these elements could be eliminated to decrease the size of the vector.

Additionally, reduced variants of enhancer element 2, enhancer element 4, intron enhancer 3, and the CYBB endogenous promoter were made and evaluated. Codon optimizations of the nucleic acid encoding Gp91$^{phox}$ were also evaluated.

In view of these discoveries, in various embodiments, a recombinant lentiviral vector (LV) for the treatment of chronic granulomatous disease is provided where the vector comprises an expression cassette comprising a nucleic acid construct comprising a CYBB endogenous promoter or effective fragment thereof; and a nucleic acid that encodes gp91$^{phox}$ operably linked to the CYBB promoter or promoter fragment. In certain embodiments the CYBB promoter or effective fragment thereof comprises a full-length endogenous CYBB promoter (see, e.g., Table 1, SEQ ID NO:1). In certain embodiments the CYBB promoter comprises an effective fragment of a CYBB promoter where said fragment comprises or consists of the minimal CYBB promoter (see, e.g., Table 1, SEQ ID NO:3). In certain embodiments the CYBB promoter consists of an effective fragment of the CYBB promoter whose sequence consists of the minimal CYBB promoter (see, e.g., Table 1, SEQ ID NO:3).

In certain embodiments the expression cassette in the lentiviral vector comprises an enhancer element 2 (see, e.g., Table 1, SEQ ID NO:4) or an effective fragment thereof. In certain embodiments the sequence of the effective fragment of enhancer element 2 comprises or consists of the sequence of enhancer element 2 "core" (see, e.g., Table 1, SEQ ID NO:5). In certain embodiments the sequence of the effective fragment of enhancer element 2 consists of the sequence of enhancer element 2 core (see, e.g., Table 1, SEQ ID NO:5). In certain embodiments the sequence of the effective fragment of enhancer element 2 comprises or consists of the enhancer element 2 "ultra core" sequence (see, e.g., Table 1, SEQ ID NO:6). In certain embodiments the sequence of said effective fragment of enhancer element 2 consists of the sequence of enhancer element 2 ultra core (see, e.g., Table 1, SEQ ID NO:6).

In certain embodiments the expression cassette comprising the lentiviral vector further comprises a RELA TF binding site or an effective fragment thereof. In certain embodiments the RELA TF binding site comprises or consists of the nucleic acid sequence of SEQ ID NO:7 in Table 1, In certain embodiments the expression cassette in the lentiviral vector comprises enhancer element 4 (see, e.g., Table 1, SEQ ID NO:8) or an effective fragment thereof. In certain embodiments the expression cassette comprises an enhancer element 4R (see, e.g., Table 1, SEQ ID NO:9) or an effective fragment thereof. In certain embodiments the expression cassette comprises an effective fragment of enhancer element 4R where the nucleic acid sequence comprises or consists of the nucleic acid sequence of enhancer element 4R core (see, e.g., Table 1, SEQ ID NO:10). In certain embodiments the expression cassette comprises an effective fragment of enhancer element 4R where the nucleic acid sequence of said fragment comprises or consists of the nucleic acid sequence of enhancer element 4R "ultra core" (see, e.g., Table 1, SEQ ID NO:11). In certain embodiments the expression cassette comprises an effective fragment of enhancer element 4R where the nucleic acid sequence of said fragment consists of the nucleic acid sequence of enhancer element 4R ultra core (see, e.g., Table 1, SEQ ID NO:11).

In certain embodiments the expression cassette in the lentiviral vector comprises an enhancer element 4L ((see, e.g., Table 1, SEQ ID NO:12) or an effective fragment thereof. In certain embodiments the effective fragment of enhancer element 4L comprises or consists of the sequence of 4L core sequence (see, e.g., Table 1, SEQ ID NO:13). In certain embodiments the effective fragment of enhancer element 4L consists of the sequence of 4L core sequence (see, e.g., Table 1, SEQ ID NO:13).

In certain embodiments the expression cassette in the lentiviral vector comprises an intron enhancer element 3 (see, e.g., Table 1, SEQ ID NO:14) or an effective fragment thereof. In certain embodiments the expression cassette in the lentiviral vector comprises or consists of an intron enhancer element 3 middle fragment comprising or consisting of the nucleic acid sequence of SEQ ID NO:15 in Table 1. In certain embodiments the expression cassette in the lentiviral vector consists of an intron enhancer element 3 middle fragment comprising or consisting of the nucleic acid sequence of SEQ ID NO:15 in Table 1. In certain embodiments the expression cassette in the lentiviral vector comprises or consists of an intron enhancer element 3 right fragment comprising or consisting of the nucleic acid sequence of SEQ ID NO: 16 in Table 1.

In certain embodiments the nucleic acid that encodes gp91$^{phox}$ is a full CYBB gene, a CYBB cDNA, or a codon-optimized CYBB. In certain embodiments the nucleic acid that encodes gp91$^{phox}$ is a CYBB cDNA (see, e.g., Table 1, SEQ ID NO:17). In certain embodiments the nucleic acid that encodes gp91$^{phox}$ is a codon optimized CYBB (e.g., a jCAT codon optimized CYBB (see, e.g., Table 1, SEQ ID NO:18), a GeneArt optimized CYBB (see, e.g., Table 1, SEQ ID NO:20), an IDT optimized CYBB (see, e.g., Table 1, SEQ ID NO:21), and previous clinical candidate (see, e.g., Table 1, SEQ ID NO: 19)). In certain embodiments the sequence of said nucleic acid that encodes gp91$^{phox}$ is a jCAT codon optimized CYBB (see, e.g., Table 1, SEQ ID NO: 18).

It will be recognized that the expression cassettes described herein in the context of lentiviral vectors need not be limited to this context. Accordingly, in certain embodiments, a recombinant nucleic acid comprising any one or more of the CYBB regulatory elements described herein is contemplated. In certain embodiments the recombinant nucleic acid comprises an expression cassette, e.g., an expression cassette effective to express Gp91$^{phox}$ in vivo. It will be recognized that such an expression cassette can be used with other constructs, e.g., in conjunction with a CRISPR construct.

TABLE 1

Nucleic acid sequences of various components of the lentiviral vectors for treatment of X-CGD as described herein.

| Element SEQ ID NO | Nucleic Acid Sequence |
|---|---|
| CYBB promoter (endogenous CYBB (SEQ ID NO: 1) | TAGCACATAAAATTGGCACATATTAAGCATTTTGTAAATATCAACCAT<br>TACAATTGTTACTACTTTTCTCAGCAAGGCTATGAATGCTGTTCCAGC<br>CTGTCAAAATCACACCTGTTTAATGTGTTTTACCCAGCACGAAGTCAT<br>GTCTAGTTGAGTGGCTTAAAAATTGTGATCAAATAGCTGGTTAGTTAA<br>AAAGTTATTTCACTGTGTAAAATACATCCCTTAAAATGCACTGTTATT<br>TATCTCTTAGTTGTAGAAATTGGTTTCATTTTCCACTATGTTTAATTG<br>TGACTGGATCATTATAGACCCTTTTTTTGTAGTTGTTGAGGTTTAAAG<br>ATTTAAGTTTGTTATGgatgcaagcttttcagttgaccaatgattatt<br>agccaatttctgataaaagaaaaggaaaccgattgccccagggctgct<br>gttttcatttcctcattggaAGAAGAAGCATAGTATAGAAGAAAGGCA<br>AACACAACACATTCAACCTCTGCCACC |
| Minimal CYBB promoter (core) (SEQ ID NO: 2) | TATCTCTTAGTTGTAGAAATTGGTTTCATTTTCCACTATGTTTAATTG<br>TGACTGGATCATTATAGACCCTTTTTTTGTAGTTGTTGAGGTTTAAAG<br>ATTTAAGTTTGTTATGgatgcaagcttttcagttgaccaatgattatt<br>agccaatttctgataaaagaaaaggaaaccgattgccccagggctgct<br>gttttcatttcctcattggaAGAAGAAGCATAGTATAGAAGAAAGGCA<br>AACACAACACATTCAACCTCTGCCACC |
| Minimal CYBB promoter (ultra-core) (SEQ ID NO: 3) | TTTAAGTTTGTTATGgatgcaagcttttcagttgaccaatgattatta<br>gccaatttctgataaaagaaaaggaaaccgattgccccagggctgctg<br>ttttcatttcctcattggaAGAAGAAGCATAGTATAGAAGAAAGGCAA<br>ACACAACACATTCAACCTCTGCCACC |
| Enhancer element 2 (SEQ ID NO: 4) | **GCTTAGTCATGTTGGTCCCAAAGTCATAGTTGATGAGAAGTAGCAAGT**<br>**TAAGAGAGAAAGACTTCTAGAGATAGGTACATACACAATGATAACAAG**<br>**TGACATCAGAGAACCTAAGGAAGGGCAAAGAAAGAAACACTGCAAAGC**<br>**AGACTCAAACACTTAAAAGCATAGCAGCTTGGGGCCAGTTAGTGTAAG**<br>**AGAAAAGGAGCTCCATATGCCTCAATAGAACCTAAGAGCATCATTGTA**<br>**CTGCATTTATTCATTCATTCACTTCACATGTTTATTCAACAAATGCTA**<br>**TGTATACTGAGATTTTTCTCTGGTCATTGTACTGGCTAGAACCTAAAG**<br>**GAGTGAGACTATTAATTAGAGTTTACAATCTGGCAATGATATTAACAG**<br>**TCTATTCACAAAAGGGTTAACTCAAGTTAAGCCGGCCTAAATGTTTAT**<br>**GCAAAATAGGATTTTTGCCTAAGTCTAAAGGGTATCAGAAAAGTGTAG**<br>**CCATTGAGAATGACTCATTTCATGGTGTTCTCGGATGGCTTAAGTATT**<br>**ATTAATATGTCTCCATTTCTAGTGCAGGAACCTCCACGTTTTAGAGGA**<br>**AAGGAGGAAAGAATTTGTGAAGACTGTGCCTAAAAAAGGTAGAAATTT**<br>**GTTTACAATTTATTTAAAGATAAAAGTAAAGAACTAGGTTGCTTTAAA**<br>**AAAGGGAGGGAAAGAAAATCAAAATACATCTTATTTGAGGCATTAAAA**<br>**CTTTTTTAAGAAAATAAAATTTAAAATAAAGTTGTATTCTTCTAAAAA** |

TABLE 1-continued

Nucleic acid sequences of various components of the lentiviral vectors for treatment of X-CGD as described herein.

| Element SEQ ID NO | Nucleic Acid Sequence |
|---|---|
| | **TAATTTTTTAAACCAGCTGAAAATGAAAAATGCAGATTATACTAAGAA**<br>**GCAACTGTTTTACATTCTGCTTTCTGAATGGTATTTAAAAACTCAGTT**<br>**ATTTTCAGAAATGAGGAAGTCTTGATCTGCTAGATGAAGGTCGGCTGC**<br>**AGGTGGTGTTTATTGCTTTATGATGGCAACAAACCGTAAACCCATCAC**<br>**TCAGTAAATATTAAACTGGCTGAATGAATCCAAAGCATGTCTAACATA**<br>**CAGGAAAAACACAGCCCTGTTAAGCAGTCTTGAAACCCACAAGCTACA**<br>**TGGAAAACACAGATTCAACTACATCATAAAAATTCA** |
| Enhancer element 2 core (SEQ ID NO: 5) | **GAGCTCCATATGCCTCAATAGAACCTAAGAGCATCATTGTACTGCATT**<br>**TATTCATTCATTCACTTCACATGTTTATTCAACAAATGCTATGTATAC**<br>**TGAGATTTTTCTCTGGTCATTGTACTGGCTAGAACCTAAAGGAGTGAG**<br>**ACTATTAATTAGAGTTTACAATCTGGCAATGATATTAACAGTCTATTC**<br>**ACAAAAGGGTTAACTCAAGTTAAGCCGGCCTAAATGTTTATGCAAAAT**<br>**AGGATTTTTGCCTAAGTCTAAAGGGTATCAGAAAAGTGTAGCCATTGA**<br>**GAATGACTCATTTCATGGTGTTCTCGGATGGCTTAAGTATTATTAATA**<br>**TGTCTCCATTTCTAGTGCAGGAACCTCCACGTTTTAGAGGAAAGGAGG**<br>**AAAGAATTTGTGAAGACTGTGCCTAAAAAAGGTAGAAATTTGTTTACA**<br>**ATTTATTTAAAGATAAAAGTAAAGAACTAGGTTGCTTTAAAAAAGGGA**<br>**GGGAAAGAAAATCAAAATACATCTTATTTGAGGCATTAAAACTTTTTT**<br>**AAGAAAATAAAATTTAAAATAAAGTTGTATTCTTCTAAAAATAATTTT**<br>**TTAAACCAGCTGAAAATGAAAAATGCAGATTATACTAAGAAGCAACTG**<br>**TTTTACATTCTGCTTTCTGAATGGTATTTAAAAACTCAGTTATTTTCA**<br>**GAAATGAGGAAGTCTTGATCTGCTAGATGAAGGTCGGCTGCAGGTGGT**<br>**GTTTATTGCTTTATGATGGCAACAAACCGTAAACCCATCACTCAGTAA**<br>**ATATTAAACTGGCTGAATGAATCCAAAGCATGTCTAACATACAGGAAA**<br>**AACACAGCCCTGTTAAGCAGTCTTGAAACCCACAAGCTACATGGAAAA**<br>**CACAGATTCAACTACATCATAAAAATTC** |
| Enhancer element 2 ultra core (SEQ ID NO: 6) | AAATCAAAATACATCTTATTTGAGGCATTAAAACTTTTTTAAGAAAAT<br>AAAATTTAAAATAAAGTTGTATTCTTCTAAAAATAATTTTTTAAACCA<br>GCTGAAAATGAAAAATGCAGATTATACTAAGAAGCAACTGTTTTAGAT<br>TCTGCTTTCTGAATGGTATTTAAAAACTCAGTTATTTTCAGAAATGAG<br>GAAGTCTTGATCTGCTAGATGAAGGTCGGCTGCAGGTGGTGTTTATTG<br>CTTTATGATGGCAACAAACCGTAAACCCATCACTCAGTAAATATTAAA<br>CTGGCTGAATGAATCCAAAGCATGTCTAACATACAGGAAAAACACAGC<br>CCTGTTAAGCA |
| Element 2 RELA TF binding site (SEQ ID NO: 7) | AACTGCCCAGGCCATCCACAGATGACTGTAGATACATGTGTAAGTTCA<br>GTTCACATCCTCAGAACCACCCAGATGTCCTGTAGATGCATGAGAAAT<br>GTTAAATGCTTGTTGTTTTAAGCCACTAACTTCAGAGTAGTTTGTTAT<br>ATAACAAAACCGCTGATGCAAATGGCATCAAAAATTGTTGAAAGAGAG<br>ATGGGGGTTCAGGGTGAGAGCTGTAGGTGATTGTATCTGTGCTAATAC<br>CACATAGCCCTTTTTTGGGGATTGCCATGAATAATATATTAGCTTTGC<br>TATGAGTAAAATACTATATCCTCTGAATTGTCATGAATTACGTGGAGT<br>CATACGTGTTTTGGAAGTGTGAAAGTCCCTGGGCTCAGATAAAAGGTG<br>TTGCCATCTGGAAAGTACAGGTAGTTTATTTCAATTCTGCTCCAATAA<br>CTAGCACGTCATTCCATTCATGTAGAAATAAGCTACTGGCTATCTCAC<br>TATCTGAAATAGAAGTATGAACTGTGGGTAAGTGGGTGAGGACAATGT<br>CTGAGCAACCAAAAAGGAGCTCAAATCC |
| Enhancer element 4 (SEQ ID NO: 8) | AAACTAATATGACCTTATAAGAGGAGGAAGTTGGGGCACAGGCATGTA<br>CACACAGAGGAAAGACCATACAGAGGAAAGACCATATTAAGATAAAGG<br>AAGAGGATGACCATCTACAAGCCAAGCAAAGGGGCCCCAGAAGGAAAC<br>CAAACATGCTGAAACCTTGATCTTGAATTTGTAGCTTCTAAAACTGTG<br>AGAAAATAAATTTCTGTTGTTTAAAACATCCAGGCTGAGGTACTTTGT<br>TATGGAAGCCCTGTCAAACTAATGCAACAACATTTCCTCCCATTAGAT<br>TTCTTAATTCGTGTATAGCTGGCCTGATAATGTCTTATCAGCTACCCC<br>AACTCAATTGCTGCAAATACATTTTTAAAAGTTCTGGTGGTTGTAGTT<br>GATTGCACACTTCTGTATGAGCCAATAATGTGAGGCAAGTCTTTAAAA<br>GGGTAGCACAATCAGTCTGAGGTTACACCATAGATATGGTTAACCATA<br>GTGTGGTCTCCATAACATAGGAAGTCAAGATCCCCCTTCACTCTTGAC<br>CAGTCAGATTGCACCTAGAACATTTTTCTCAATTCTGCATACCACATT<br>TAAAGAGGAAGACAAAACCCATGCGTTGTGCAGCTACCACATGTCGAG<br>CATCAGACTATGTGCACTGTGTACACTTAGTCCTCCCACCAACCCAAT<br>GAAGATGGTATTAATACCCACCTCCCATTGTACAGATGAGGAGACTGG<br>GGCTAAATGAGGTCAAATAGGTTGCTCAACAGAGATCTTCACCTCCAT<br>GGACTCCCATAGCCACACTCTGAACCCTGTCATCTCTCAGAAGTGCAC<br>TGCTTCTGAAATCTGCATCTCATACACCCATCCTCTGACTACCACCTC<br>CTGTTCCCTGGCTTCCTAATTCACTCACACCCAAGATGACTGTCCTTC<br>AACCTCATCAAACTTTGAGTTCTTTTTGACTCTTTGACTTTGCTCCCA<br>TCTTGTGTTCACTTCTTGGCATTCTACTCATCTTAGACTCAGTTCACT<br>TCTGCCATTTTCTTGCACAAATCCTGAATTCTCTCATGCAGTGCCCTT<br>CTGTACCACCTGCAGGCAAAAACCAACCCTGATCAACTCAATTGTCCT<br>CTATACTTGCTCGTGGGTGGGTAAGAAAAGCTAGAAAAGCTACCCACA |

TABLE 1-continued

Nucleic acid sequences of various components of the lentiviral vectors for treatment of X-CGD as described herein.

| Element SEQ ID NO | Nucleic Acid Sequence |
|---|---|
| | GACTCCTACCATTACTGATTTATGAGCTCCAGGCTCAACTGGGCCCTT<br>ATCTGGGCCTGGAAATCATTTTGCATTTCTACAGTCAAGTCTCCTTTC<br>TGAACAAAAGATACAACATTGAAAACTGTCTTCTGTTTCCTGAAATGT<br>CTACTCACTACCTCACTTTCAACAGATAACCTTGCCCTCTCTTTCACA<br>AAGGAAATGGAAACCACAAAGAGGAAGTCCCTCACCCTGCTGTCCCCA<br>GCCCTACAAATCCTCCTGCATCTGCACTCTGCTCCTTCCCTCTTTTTA<br>CAGAGAGGAGGCCCCTCCTGTCTAAAGCAAATTCCATTTCCTTCCTGC<br>CTTGGGCTCAGAAATCTCACCCCATCCAAAATCTTCCATGGTTAGCCT<br>GTCCCTTTGTTGCGACTCTTTCTCAATATTTACAAGCTCCTATATTTT<br>TTAAAATAATAAAACTAGGTCCTCCTGGTGTTCACATGTTTTCCCAAT<br>TGTAGCCAAGTCCTCTCATTCTTATCACAGCCTCAGACATTTTGAGGT<br>GTCTCACTACCTCACCTCAACCCACAACATCTGGCTTCCCTCATTGTT<br>TTCCAGTAGGCCCCTT |
| Enhancer element 4R (SEQ ID NO: 9) | CAGAGATCTTCACCTCCATGGACTCCCATAGCCACACTCTGAACCCTG<br>TCATCTCTCAGAAGTGCACTGCTTCTGAAATCTGCATCTCATACACCC<br>ATCCTCTGACTACCACCTCCTGTTCCCTGGCTTCCTAATTCACTCACA<br>CCCAAGATGACTGTCCTTCAACCTCATCAAACTTTGAGTTCTTTTTGA<br>CTCTTTGACTTTGCTCCCATCTTGTGTTCACTTCTTGGCATTCTACTC<br>ATCTTAGACTCAGTTCACTTCTGCCATTTTCTTGCACAAATCCTGAAT<br>TCTCTCATGCAGTGCCCTTCTGTACCACCTGCAGGCAAAAACCAACCC<br>TGATCAACTCAATTGTCCTCTATACTTGCTCGTGGGTGGGTAAGAAAA<br>GCTAGAAAAGCTACCCACAGACTCCTACCATTACTGATTTATGAGCTC<br>CAGGCTCAACTGGGCCCTTATCTGGGCCTGGAAATCATTTTGCATTTC<br>TACAGTCAAGTCTCCTTTCTGAACAAAAGATACAACATTGAAAACTGT<br>CTTCTGTTTCCTGAAATGTCTACTCACTACCTCACTTTCAACAGATAA<br>CCTTGCCCTCTCTTTCACAAAGGAAATGGAAACCACAAAGAGGAAGTC<br>CCTCACCCTGCTGTCCCCAGCCCTACAAATCCTCCTGCATCTGCACTC<br>TGCTCCTTCCCTCTTTTTACAGAGAGGAGGCCCCTCCTGTCTAAAGCA<br>AATTCCATTTCCTTCCTGCCTTGGGCTCAGAAATCTCACCCCATCCAA<br>AATCTTCCATGGTTAGCCTGTCCCTTTGTTGCGACTCTTTCTCAATAT<br>TTACAAGCTCCTATATTTTTTAAAATAATAAAACTAGGTCCTCCTGGT<br>GTTCACATGTTTTCCCAATTGTAGCCAAGTCCTCTCATTCTTATCACA<br>GCCTCAGACATTTTGAGGTGTCTCACTACCTCACCTCAACCCACAACA<br>TCTGGCTTCCCTCATTGTTTTCCAGTAGGCCCCTT |
| Enhancer element 4R Core (SEQ ID NO: 10) | CATGCAGTGCCCTTCTGTACCACCTGCAGGCAAAAACCAACCCTGATC<br>AACTCAATTGTCCTCTATACTTGCTCGTGGGTGGGTAAGAAAAGCTAG<br>AAAAGCTACCCACAGACTCCTACCATTACTGATTTATGAGCTCCAGGC<br>TCAACTGGGCCCTTATCTGGGCCTGGAAATCATTTTGCATTTCTACAG<br>TCAAGTCTCCTTTCTGAACAAAAGATACAACATTGAAAACTGTCTTCT<br>GTTTCCTGAAATGTCTACTCACTACCTCACTTTCAACAGATAACCTTG<br>CCCTCTCTTTCACAAAGGAAATGGAAACCACAAAGAGGAAGTCCCTCA<br>CCCTGCTGTCCCCAGCCCTACAAATCCTCCTGCATCTGCACTCTGCTC<br>CTTCCCTCTTTTTACAGAGAGGAGGCCCCTCCTGTCTAAAGCAAATTC<br>CATTTCCTTCCTGCCTTGGGCTCAGAAATCTCACCCCATCCAAAATCT<br>TCCATGGTTAGCCTGTCCCT |
| Enhancer element 4R ultra core (SEQ ID NO: 11) | GCCCTTATCTGGGCCTGGAAATCATTTTGCATTTCTACAGTCAAGTCT<br>CCTTTCTGAACAAAAGATACAACATTGAAAACTGTCTTCTGTTTCCTG<br>AAATGTCTACTCACTACCTCACTTTCAACAGATAACCTTGCCCTCTCT<br>TTCACAAAGGAAATGGAAACCACAAAGAGGAAGTCCCTCACCCTGCTG<br>TCCCCAGCCCTACAAATCCTCCTGCATCTGCACTCTGCTCCTTCCCTC<br>TTTTTACAGAGAGG |
| Enhancer element 4L (SEQ ID NO: 12) | AAACTAATATGACCTTATAAGAGGAGGAAGTTGGGGCACAGGCATGTA<br>CACACAGAGGAAAGACCATACAGAGGAAAGACCATATTAAGATAAAGG<br>AAGAGGATGACCATCTACAAGCCAAGCAAAGGGGCCCCAGAAGGAAAC<br>CAAACATGCTGAAACCTTGATCTTGAATTTGTAGCTTCTAAAACTGTG<br>AGAAAATAAATTTCTGTTGTTTAAAACATCCAGGCTGAGGTACTTTGT<br>TATGGAAGCCCTGTCAAACTAATGCAACAACATTTCCTCCCATTAGAT<br>TTCTTAATTCGTGTATAGCTGGCCTGATAATGTCTTATCAGCTACCCC<br>AACTCAATTGCTGCAAATACATTTTTAAAAGTTCTGGTGGTTGTAGTT<br>GATTGCACACTTCTGTATGAGCCAATAATGTGAGGCAAGTCTTTAAAA<br>GGGTAGCACAATCAGTCTGAGGTTACACCATAGATATGGTTAACCATA<br>GTGTGGTCTCCATAACATAGGAAGTCAAGATCCCCCTTCACTCTTGAC<br>CAGTCAGATTGCACCTAGAACATTTTTCTCAATTCTGCATACCACATT<br>TAAAGAGGAAGACAAAACCCATGCGTTGTGCAGCTACCACATGTCGAG<br>CATCAGACTATGTGCACTGTGTACACTTAGTCCTCCCACCAACCCAAT<br>GAAGATGGTATTAATACCCACCTCCCATTGTACAGATGAGGAGACTGG<br>GGCTAAATGAGGTCAAATAGGTTGCTCAA |

TABLE 1-continued

Nucleic acid sequences of various components of the lentiviral vectors for treatment of X-CGD as described herein.

| Element SEQ ID NO | Nucleic Acid Sequence |
|---|---|
| Enhancer element 4L core (SEQ ID NO: 13) | AGCCAATAATGTGAGGCAAGTCTTTAAAAGGGTAGCACAATCAGTCTG<br>AGGTTACACCATAGATATGGTTAACCATAGTGTGGTCTCCATAACATA<br>GGAAGTCAAGATCCCCCTTCACTCTTGACCAGTCAGATTGCACCTAGA<br>ACATTTTTCTCAATTCTGCATACCACATTTAAAGAGGAAGACAAAACC<br>CATGCGTTGTGCAGCT |
| Full Intron 3 Enhancer (SEQ ID NO: 14) | **GATCATCCCTCCTTGACTTCCATACATGTGGGGATTACAGGCATGAGT**<br>**CACCTGCCTGGCGAGTTCCTTGTTTCTAAGGAGACACAATTCATTTTT**<br>**ATTCTCCCTACCCCCATTAGAATAGTTTCTATTTAGAGGAAGTAAAGC**<br>**CTGAGAAACAGGCAATGTTTTCACCAAGATGGCCTGTTAAGAAATCTT**<br>**GGTTAGTCTACAAGTCCAAATTTCACTGCCGGTGAGCACCATGTCCCA**<br>**TGAGCAGCACATGTTGTAATGCCAGCTAGAGGTCTCAATCATTGAAAC**<br>**TTTGCTTTGTAATCCTTCTGGTTACCTAGAGAAAGAAAGCCCCAGGGT**<br>**TGCCCACCCCACCACTCCAGGAAAGGTAGGGGTAAAGGCTCTCAGACT**<br>**GCTTTGTTGAGAAAAATGGAGAATGGGTGAAGCTCAGCACACAAAAAT**<br>**CTCTGAGGAAGCCTTAAAAACCCCCAACTTGCCATGCAGAAACTAATT**<br>**TCTGTCTGGATGGCAGTCCTAGTCTTAAGATCAGAAAGAAACAGGAAG**<br>**GTGAGAGGGTGAGGTTTTATCTGTTACCTTATATAGTCTGGGAGTCAG**<br>**AGGCACTCAGTGTGCCTCTATCTTTAATCACGTGGTCTAGCACTAGTC**<br>**TCTTGGGCTTTCTGTCTCATAGTTTTTTTTTTTAGTTGAAAAACAGGT**<br>**CAACTAACACAAATGTAAGAAGGCATATGTTGGTCTAAAAGTATATTA**<br>**ATTGTTTAAGTCTGTCAATTAGTGAGTTGTCAGTCAATAAATATTTGT**<br>**TGAGTGCCATTTATGTGCTAAGCACTGGGGACATGTGGTAAGTAAAGA**<br>**TTAAGTTATAGATAGGCCATGAGCTTAAGGAGCTTAGAGTGTTAACAG**<br>**GAGAGACAGAGAATAAATATGGAACTTCCAAATTATAAACAGTGCTAT**<br>**GCAAATAAGGTAGTGTTATTCATATTTATCAGATATTCTACTGCCAGC**<br>**AGGTGTGGATATTACTGTCAACTTACTTGCCTGAGTTCTGTAGATTCA**<br>**AAGTTGGATTTTGTAATTTCTCCCAGTTGCGTATAAATATCTAAATCA**<br>**GATACATTGATGGTGCGTGTGGTGAGATCAAGTGTACAAAAAGTAGAG**<br>**CTTTTGAGTTTCTGTAAAGTGTTACACCCCATAAAATATGTACTTCTT**<br>**TTTAGTTCCACTTCCCATTTTCTTGAAATATTTTTTTCTTACTCAGTT**<br>**TCAATAGAGCATAGAAATCTGCTGAAGTGACTCAATAATCTCCCTTGC**<br>**ATTAGAATGGTAGTTTATTGAAATCGGGCAAGGCTTCCGGTGACAGTA**<br>**ACAGAGAAACTTCCCTTTAGAAGTCAATGGCAGAAAGTAAAGTAAGTT**<br>**AGTAAGGAAGCTATGGGGCATGATGGCAACGTGGATAATTGGGAAGTG**<br>**GCTGGCAATAATTTAGAAGTAACTCAAAGCATATAAATGCAATCTGCC**<br>**TGATGATGGGGAACAAAAAATTATGGGCAGTCACAGACAGTAAAGTCC**<br>**TTCCTTCCTATGCCACCAACCGGTTGTCTCGCCTCCTTTTTTAAGGAA**<br>**GTGGTGAGGAGATGGTATTCTTAAAAGCCCAGTATCAGCATGACTTGT**<br>**GGCTTCTTTTTGGATTTGTTTGCCATTCCTGTCCACACCAAAGAGGGT**<br>**AGGTGGGAAAAATTAGGGATTTGTGCCCTGATGGTTGGACCCACTCCA**<br>**CTGATCCATTAGTTACTAGTAATCTCACTTTTTCCTTTCAATATAATA**<br>**TATGTGTTTTACATTAACTAGCTTTTTAAAAATTACCTATTAAGATGA**<br>**AA** |
| Middle fragment INT3 enhancer ultra core SEQ ID NO: 15) | CTTAAAAACCCCCAACTTGCCATGCAGAAACTAATTTCTGTCTGGATG<br>GCAGTCCTAGTCTTAAGATCAGAAAGAAACAGGAAGGTGAGAGGGTGA<br>GGTTTTATCTGTTACCTTATATAGTCTGGGAGTCAGAGGCACTCAGTG<br>TGCCTCTATCTTTAATCACGTGGTCTAGCACTAGTCTCTTGGGCTTTC<br>TGTCTCATAGTTTTTTTTTTTAGTTGAAAAACAGGTCAACTAACACAA<br>ATGTAAGAAGGCATATGTTGGTCTAAAAGTATATTA |
| Right Fragment INT3 enhancer ultra core SEQ ID NO: 16) | AGCTTTTGAGTTTCTGTAAAGTGTTACACCCCATAAAATATGTACTTC<br>TTTTTAGTTCCACTTCCCATTTTCTTGAAATATTTTTTTCTTACTCAG<br>TTTCAATAGAGCATAGAAATCTGCTGAAGTGACTCAATAATCTCCCTT<br>GCATTAGAATGGTAGTTTATTGAAATCGGGCAAGGCTTCCGGTGACAG<br>TAACAGAGAAACTTCCCTTTAGAAGTCAATGGCAGAAAGTAAAGTAAG<br>TTAGTAAGGAAGCTATGGGGCATGATGGCAACGTGGATAATTGGGAAG<br>TGGCTGGCAATAATTTAGAAGTAACTCAAAGCATATAAATGCAATCTG<br>CCTGATGATGGGGAACAAAAAATTATGGGCAGTCACAGACAGTAAAGT<br>CCTTCCTTCCTATGCCACCAACCGGTTGTCTCGCCTCCTTTTTTAAGG<br>AAGTGGTGAGGA |
| Gp91$^{phox}$ cDNA (SEQ ID NO: 17) | ATGGGGAACTGGGCTGTGAATGAGGGGCTCTCCATTTTTGTCATTCTG<br>GTTTGGCTGGGGTTGAACGTCTTCCTCTTTGTCTGGTATTACCGGGTT<br>TATGATATTCCACCTAAGTTCTTTTACACAAGAAAACTTCTTGGGTCA<br>GCACTGGCACTGGCCAGGGCCCCTGCAGCCTGCCTGAATTTCAACTGC<br>ATGCTGATTCTCTTGCCAGTCTGTCGAAATCTGCTGTCCTTCCTCAGG<br>GGTTCCAGTGCGTGCTGCTCAACAAGAGTTCGAAGACAACTGGACAGG<br>AATCTCACCTTTCATAAAATGGTGGCATGGATGATTGCACTTCACTCT<br>GCGATTCACACCATTGCACATCTATTTAATGTGGAATGGTGTGTGAAT<br>GCCCGAGTCAATAATTCTGATCCTTATTCAGTAGCACTCTCTGAACTT<br>GGAGACAGGCAAAATGAAAGTTATCTCAATTTTGCTCGAAAGAGAATA<br>AAGAACCCTGAAGGAGGCCTGTACCTGGCTGTGACCCTGTTGGCAGGC |

TABLE 1-continued

Nucleic acid sequences of various components of the lentiviral vectors for treatment of X-CGD as described herein.

| Element SEQ ID NO | Nucleic Acid Sequence |
|---|---|
| | ATCACTGGAGTTGTCATCACGCTGTGCCTCATATTAATTATCACTTCC<br>TCCACCAAAACCATCCGGAGGTCTTACTTTGAAGTCTTTTGGTACACA<br>CATCATCTCTTTGTGATCTTCTTCATTGGCCTTGCCATCCATGGAGCT<br>GAACGAATTGTACGTGGGCAGACCGCAGAGAGTTTGGCTGTGCATAAT<br>ATAACAGTTTGTGAACAAAAAATCTGAGAATGGGGAAAAATAAAGGAA<br>TGCCCAATCCCTCAGTTTGCTGGAAACCCTCCTATGACTTGGAAATGG<br>ATAGTGGGTCCCATGTTTCTGTATCTCTGTGAGAGGTTGGTGCGGTTT<br>TGGCGATCTCAACAGAAGGTGGTCATCACCAAGGTGGTCACTCACCCT<br>TTCAAAACCATCGAGGTACAGATGAAGAAGAAGGGGTTCAAAATGGAA<br>GTGGGACAATACATTTTTGTCAAGTGCCCAAAGGTGTCCAAGCTGGAG<br>TGGCACCCTTTTACACTGACATCCGCCCCTGAGGAAGACTTCTTTAGT<br>ATCCATATCCGCATCGTTGGGGACTGGACAGAGGGGCTGTTCAATGCT<br>TGTGGCTGTGATAAGCAGGAGTTTCAAGATGCGTGGAAACTACCTAAG<br>ATAGCGGTTGATGGGCCCTTTGGCACTGCCAGTGAAGATGTGTTCAGC<br>TATGAGGTGGTGATGTTAGTGGGAGCAGGGATTGGGGTCACACCCTTC<br>GCATCCATTCTCAAGTCAGTCTGGTACAAATATTGCAATAACGCCACC<br>AATCTGAAGCTCAAAAAGATCTACTTCTACTGGCTGTGCCGGGACACA<br>CATGCCTTTGAGTGGTTTGCAGATCTGCTGCAACTGCTGGAGAGCCAG<br>ATGCAGGAAAGGAACAATGCCGGCTTCCTCAGCTACAACATCTACCTC<br>ACTGGCTGGGATGAGTCTCAGGCCAATCACTTTGCTGTGCACCATGAT<br>GAGGAGAAAGATGTGATCACAGGCCTGAAACAAAAGACTTTGTATGGA<br>CGGCCCAACTGGGATAATGAATTCAAGACAATTGCAAGTCAACACCCT<br>AATACCAGAATAGGAGTTTTCCTCTGTGGACCTGAAGCCTTGGCTGAA<br>ACCCTGAGTAAACAAAGCATCTCCAACTCTGAGTCTGGCCCTCGGGGA<br>GTGCATTTCATTTTCAACAAGGAAAACTTCTAA |
| jCAT Codon optimized Gp91$^{phox}$ (SEQ ID NO: 18) | ATGGGCAACTGGGCCGTGAACGAGGGCCTGAGCATCTTCGTGATCCTG<br>GTGTGGCTGGGCCTGAACGTGTTCCTGTTCGTGTGGTACTACCGCGTG<br>TACGACATCCCCCCCAAGTTCTTCTACACCCGCAAGCTGCTGGGCAGC<br>GCCCTGGCCCTGGCCCGCGCCCCCGCCGCCTGCCTGAACTTCAACTGC<br>ATGCTGATCCTGCTGCCCGTGTGCCGCAACCTGCTGAGCTTCCTGCGC<br>GGCAGCAGCGCCTGCTGCAGCACCCGCGTGCGCCGCCAGCTGGACCGC<br>AACCTGACCTTCCACAAGATGGTGGCCTGGATGATCGCCCTGCACAGC<br>GCCATCCACACCATCGCCCACCTGTTCAACGTGGAGTGGTGCGTGAAC<br>GCCCGCGTGAACAACAGCGACCCCTACAGCGTGGCCCTGAGCGAGCTG<br>GGCGACCGCCAGAACGAGAGCTACCTGAACTTCGCCCGCAAGCGCATC<br>AAGAACCCCGAGGGCGGCCTGTACCTGGCCGTGACCCTGCTGGCCGGC<br>ATCACCGGCGTGGTGATCACCCTGTGCCTGATCCTGATCATCACCAGC<br>AGCACCAA<br>GACCATCCGCCGCAGCTACTTCGAGGTGTTCTGGTACACCCAC<br>CACCTGTTCGTGATCTTCTTCATCGGCCTGGCCATCCACGGCGCCGAG<br>CGCATCGTGCGCGGCCAGACCGCCGAGAGCCTGGCCGTGCACAACATC<br>ACCGTGTGCGAGCAGAAGATCAGCGAGTGGGGCAAGATCAAGGAGTGC<br>CCCATCCCCCAGTTCGCCGGCAACCCCCCCATGACCTGGAAGTGGATC<br>GTGGGCCCCATGTTCCTGTACCTGTGCGAGCGCCTGGTGCGCTTCTGG<br>CGCAGCCAGCAGAAGGTGGTGATCACCAAGGTGGTGACCCACCCCTTC<br>AAGACCATCGAGCTGCAGATGAAGAAGAAGGGCTTCAAGATGGAGGTG<br>GGCCAGTACATCTTCGTGAAGTGCCCCAAGGTGAGCAAGCTGGAGTGG<br>CACCCCTTCACCCTGACCAGCGCCCCCGAGGAGGACTTCTTCAGCATC<br>CACATCCGCATCGTGGGCGACTGGACCGAGGGCCTGTTCAACGCCTGC<br>GGCTGCGACAAGCAGGAGTTCCAGGACGCCTGGAAGCTGCCCAAGATC<br>GCCGTGGACGGCCCCTTCGGCACCGCCAGCGAGGACGTGTTCAGCTAC<br>GAGGTGGTGATGCTGGTGGGCGCCGGCATCGGCGTGACCCCCTTCGCC<br>AGCATCCTGAAGAGCGTGTGGTACAAGTACTGCAACAACGCCACCAAC<br>CTGAAGCTGAAGAAGATCTACTTCTACTGGCTGTGCCGCGACACCCAC<br>GCCTTCGAGTGGTTCGCCGACCTGCTGCAGCTGCTGGAGAGCCAGATG<br>CAGGAGCGCAACAACGCCGGCTTCCTGAGCTACAACATCTACCTGACC<br>GGCTGGGACGAGAGCCAGGCCAACCACTTCGCCGTGCACCACGACGAG<br>GAGAAGGACGTGATCACCGGCCTGAAGCAGAAGACCCTGTACGGCCGC<br>CCCAACTGGGACAACGAGTTCAAGACCATCGCCAGCCAGCACCCCAAC<br>ACCCGCATCGGCGTGTTCCTGTGCGGCCCCGAGGCCCTGGCCGAGACC<br>CTGAGCAAGCAGAGCATCAGCAACAGCGAGAGCGGCCCCCGCGGCGTG<br>CACTTCATCTTCAACAAGGAGAACTTCTAA |
| Clinical co-op Gp91$^{phox}$ (SEQ ID NO: 19) | atgggcaactgggccgtgaacgagggcctgagcatcttcgtgatcctg<br>gtgtggctgggcctgaacgtgttcctgttcgtgtggtactaccgggtg<br>tacgacatcccccccaagttcttctacacccggaagctgctgggcagc<br>gccctggccctggccagagcccctgccgcctgcctgaacttcaactgc<br>atgctgatcctgctgcccgtgtgccggaacctgctgtccttcctgcgg<br>ggcagcagcgcctgctgcagcaccagagtgcggcggcagctggaccgg<br>aacctgaccttccacaagatggtggcctggatgatcgccctgcacagc<br>gccatccacaccatcgcccacctgttcaacgtggagtggtgcgtgaac<br>gcccgggtgaacaacagcgacccctacagcgtggccctgagcgagctg<br>ggcgaccggcagaacgagagctacctgaacttcgcccggaagcggatc |

TABLE 1-continued

Nucleic acid sequences of various components of the lentiviral vectors for treatment of X-CGD as described herein.

| Element SEQ ID NO | Nucleic Acid Sequence |
|---|---|
| | aagaaccccgagggcggcctgtacctggccgtgaccctgctggccggc<br>atcaccggcgtggtgatcaccctgtgcctgatcctgatcatcaccagc<br>agcaccaagaccatccggcggagctacttcgaggtgttctggtacacc<br>caccacctgttcgtgatctttttcatcggcctggccatccacggcgcc<br>gagcggatcgtgaggggccagaccgccgagagcctggccgtgcacaac<br>atcaccgtgtgcgagcagaaaatcagcgagtggggcaagatcaaagag<br>tgccccatcccccagttcgccggcaacccccccatgacctggaagtgg<br>atcgtgggccccatgttcctgtacctgtgcgagcggctggtgcggttc<br>tggcggagccagcagaaagtggtgattaccaaggtggtgacccacccc<br>ttcaagaccatcgagctgcagatgaagaaaaagggcttcaagatggaa<br>gtgggccagtacatctttgtgaagtgccccaaggtgtccaagctggaa<br>tggcacccctcaccctgaccagcgcccctgaagaggacttcttcagc<br>atccacatcagaatcgtgggcgactggaccgagggcctgttcaatgcc<br>tgcggctgcgacaagcaggaattccaggacgcctggaagctgcccaag<br>atcgccgtggacggcccctttggcaccgccagcgaggacgtgttcagc<br>tacgaggtggtgatgctggtcggagccggcatcggcgtgacccccttc<br>gccagcatcctgaagagcgtgtggtacaagtactgcaacaacgccacc<br>aacctgaagctgaagaagatctacttctactggctgtgccgggacacc<br>cacgccttcgagtggttcgccgatctgctgcagctgctggaaagccag<br>atgcaggaacggaacaacgccggcttcctgagctacaacatctacctg<br>accggctgggacgagagccaggccaaccacttcgccgtgcaccacgac<br>gaggaaaaggacgtgatcaccggcctgaagcagaaaaccctgtacggc<br>aggcccaactgggacaacgagtttaagaccatcgccagccagcacccc<br>aacacccggatcggcgtgtttctgtgcggccctgaggccctggccgag<br>acactgagcaagcagagcatcagcaacagcgagagcggccccaggggc<br>gtgcacttcatcttcaacaaagaaaacttctga |
| GeneArt optimized Gp91$^{phox}$ (SEQ ID NO: 20) | ATGGGAAACTGGGCCGTGAATGAGGGCCTGAGCATCTTCGTGATCCTC<br>GTGTGGCTGGGCCTGAACGTGTTCCTGTTCGTGTGGTACTACCGGGTG<br>TACGACATCCCTCCTAAGTTCTTCTACACCCGGAAGCTGCTGGGCTCT<br>GCTCTGGCTCTTGCTAGAGCACCAGCCGCCTGCCTGAACTTCAACTGC<br>ATGCTGATCCTGCTGCCTGTGTGCCGGAACCTGCTGAGCTTTCTGAGA<br>GGCAGCAGCGCCTGCTGTAGCACCAGAGTTAGACGGCAGCTGGACAGA<br>AACCTGACCTTCCACAAGATGGTGGCCTGGATGATCGCCCTGCACAGC<br>GCCATTCACACAATCGCCCACCTGTTCAACGTCGAGTGGTGCGTGAAC<br>GCCAGAGTGAACAACAGCGACCCTTACAGCGTGGCCCTGAGCGAGCTG<br>GGCGATAGACAGAATGAGAGCTACCTGAATTTCGCCCGGAAGCGGATC<br>AAGAACCCTGAAGGCGGACTGTACCTGGCCGTGACACTGCTGGCTGGA<br>ATCACAGGCGTGGTCATCACCCTGTGCCTGATCCTGATCATCACCAGC<br>AGCACCAAGACCATCCGGCGGAGCTACTTCGAGGTGTTCTGGTACACC<br>CACCACCTGTTTGTGATCTTTTTCATCGGCCTGGCCATCCACGGCGCC<br>GAGAGAATCGTTAGAGGACAGACAGCCGAGTCTCTGGCCGTGCACAAT<br>ATCACCGTGTGCGAGCAGAAAATCAGCGAGTGGGGCAAGATCAAAGAG<br>TGCCCCATTCCTCAGTTCGCCGGCAATCCTCCTATGACCTGGAAGTGG<br>ATCGTGGGCCCCATGTTCCTGTACCTGTGCGAAAGACTCGTGCGGTTC<br>TGGCGGAGCCAGCAGAAGGTGGTCATTACCAAGGTCGTGACACACCCC<br>TTTAAGACCATCGAGCTGCAGATGAAGAAAAAGGGCTTCAAGATGGAA<br>GTGGGCCAGTACATCTTTGTGAAGTGCCCCAAGGTGTCCAAGCTGGAA<br>TGGCACCCCTTCACACTGACAAGCGCCCCTGAAGAGGACTTCTTCAGC<br>ATCCACATCCGGATCGTCGGCGATTGGACCGAGGGCCTGTTTAATGCC<br>TGCGGCTGCGACAAGCAAGAGTTCCAGGATGCTTGGAAGCTGCCCAAG<br>ATCGCCGTGGACGGACCTTTTGGAACAGCCAGCGAGGACGTGTTCAGC<br>TACGAGGTCGTGATGCTCGTTGGAGCCGGCATCGGCGTGACACCTTTT<br>GCCAGCATCCTGAAGTCTGTGTGGTACAAGTACTGCAACAACGCCACC<br>AACCTGAAGCTCAAGAAGATCTACTTCTACTGGCTGTGCCGGGACACC<br>CACGCCTTTGAGTGGTTCGCTGATCTCCTGCAGCTGCTGGAAAGCCAG<br>ATGCAAGAGAGAAACAACGCCGGCTTCCTGAGCTACAACATCTACCTG<br>ACCGGCTGGGATGAGAGCCAGGCCAATCACTTTGCCGTGCACCACGAC<br>GAAGAGAAGGACGTGATCACCGGCCTGAAGCAGAAAACCCTGTACGGC<br>AGACCCAACTGGGACAACGAGTTCAAGACAATCGCCTCTCAGCACCCC<br>AATACCAGAATCGGAGTGTTTCTGTGCGGCCCTGAGGCTCTGGCCGAA<br>ACACTGAGCAAGCAGAGCATCAGCAACAGCGAGTCTGGCCCTAGAGGC<br>GTGCACTTCATCTTCAACAAAGAGAACTTCTGA |
| IDT optimized Gp91$^{phox}$ (SEQ ID NO: 21) | ATGGGTAACTGGGCAGTGAACGAGGGGCTTTCTATCTTTGTCATACTC<br>GTGTGGCTTGGCCTCAACGTGTTCTTGTTCGTCTGGTACTACCGAGTG<br>TACGACATTCCTCCTAAATTCTTTTACACACGCAAACTCCTTGGGTCT<br>GCTTTGGCGCTCGCTCGGGCACCTGCAGCGTGCCTGAATTTTAACTGT<br>ATGCTGATCCTCCTTCCTGTGTGCCGAAACCTTCTTTCATTCCTGCGA<br>GGTAGTTCCGCTTGCTGCTCAACTCGGGTGCGCAGGCAGCTTGACCGC<br>AACCTGACGTTCCATAAGATGGTAGCATGGATGATTGCGTTGCATTCC<br>GCGATCCACACTATCGCGCACCTCTTTAACGTGGAATGGTGTGTAAAC<br>GCGAGAGTAAATAACAGCGACCCATACTCTGTAGCACTTTCCGAACTT<br>GGAGACCGGCAGAACGAATCTTACCTTAACTTCGCTAGGAAGAGAATT |

TABLE 1-continued

Nucleic acid sequences of various components of the lentiviral vectors for treatment of X-CGD as described herein.

| Element SEQ ID NO | Nucleic Acid Sequence |
|---|---|
| | AAAAACCCAGAAGGTGGCCTTTATCTCGCGGTTACGCTGCTTGCTGGC<br>ATTACCGGCGTTGTCATAACTCTCTGTTTGATACTTATAATTACAAGC<br>TCCACCAAGACTATAAGACGATCCTACTTTGAAGTCTTCTGGTACACG<br>CACCACCTGTTCGTAATTTTCTTTATAGGACTGGCTATTCACGGTGCG<br>GAAAGGATTGTACGAGGTCAGACAGCTGAATCCCTCGCGGTGCACAAC<br>ATTACGGTATGCGAGCAGAAGATAAGTGAGTGGGGAAAAATTAAAGAG<br>TGCCCCATACCACAGTTCGCCGGCAATCCACCAATGACATGGAAGTGG<br>ATCGTGGGCCCAATGTTCCTCTACCTGTGTGAGCGCCTTGTAAGGTTT<br>TGGCGAAGCCAACAGAAAGTAGTGATAACGAAAGTAGTTACACACCCG<br>TTCAAGACAATAGAGCTCCAGATGAAAAAAAAAGGCTTCAAGATGGAA<br>GTCGGTCAATACATATTCGTGAAGTGCCCGAAAGTCTCAAAGTTGGAA<br>TGGCACCCATTCACTCTCACATCAGCGCCTGAAGAAGACTTTTTCTCC<br>ATTCATATTCGCATTGTGGGCGATTGGACGGAAGGGCTCTTTAACGCT<br>TGCGGGTGTGATAAACAAGAGTTTCAAGACGCATGGAAATTGCCTAAG<br>ATAGCAGTTGATGGCCCGTTCGGAACCGCCAGCGAAGATGTTTTCAGT<br>TACGAGGTCGTCATGCTCGTTGGTGCTGGAATCGGAGTTACTCCGTTT<br>GCTTCCATACTTAAGAGCGTCTGGTACAAATATTGTAATAATGCCACC<br>AATTTGAAACTCAAGAAGATTTACTTTTATTGGTTGTGTAGGGATACT<br>CACGCTTTCGAATGGTTCGCAGACCTTCTCCAGCTCCTTGAAAGCCAA<br>ATGCAGGAACGAAATAACGCAGGATTTTTGAGCTACAATATATACCTT<br>ACGGGTTGGGACGAATCTCAGGCTAATCATTTCGCGGTACACCATGAT<br>GAAGAAAAGGATGTTATAACGGGTTTGAAACAAAAAACACTCTATGGA<br>CGACCTAACTGGGATAATGAATTTAAAACAATCGCCAGCCAACATCCT<br>AACACCCGGATTGGAGTTTTCCTGTGCGGGCCAGAGGCACTCGCGGAG<br>ACGCTGAGTAAACAATCAATTAGCAACTCTGAGTCCGGGCCACGCGGG<br>GTGCATTTTATTTTTAACAAAGAGAACTTCTAG |

In various embodiments, the lentiviral vectors (LVs) described herein can have various "safety" features that can include, for example, the presence of an insulator (e.g., an FB insulator in the 3'LTR). Additionally, or alternatively, in certain embodiments, the HIV LTR has been substituted with an alternative promoter (e.g., a CMV) to yield a higher titer vector without the inclusion of the HIV TAT protein during packaging. Other strong promoters (e.g., RSV, and the like can also be used).

In various embodiments the lentiviral vectors described herein contain any one or more of the elements typically found in lentiviral vectors. Such elements include, but need not be limited to a ψ region vector genome packaging signal, a Rev Responsive Element (RRE), a polypurine tract (e.g., a central polypurine tract, a 3' polypurine tract, etc.), a post-translational regulatory element (e.g., a modified Woodchuck Post-transcriptional Regulatory Element (WPRE)), an insulator, and the like, e.g., as described below.

In various embodiments the vector is a SIN vector substantially incapable of reconstituting a wild-type lentivirus through recombination.

Figure 20:
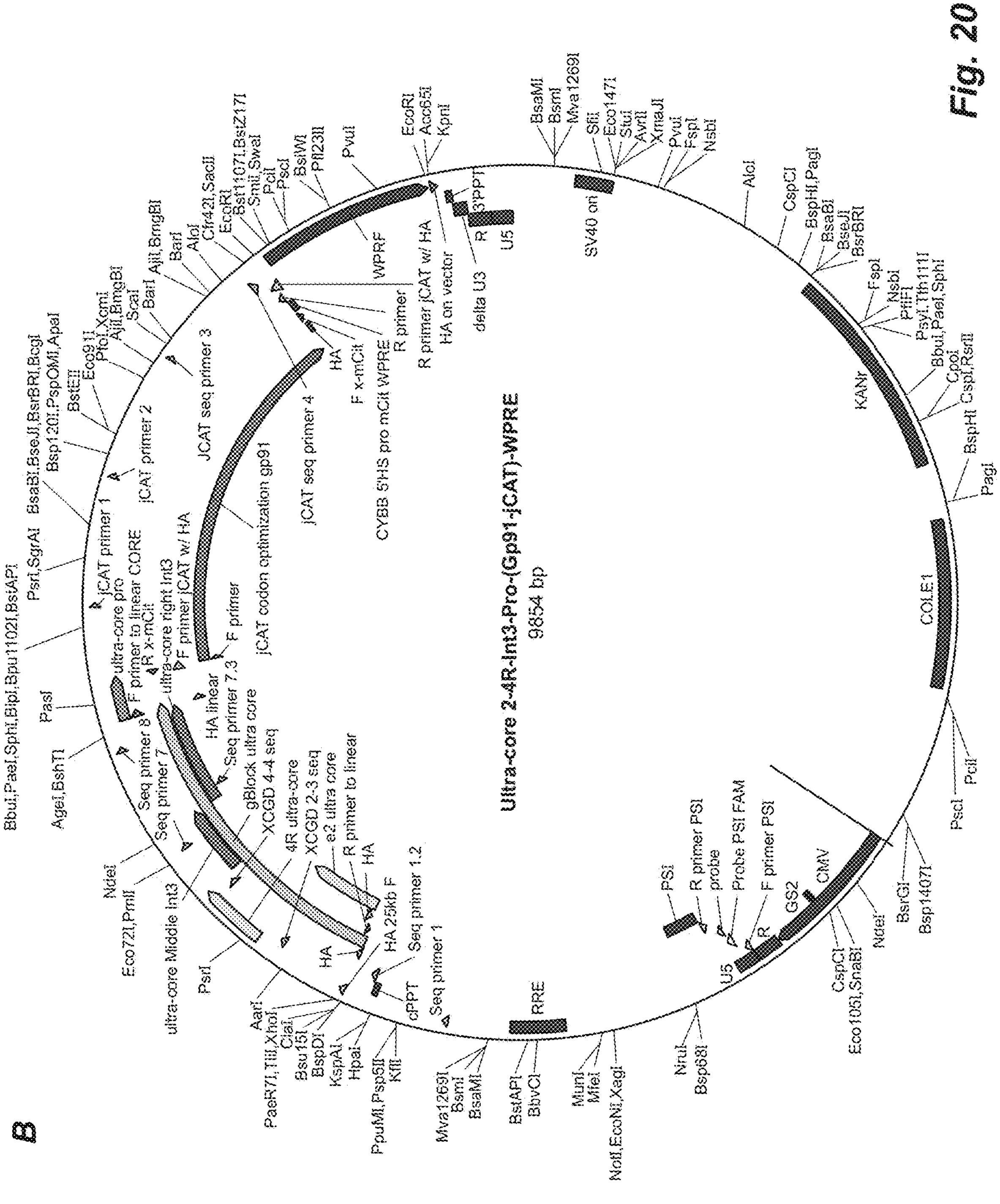
FIG. 20 panels A-B, illustrate one embodiment of an optimized lentiviral vector for treatment of X-CGD. Panel A schematically illustrates the elements of UC 2-4R-Int3-pro-coGp91$^{phox}$-WRPE. Panel B shows a "map" of the vector.
Figure 20:

In certain embodiments the vector comprises the features of "ultra core" (UC) 2-4R-Int3-Pro-(GP91-jcat)-WPRE shown in FIG. 20, panel A. In certain embodiments the vector comprises the features shown in the vector represented in FIG. 20, panel B. In certain embodiments the vector comprises the nucleotide sequence of ultra core (UC) 2-4R-Int3-Pro-(GP91-jcat)-WPRE (SEQ ID NO: 22).

In various embodiments the vector shows high expression in CD33+(bulk myeloid cells), and/or high expression in CD19+(B cells), high expression in CD66b+CD15+ CD11b+ CD16+(mature neutrophils), and/or low or no expression in CD3+(T cells). In various embodiments the vector shows high expression in CD33+(bulk myeloid cells), high expression in CD19+(B cells, high expression in CD66b+ CD15+ CD11b+ CD16+(mature neutrophils), and low or no expression in CD3+ T cells.

As shown above, in Example 1, the vectors described herein are effective to transduce cells at high titer and to also provide high levels of expression of $Gp91^{phox}$.

In view of these results, it is believed that LVs described herein, e.g., recombinant TAT-independent, SIN LVs that express a nucleic acid encoding a $Gp91^{phox}$ can be used to effectively treat X-linked chronic granulomatous disease (X-CGD) in subjects (e.g., human and non-human mammals). It is believed these vectors can be used for the modification of stem cells (e.g., hematopoietic stem and progenitor cells) that can be introduced into a subject in need thereof for the treatment of, e.g., subjects identified as having X-CGD. Moreover, it is believed that the resulting cells will produce enough of the transgenic $Gp91^{phox}$ protein to demonstrate significant improvement in subject health. It is also believed the vectors can be directly administered to a subject to achieve in vivo transduction of the target (e.g., hematopoietic stem or progenitor cells) and thereby also effect a treatment of subjects in need thereof.

As noted above, in various embodiments the LVs described herein can comprise various safety features. For example, the HIV LTR has been substituted with a CMV promoter to yield higher titer vector without the inclusion of the HIV TAT protein during packaging. In certain embodiments an insulator (e.g., the FB insulator) can be introduced into the 3'LTR for safety. The LVs are also constructed to provide efficient transduction and high titer.

It will be appreciated that the foregoing elements are illustrative and need not be limiting. In view of the teachings provided herein, suitable substitutions for these elements will be recognized by one of skill in the art and are contemplated within the scope of the teachings provided herein.

$GP91^{phox}$ Codon Optimization.

As noted above, in various embodiments the lentiviral vector can comprise a CYBB gene or cDNA. However, in certain embodiments the nucleic acid encoding $Gp91^{phox}$ is codon optimized. Numerous methods of codon optimization are known to those of skill in the art. One illustrative method is JCat (Java Codon Adaptation Tool). The jCAT tool adapts gene codon usage to most sequenced prokaryotes and various eukaryotic gene expression hosts. In contrast to many tools, JCat does not require the manual definition of highly expressed genes and is, therefore, a very rapid and easy method. Further options of JCat for codon adaptation include the avoidance of unwanted cleavage sites for restriction enzymes and Rho-independent transcription terminators. The output of JCat is both graphically and as Codon Adaptation Index (CAI) values given for the input sequence and the newly adapted sequence. JCat optimization is described by Grote et al. (2005) Nucleic Acids Res. 33(suppl 2): W526-W531) and a JCat tool is available online at www.jcat.de.

Another codon optimization tool is provided by GeneArt (from ThermoFisher Scientific®.

Still another codon optimization tool is IDT. The IDT codon optimization tool was developed to optimize a DNA or protein sequence from one organism for expression in another by reassigning codon usage based on the frequencies of each codon's usage in the new organism. For example, valine is encoded by 4 different codons (GUG, GUU, GUC, and GUA). In human cell lines, however, the GUG codon is preferentially used (46% use vs. 18, 24, and 12%, respectively). The codon optimization tool takes this information into account and assigns valine codons with those same frequencies. In addition, the tool algorithm eliminates codons with less than 10% frequency and re-normalizes the remaining frequencies to 100%. Moreover, the optimization tool reduces complexities that can interfere with manufacturing and downstream expression, such as repeats, hairpins, and extreme GC content. The IDT optimization tool is available from IDT (Integrated DNA Technologies, Coralville, Iowa) and can be found at ww.idtdna.com/CodonOpt.

Other codon optimization tools include, but are not limited to CodonW an open source software program that can be found at codonw.sourceforge.net, and the OptimumGene™ algorithm from GenScript.

In one embodiment, illustrated in Example 1, the codon optimized Gp91$^{phox}$, can be the sequence used in the current clinical candidate MSP-Gp91$^{phox}$-WPRE.

These codon optimizations are illustrative and non-limiting. Using the teaching provided here and in Example 1, the Gp91$^{phox}$ codon usage can readily be optimized for particular applications.

TAT-Independent and Self Inactivating Lentiviral Vectors.

To further improve safety, in various embodiments, the lentiviral vectors described herein comprise a TAT-independent, self-inactivating (SIN) configuration. Thus, in various embodiments it is desirable to employ in the LVs described herein an LTR region that has reduced promoter activity relative to wild-type LTR. Such constructs can be provided that are effectively "self-inactivating" (SIN) which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that that cellular coding sequences located adjacent to the vector integration site will be aberrantly expressed.

Furthermore, a SIN design reduces the possibility of interference between the LTR and the promoter that is driving the expression of the transgene. SIN LVs can often permit full activity of the internal promoter.

The SIN design increases the biosafety of the LVs. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus.

As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

In certain embodiments self-inactivation is achieved through the introduction of a deletion in the U3 region of the 3' LTR of the vector DNA, i.e., the DNA used to produce the vector RNA. During RT, this deletion is transferred to the 5' LTR of the proviral DNA. Typically, it is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function typically spread out over U3, R and U5. Accordingly, in certain embodiments, it is desirable to eliminate as many of the transcriptionally important motifs from the LTR as possible while sparing the polyadenylation determinants.

The SIN design is described in detail in Zufferey et al. (1998) *J Virol.* 72(12): 9873-9880, and in U.S. Pat. No. 5,994,136. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3'LTR may decrease polyadenylation of vector transcripts with adverse consequences both on the titer of the vector in producer cells and the transgene expression in target cells.

Additional SIN designs are described in U.S. Patent Publication No: 2003/0039636. As described therein, in certain embodiments, the lentiviral sequences removed from the LTRs are replaced with comparable sequences from a non-lentiviral retrovirus, thereby forming hybrid LTRs. In particular, the lentiviral R region within the LTR can be replaced in whole or in part by the R region from a non-lentiviral retrovirus. In certain embodiments, the lentiviral TAR sequence, a sequence which interacts with TAT protein to enhance viral replication, is removed, preferably in whole, from the R region. The TAR sequence is then replaced with a comparable portion of the R region from a non-lentiviral retrovirus, thereby forming a hybrid R region.

The LTRs can be further modified to remove and/or replace with non-lentiviral sequences all or a portion of the lentiviral U3 and U5 regions.

Accordingly, in certain embodiments, the SIN configuration provides a retroviral LTR comprising a hybrid lentiviral R region that lacks all or a portion of its TAR sequence, thereby eliminating any possible activation by TAT, wherein the TAR sequence or portion thereof is replaced by a comparable portion of the R region from a non-lentiviral retrovirus, thereby forming a hybrid R region. In a particular embodiment, the retroviral LTR comprises a hybrid R region, wherein the hybrid R region comprises a portion of the HIV R region (e.g., a portion comprising or consisting of the nucleotide sequence shown in SEQ ID NO: 10 in US 2003/0039636) lacking the TAR sequence, and a portion of the MoMSV R region (e.g., a portion comprising or consisting of the nucleotide sequence shown in SEQ ID NO: 9 in 2003/0039636) comparable to the TAR sequence lacking from the HIV R region. In another particular embodiment, the entire hybrid R region comprises or consists of the nucleotide sequence shown in SEQ ID NO: 11 in 2003/0039636.

Suitable lentiviruses from which the R region can be derived include, for example, HIV (HIV-1 and HIV-2), EIV, SIV and FIV. Suitable retroviruses from which non-lentiviral sequences can be derived include, for example, MoMSV, MoMLV, Friend, MSCV, RSV and Spumaviruses. In one illustrative embodiment, the lentivirus is HIV and the non-lentiviral retrovirus is MoMSV.

In another embodiment described in US 2003/0039636, the LTR comprising a hybrid R region is a left (5') LTR and further comprises a promoter sequence upstream from the hybrid R region. Preferred promoters are non-lentiviral in origin and include, for example, the U3 region from a non-lentiviral retrovirus (e.g., the MoMSV U3 region). In one particular embodiment, the U3 region comprises the nucleotide sequence shown in SEQ ID NO: 12 in US 2003/0039636. In another embodiment, the left (5') LTR further comprises a lentiviral U5 region downstream from the hybrid R region. In one embodiment, the U5 region is the HIV U5 region including the HIV att site necessary for genomic integration. In another embodiment, the U5 region comprises the nucleotide sequence shown in SEQ ID NO: 13 in US 2003/0039636. In yet another embodiment, the entire left (5') hybrid LTR comprises the nucleotide sequence shown in SEQ ID NO: 1 in US 2003/0039636.

In another illustrative embodiment, the LTR comprising a hybrid R region is a right (3') LTR and further comprises a modified (e.g., truncated) lentiviral U3 region upstream from the hybrid R region. The modified lentiviral U3 region can include the att sequence, but lack any sequences having promoter activity, thereby causing the vector to be SIN in that viral transcription cannot go beyond the first round of replication following chromosomal integration. In a particular embodiment, the modified lentiviral U3 region upstream from the hybrid R region consists of the 3' end of a lentiviral (e.g., HIV) U3 region up to and including the lentiviral U3 att site. In one embodiment, the U3 region comprises the nucleotide sequence shown in SEQ ID NO: 15 in US 2003/0039636. In another embodiment, the right (3') LTR further comprises a polyadenylation sequence downstream from the hybrid R region. In another embodiment, the polyadenylation sequence comprises the nucleotide sequence shown in SEQ ID NO: 16 in US 2003/0039636. In yet another embodiment, the entire right (5') LTR comprises the nucleotide sequence shown in SEQ ID NO: 2 or 17 of US 2003/0039636.

Thus, in the case of HIV based LV, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower.

It has also been demonstrated that the trans-acting function of Tat becomes dispensable if part of the upstream LTR in the transfer vector construct is replaced by constitutively active promoter sequences (see, e.g., Dull et al. (1998) J Virol. 72(11): 8463-8471. Furthermore, we show that the expression of rev in trans allows the production of high-titer HIV-derived vector stocks from a packaging construct which contains only gag and pol. This design makes the expression of the packaging functions conditional on complementation available only in producer cells. The resulting gene delivery system, conserves only three of the nine genes of HIV-1 and relies on four separate transcriptional units for the production of transducing particles.

In one embodiments illustrated in Example 1, the cassette expressing a nucleic acid encoding gp91$^{phox}$ a SIN vector with the CMV enhancer/promoter substituted in the 5' LTR.

It will be recognized that the CMV promoter typically provides a high level of non-tissue specific expression. Other promoters with similar constitutive activity include, but are not limited to the RSV promoter, and the SV40 promoter. Mammalian promoters such as the beta-actin promoter, ubiquitin C promoter, elongation factor 1α promoter, tubulin promoter, etc., may also be used.

The foregoing SIN configurations are illustrative and non-limiting. Numerous SIN configurations are known to those of skill in the art. As indicated above, in certain embodiments, the LTR transcription is reduced by about 95% to about 99%. In certain embodiments LTR may be rendered at least about 90%, at least about 91%, at least about 92%, at least about 93%, at least about 94%, at least about 95% at least about 96%, at least about 97%, at least about 98%, or at least about 99% transcriptionally inactive.

Insulator Element

In certain embodiments, to further enhance biosafety, insulators are inserted into the lentiviral vectors described herein. Insulators are DNA sequence elements present throughout the genome. They bind proteins that modify chromatin and alter regional gene expression. The placement of insulators in the vectors described herein offer various potential benefits including, inter alia: 1) Shielding of the vector from positional effect variegation of expression by flanking chromosomes (i.e., barrier activity); and 2) Shielding flanking chromosomes from insertional trans-activation of gene expression by the vector (enhancer blocking). Thus, insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Natl. Acad. Sci. USA,* 99: 16433; and Zhan et al. (2001) Hum. Genet., 109: 471). In the present context insulators may contribute to protecting lentivirus-expressed sequences from integration site effects, which may be mediated by cis-acting elements present in genomic DNA and lead to deregulated expression of transferred sequences. In various embodiments LVs are provided in which an insulator sequence is inserted into one or both LTRs or elsewhere in the region of the vector that integrates into the cellular genome.

The first and best characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) *EMBO J.* 18: 4035-4048). A 1.2-kb fragment containing the cHS4 element displays classic insulator activities, including the ability to block the interaction of globin gene promoters and enhancers in cell lines (Chung et al. (1993) *Cell,* 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) *Transgenic Res.,* 8: 223-235) from position effects. Much of this activity is contained in a 250-bp fragment. Within this stretch is a 49-bp cHS4 core (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

One illustrative and suitable insulator is FB (FII/BEAD-A), a 77 bp insulator element, that contains the minimal CTCF binding site enhancer-blocking components of the chicken β-globin 5' HS4 insulators and a homologous region from the human T-cell receptor alpha/delta blocking element alpha/delta I (BEAD-I) insulator described by Ramezani et al. (2008) *Stem Cell* 26: 3257-3266. The FB "synthetic" insulator has full enhancer blocking activity. This insulator is illustrative and non-limiting. Other suitable insulators may be used including, for example, the full-length chicken beta-globin HS4 or insulator sub-fragments thereof, the ankyrin gene insulator, and other synthetic insulator elements.

Packaging Signal.

In various embodiments the vectors described herein further comprise a packaging signal. A "packaging signal," "packaging sequence," or "PSI sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art. One illustrative, but non-limiting PSI is provided by SEQ ID NO:25.

Rev Responsive Element (RRE).

In certain embodiments the lentiviral vectors described herein comprise a Rev response element (RRE) to enhance nuclear export of unspliced RNA. RREs are well known to those of skill in the art. Illustrative RREs include, but are not limited to RREs such as that located at positions 7622-8459 in the HIV NL4-3 genome (Genbank accession number AF003887) as well as RREs from other strains of HIV or other retroviruses. Such sequences are readily available from Genbank or from the database with URL hiv-web.lanl-.gov/content/index. One illustrative, but non-limiting RRE is shown in SEQ ID NO:26).

PolyPurine Tract (cPPT, 3'PPT).

In various embodiments the lentiviral vectors described herein further include a polypurine tract (e.g., central polypurine tract (cPPT), 3' poplypurine tract (3'PPT)). Insertion of a fragment containing the 3'PPT (see, e.g., SEQ ID NO:28) or the central polypurine tract (cPPT) in lentiviral (e.g., HIV-1) vector constructs is known to enhance transduction efficiency.

Expression-Stimulating Posttranscriptional Regulatory Element (PRE)

In certain embodiments the lentiviral vectors (LVs) described herein may comprise any of a variety of posttranscriptional regulatory elements (PREs) whose presence within a transcript increases expression of the heterologous nucleic acid (e.g., gp91$^{phox}$) at the protein level. PREs may be particularly useful in certain embodiments, especially those that involve lentiviral constructs with modest promoters.

One type of PRE is an intron positioned within the expression cassette, which can stimulate gene expression. However, introns can be spliced out during the life cycle events of a lentivirus. Hence, if introns are used as PRE's they are typically placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is typically preferred as it contains an additional cis-acting element not found in the HPRE. This regulatory element is typically positioned within the vector so as to be included in the RNA transcript of the transgene, but outside of stop codon of the transgene translational unit.

The WPRE is characterized and described in U.S. Pat. No. 6,136,597. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7- to 10-fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE (see, e.g., SEQ ID NO:27) in a vector results in enhanced expression of transgenes.

Transduced Host Cells and Methods of cell transduction.

The recombinant lentiviral vectors (LV) and resulting virus described herein are capable of transferring a heterologous nucleic acid sequence (e.g., a nucleic acid encoding a gp91$^{phox}$) into a mammalian cell. In various embodiments, for delivery to cells, vectors described herein are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

In certain embodiments the vectors are introduced via transfection into a packaging cell line. The packaging cell line produces viral particles that contain the vector genome. Methods for transfection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with or without a dominant selectable marker, such as neomycin, DHFR, Glutamine synthetase, followed by selection in the presence of the appropriate drug and isolation of clones. In certain embodiments the selectable marker gene can be linked physically to the packaging genes in the construct.

Stable cell lines wherein the packaging functions are configured to be expressed by a suitable packaging cell are known (see, e.g., U.S. Pat. No. 5,686,279, which describes packaging cells). In general, for the production of virus particles, one may employ any cell that is compatible with the expression of lentiviral Gag and Pol genes, or any cell that can be engineered to support such expression. For example, producer cells such as 293T cells and HT1080 cells may be used.

The packaging cells with a lentiviral vector incorporated therein form producer cells. Producer cells are thus cells or cell-lines that can produce or release packaged infectious viral particles carrying the therapeutic gene of interest (e.g., a $Gp91^{phox}$). These cells can further be anchorage dependent which means that these cells will grow, survive, or maintain function optimally when attached to a surface such as glass or plastic. Some examples of anchorage dependent cell lines used as lentiviral vector packaging cell lines when the vector is replication competent are HeLa or 293 cells and PERC.6 cells.

Accordingly, in certain embodiments, methods are provided of delivering a gene to a cell which is then integrated into the genome of the cell, comprising contacting the cell with a virion containing a lentiviral vector described herein. The cell (e.g., in the form of tissue or an organ) can be contacted (e.g., infected) with the virion ex vivo and then delivered to a subject (e.g., a mammal, animal or human) in which the gene (e.g., a nucleic acid encoding $gp91^{phox}$) will be expressed. In various embodiments the cell can be autologous to the subject (i.e., from the subject) or it can be non-autologous (i.e., allogeneic or xenogenic) to the subject. Moreover, because the vectors described herein are capable of being delivered to both dividing and non-dividing cells, the cells can be from a wide variety including, for example, bone marrow cells, mesenchymal stem cells (e.g., obtained from adipose tissue), and other primary cells derived from human and animal sources. Alternatively, the virion can be directly administered in vivo to a subject or a localized area of a subject (e.g., bone marrow).

In certain embodiments, the lentivectors described herein will be particularly useful in the transduction of human hematopoietic progenitor cells or a hematopoietic stem cells, obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ hematopoietic stem and progenitor cells.

Gene Therapy.

In still other embodiments, methods are provided for transducing a human hematopoietic stem cell. In certain embodiments the methods involve contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., an X-CGD patient, using methods well known to those of skill in the art and transduced as noted above. The transduced stem cells are then reintroduced into the same or a different human.

Stem Cell/Progenitor Cell Gene Therapy.

In various embodiments the lentivectors described herein are particularly useful for the transduction of human hematopoietic progenitor cells or hematopoietic stem cells (HSCs), obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ hematopoietic stem and progenitor cells.

When cells, for instance CD34+ cells, dendritic cells, peripheral blood cells or tumor cells are transduced ex vivo, the vector particles are incubated with the cells using a dose generally in the order of between 1 to 50 multiplicities of infection (MOI) which also corresponds to $1\times10^5$ to $50\times10^5$ transducing units of the viral vector per $10^5$ cells. This can include amounts of vector corresponding to 1, 2, 3, 4, 5, 6, 7, 8, 9, 10, 15, 20, 25, 30, 35, 40, 45, and 50 MOI. Typically, the amount of vector may be expressed in terms of HT-29 transducing units (TU).

In certain embodiments cell-based therapies involve providing stem cells and/or hematopoietic precursors, transduce the cells with the lentivirus encoding, e.g., a $Gp91^{phox}$, and then introduce the transformed cells into a subject in need thereof (e.g., a subject with a mutation in the CYBB gene).

In certain embodiments the methods involve isolating population of cells, e.g., stem cells from a subject, optionally expand the cells in tissue culture, and administer the lentiviral vector whose presence within a cell results in production of a $Gp91^{phox}$ in the cells in vitro. The cells are then returned to the subject, where, for example, they may provide a population of phagocytic cells that produce the $Gp91^{phox}$.

In some illustrative, but non-limiting, embodiments, a population of cells, which may be cells from a cell line or from an individual other than the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

Where stem cells are to be used, it will be recognized that such cells can be derived from a number of sources including bone marrow (BM), cord blood (CB), mobilized peripheral blood stem cells (mPBSC), and the like. In certain embodiments the use of induced pluripotent stem cells (IPSCs) is contemplated. Methods of isolating hematopoietic stem cells (HSCs), transducing such cells and introducing them into a mammalian subject are well known to those of skill in the art.

Figure 19:
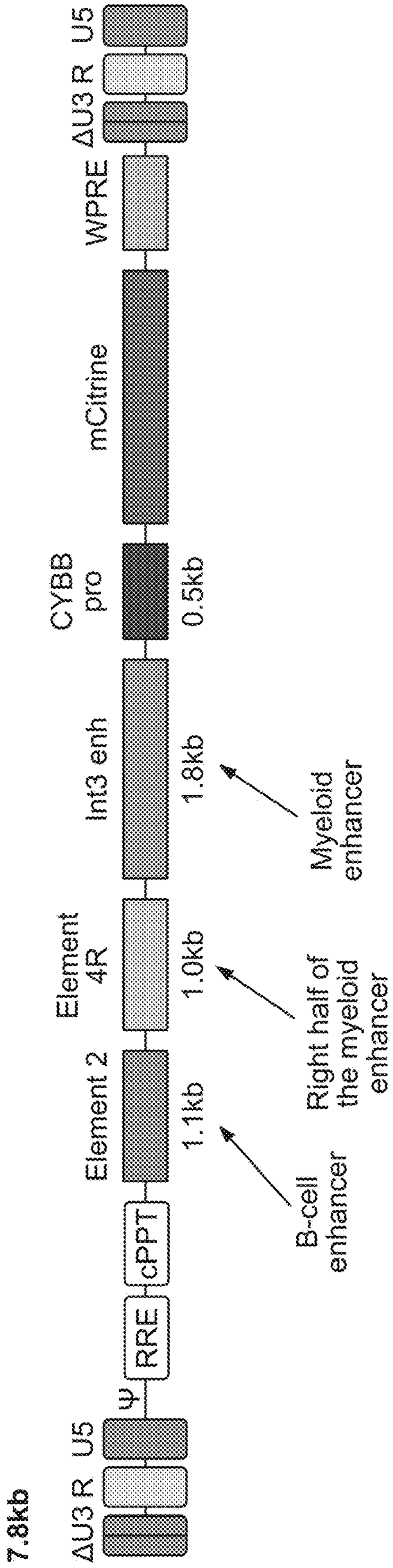
FIG. 19 illustrates one embodiment of a lentiviral vector for treatment of X-CGD. For use in a treatment the mCit reporter would be replaced with a nucleic acid sequence encoding a Gp91$^{phox}$, e.g., as described herein.

In certain embodiments a lentiviral vector described herein (see, e.g., FIG. 19) is used in stem cell gene therapy for X-CDG by introducing a nucleic acid that encodes $Gp91^{phox}$ the into the bone marrow stem cells of patients with X-CGD followed by autologous transplantation.

Direct Introduction of Vector.

In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include inhalation, parenteral, and transmucosal.

In various embodiments pharmaceutical compositions can include an LV in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral described herein and/or other agents to be administered together the vector, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Suitable materials can also be obtained commercially from Alza Corporation and Nova Pharmaceuticals, Inc. Liposomes can also be used as pharmaceutically acceptable carriers. These can be prepared according to methods known to those skilled in the art, for example, as described in U.S. Pat. No. 4,522,811. In some embodiments the composition is targeted to particular cell types or to cells that are infected by a virus. For example, compositions can be targeted using monoclonal antibodies to cell surface markers, e.g., endogenous markers or viral antigens expressed on the surface of infected cells.

It is advantageous to formulate compositions in dosage unit form for ease of administration and uniformity of dosage. Dosage unit form as used herein refers to physically discrete units suited as unitary dosages for the subject to be treated; each unit comprising a predetermined quantity of a LV calculated to produce the desired therapeutic effect in association with a pharmaceutical carrier.

A unit dose need not be administered as a single injection but may comprise continuous infusion over a set period of time. Unit dose of the LV described herein may conveniently be described in terms of transducing units (T.U.) of lentivector, as defined by titering the vector on a cell line such as HeLa or 293. In certain embodiments unit doses can range from $10^3$, $10^4$, $10^5$, $10^6$, $\mathbf{10^7}$, $10^8$, $\mathbf{10^9}$, $10^{10}$, $\mathbf{10^{11}}$, $\mathbf{10^{12}}$, $\mathbf{10^{13}}$ T.U. and higher.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. It may be necessary to administer the therapeutic composition on an indefinite basis. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a LV can include a single treatment or, in many cases, can include a series of treatments.

Illustrative, but non-limiting, doses for administration of gene therapy vectors and methods for determining suitable doses are known in the art. It is furthermore understood that appropriate doses of a LV may depend upon the particular recipient and the mode of administration. The appropriate dose level for any particular subject may depend upon a variety of factors including the age, body weight, general health, gender, and diet of the subject, the time of administration, the route of administration, the rate: of excretion, other administered therapeutic agents, and the like.

In certain embodiments lentiviral gene therapy vectors described herein can be delivered to a subject by, for example, intravenous injection, local administration, or by stereotactic injection (see, e.g., Chen et al. (1994) *Proc. Natl. Acad. Sci. USA,* 91: 3054). In certain embodiments vectors may be delivered orally or inhalationally and may be encapsulated or otherwise manipulated to protect them from degradation, enhance uptake into tissues or cells, etc. Pharmaceutical preparations can include a LV in an acceptable diluent, or can comprise a slow release matrix in which a LV is imbedded. Alternatively or additionally, where a vector can be produced intact from recombinant cells, as is the case for retroviral or lentiviral vectors as described herein, a pharmaceutical preparation can include one or more cells which produce vectors. Pharmaceutical compositions comprising a LV described herein can be included in a container, pack, or dispenser, optionally together with instructions for administration.

The foregoing compositions, methods and uses are intended to be illustrative and not limiting. Using the teachings provided herein other variations on the compositions, methods and uses will be readily available to one of skill in the art.

Example 1

Development of Lentiviral Vectors for Treatment of X-CGD

This example describes the development of novel lentiviral vectors for the treatment of X-linked Chronic Granulomatous Disease (X-CGD). In particular, we described the development of vector(s) that show higher expression levels than the current lentiviral vector undergoing clinical trials for X-CGD (pChim-CYBB, a.k.a. MSP-Gp91$^{phox}$-WPRE, see, e.g., Santilli et al. (2011) *Mol. Therapy.,* 19(1): 122-122). This lentiviral vector uses a chimeric myeloid-specific promoter (MSP) and chronically under-expresses in the mature human neutrophil population and fails to recapitulate the lineage specific expression pattern of the native CYBB gene. In contrast, the vectors described in this example possesses strict lineage and stage specific expression that mimics the expression pattern of the native CYBB gene (see, e.g., FIG. 1).

We have implemented a bioinformatics approach to elucidate the elements which regulate the endogenous CYBB gene in the human genome. The native CYBB topologically associated domain (TAD) comprises a 600 kb window spanning 100 kb upstream to 500 kb downstream of the CYBB gene. This CYBB TAD thus provides a 600,000 base pair window in the human genome to properly regulate the gene.

We attempted to elucidate the functional enhancer elements within the 600,000 base pair window and package the vital elements in a lentiviral vector of less than 9,000 base pairs. Using a bioinformatics approach, fifteen putative endogenous elements were identified within the native CYBB topologically associated domain (TAD).

Figure 2:
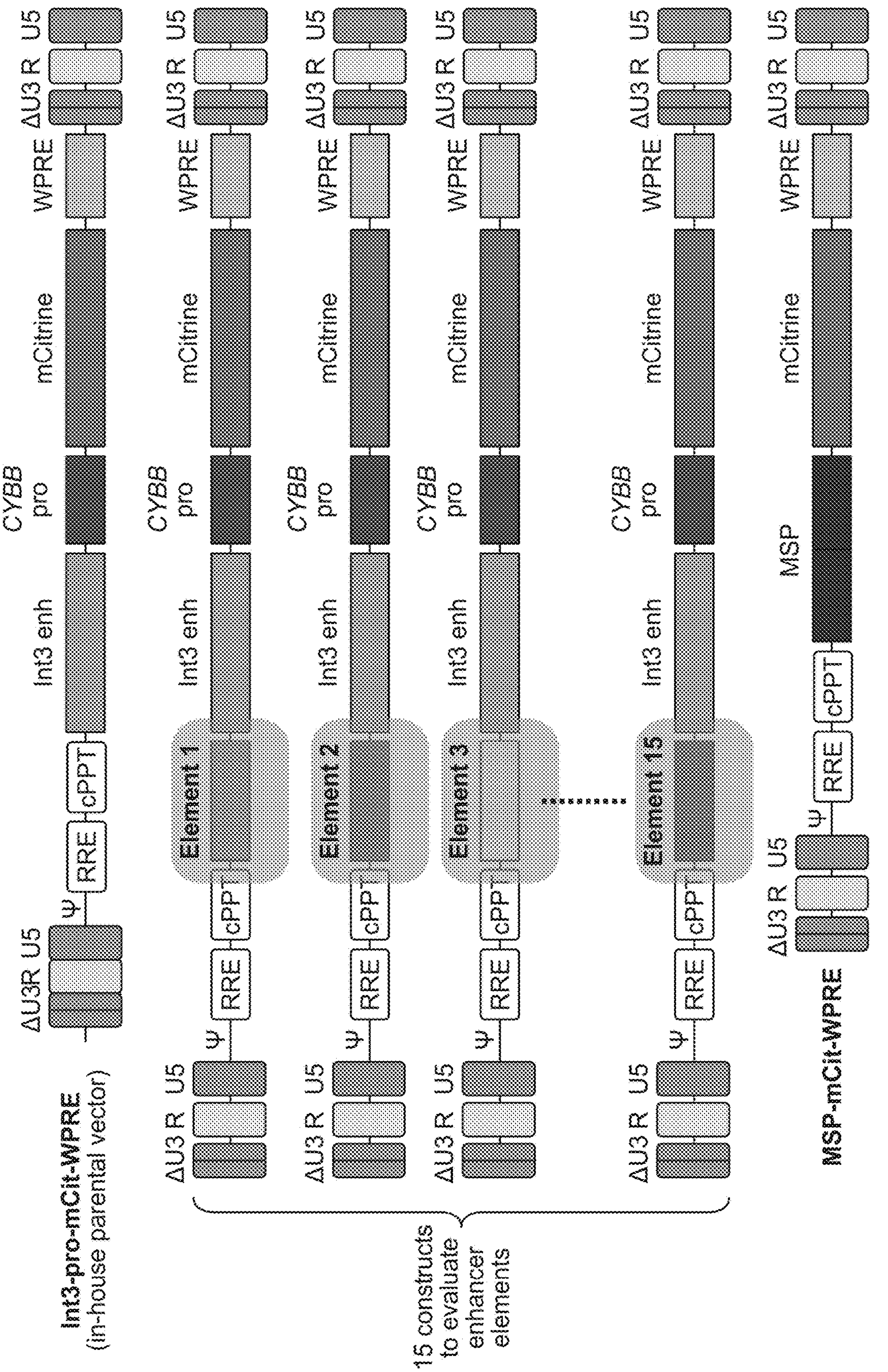
FIG. 2 illustrates constructs used to probe enhancer activity.

In order to experimentally identify the critical enhancer elements that regulate the CYBB gene, each putative enhancer element was cloned upstream of the endogenous CYBB promoter to drive expression of a reporter gene (mCitrine) (see, e.g., FIG. 2). In order to elucidate the function of each putative enhancer element, we assayed the activity of each of the vectors in cord blood (CB) CD34+ differentiated mature neutrophils and monocytes as well as RAMOS cells (B-lymphocyte cell line) which are 3 on-target cell lineages. All of the vectors were compared to the MSP-mCit-WPRE construct.

Figure 3:
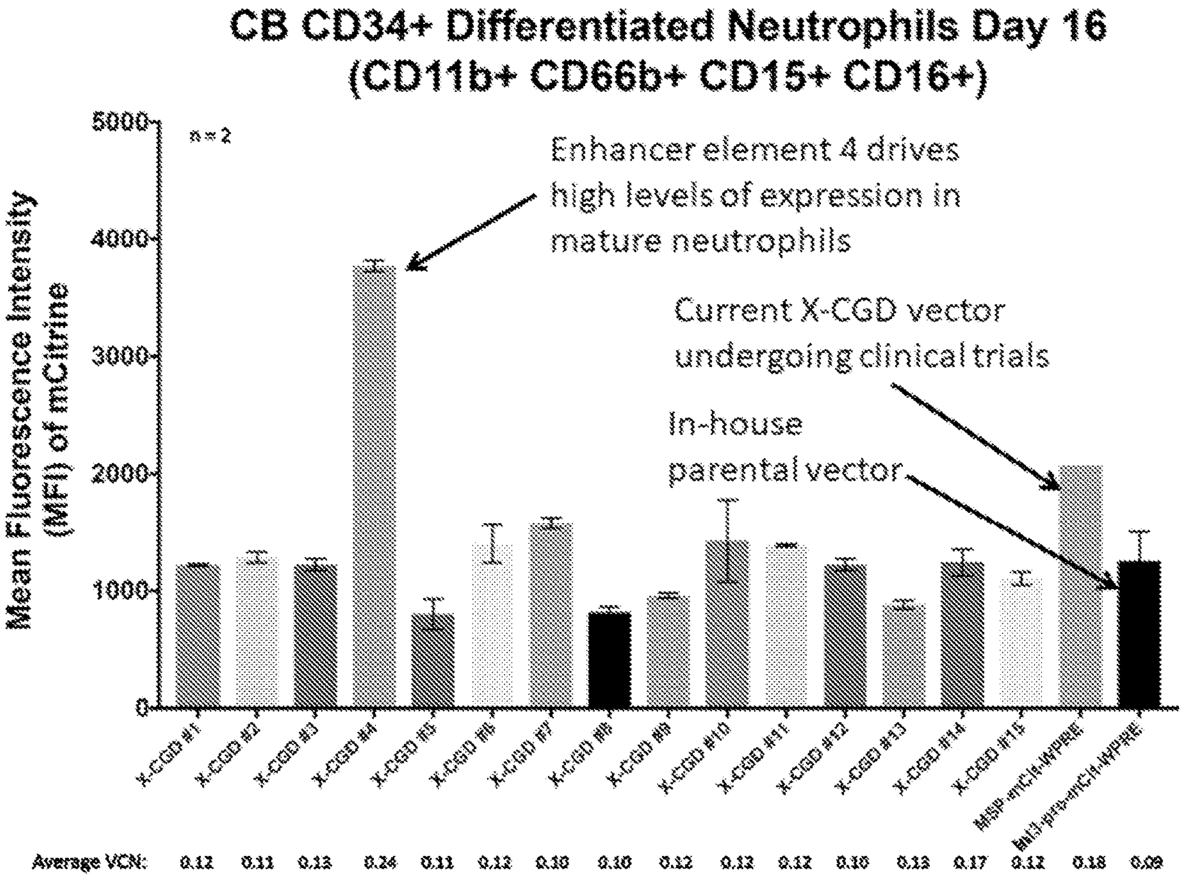
FIG. 3 expression of enhancer constructs in CB CD34+ differentiated neutrophils day 16 (CD11b+ CD66b+ CD15+ CD16+).
Figure 4:
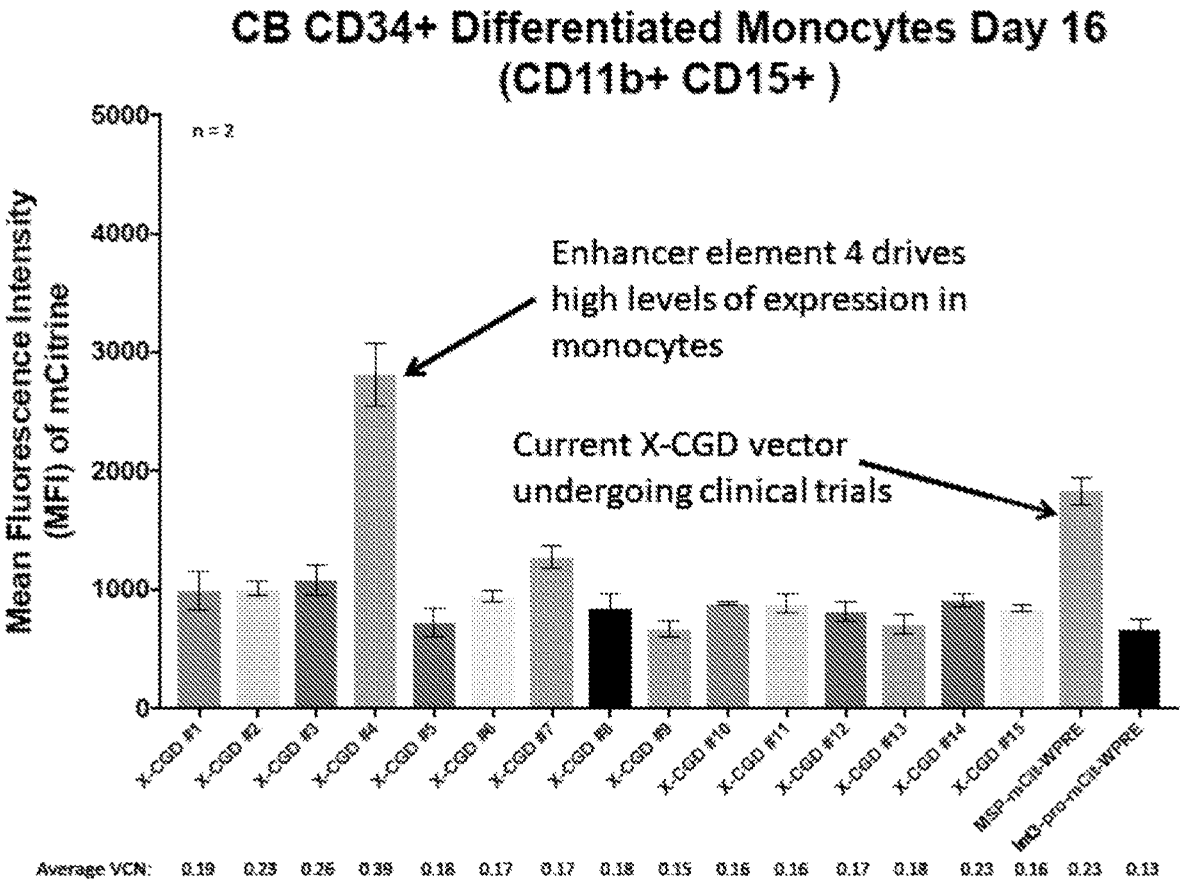
FIG. 4 expression of enhancer constructs in CB CD34+ differentiated monocytes day 16 (CD11b+ CD15+).

As shown in FIG. 3, enhancer element 4 drives high levels of expression in mature neutrophils. Additionally, the expression level is significantly higher than that obtained using the current X-CGD vector undergoing clinical trials. Similarly, as shown in FIG. 4 enhancer element 4 drives high levels of expression in monocytes as well, and again the expression levels are significantly higher than that obtained using the current X-CGD vector undergoing clinical trials.

Figure 5:
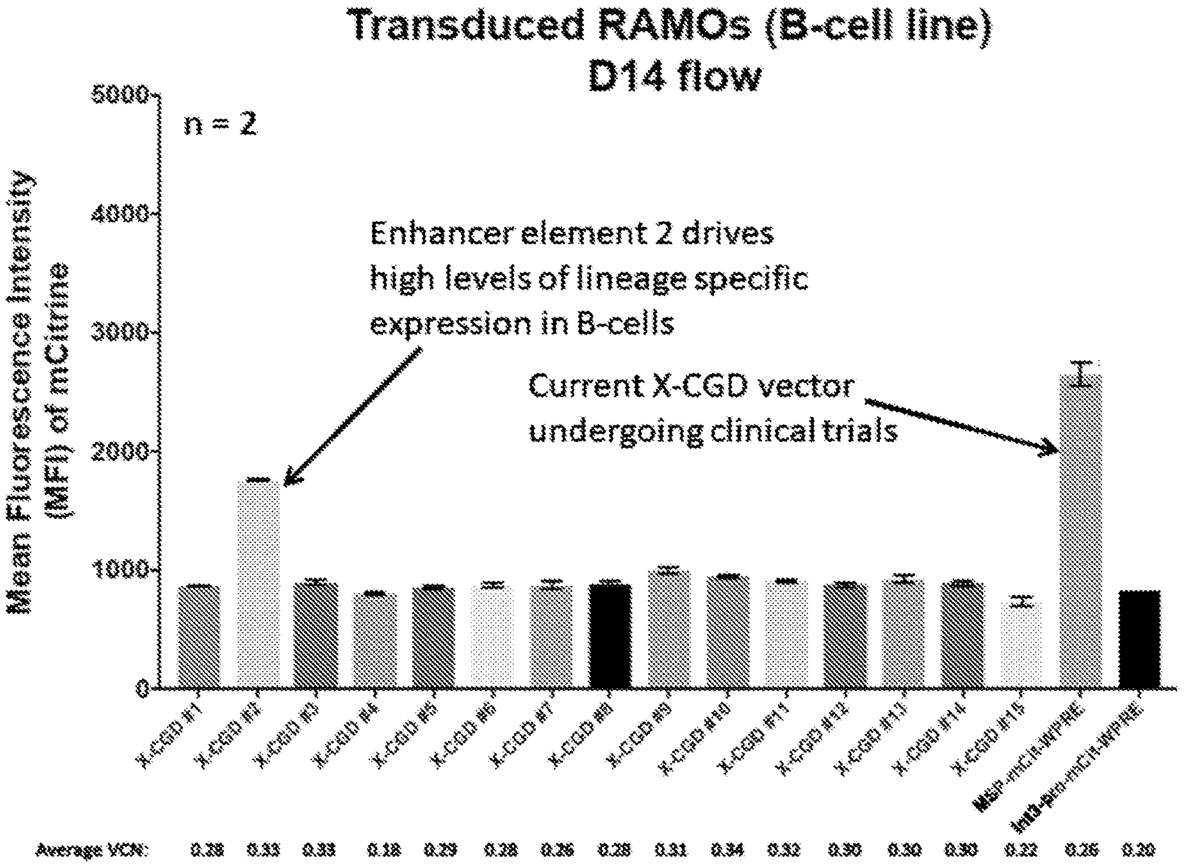
FIG. 5 shows expression of enhancer constructs in transduced RAMOs (B-cell line) D14 flow.
Figure 6:
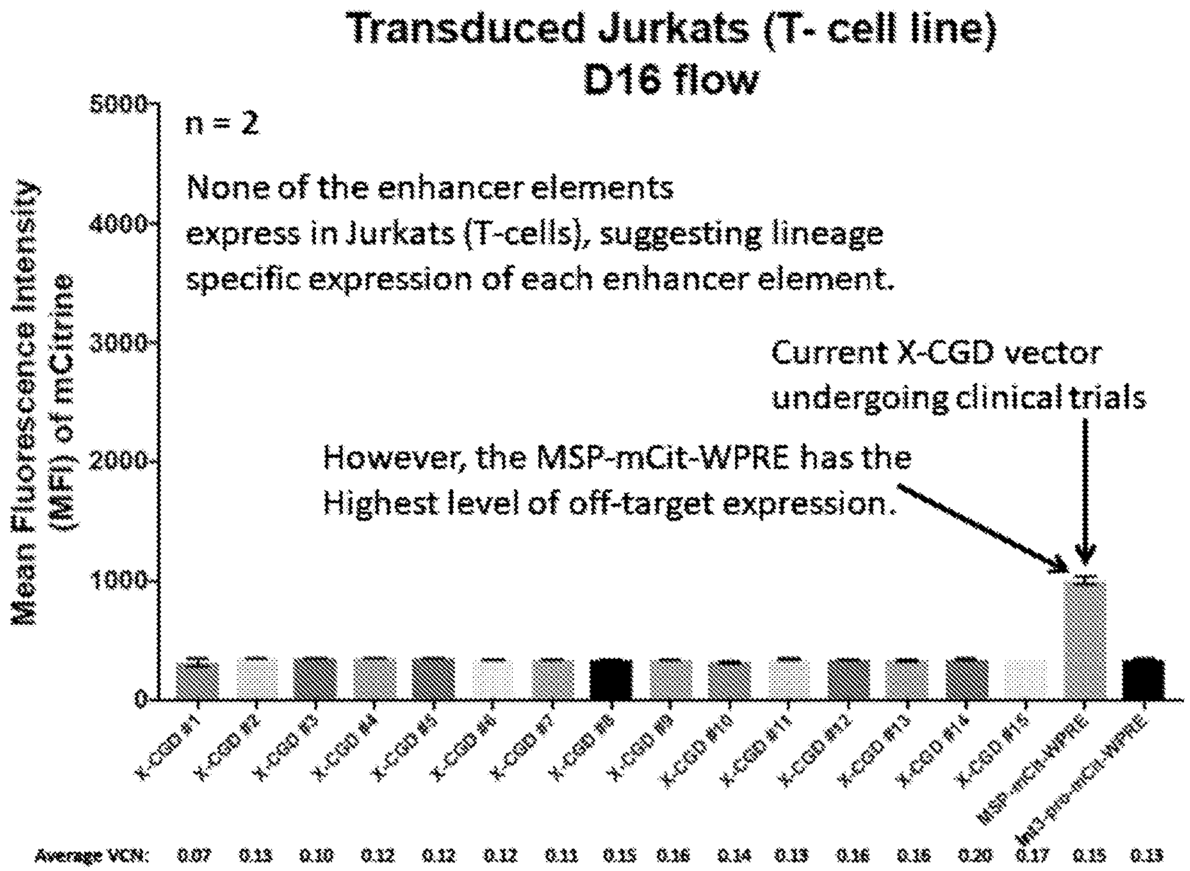
FIG. 6 shows expression of enhancer constructs in transduced Jurkats (T-cell line) D16 flow.

FIG. 5 shows that enhancer element 2 drives high levels of lineage specific expression in B-cells. None of the enhancer elements express in Jurkats (T-cells), suggesting lineage specific expression of each enhancer element (see, FIG. 6). In contrast, the MSP-mCit-WPRE construct showed the highest level of off-target expression.

Thus, it appears that enhancer element 4 confers increased lineage specific expression in mature neutrophils and monocytes and shows 2 fold higher expression than the MSP-mCit-WPRE vector. No enhancer element 4 driven expression was observed in T-cells (Jurkats) or in B-cells (RAMOs). Enhancer element 2 appears to confer increased lineage specific expression in B-cells (RAMOs). No enhancer element 2 driven expression was observed in neutrophils, monocytes or T-cells.

It was thus determined to incorporate enhancer elements 2 and 4 into a lentiviral vector to design a vector possessing on-target lineage specific expression in neutrophils, monocytes and B-cells. We note that enhancer element 4 is made of two distinct enhancer modules (4L and 4R) and these were evaluated to determine if one of these elements could be eliminated to decrease the size of the vector.

Accordingly, five new vectors were produced for evaluation. These were 4L-Int3-pro-mCit-WPRE, 4R-Int3-pro-mCit-WPRE, 2+4L-Int3-pro-mCit-WPRE, 2+4R-Int3-pro-mCit-WPRE, and 2+4-Int3-pro-mCit-WPRE. These new vectors were evaluated in in CB CD34+ differentiated neutrophils and monocytes and in RAMOs and Jurkats.

Figure 7:
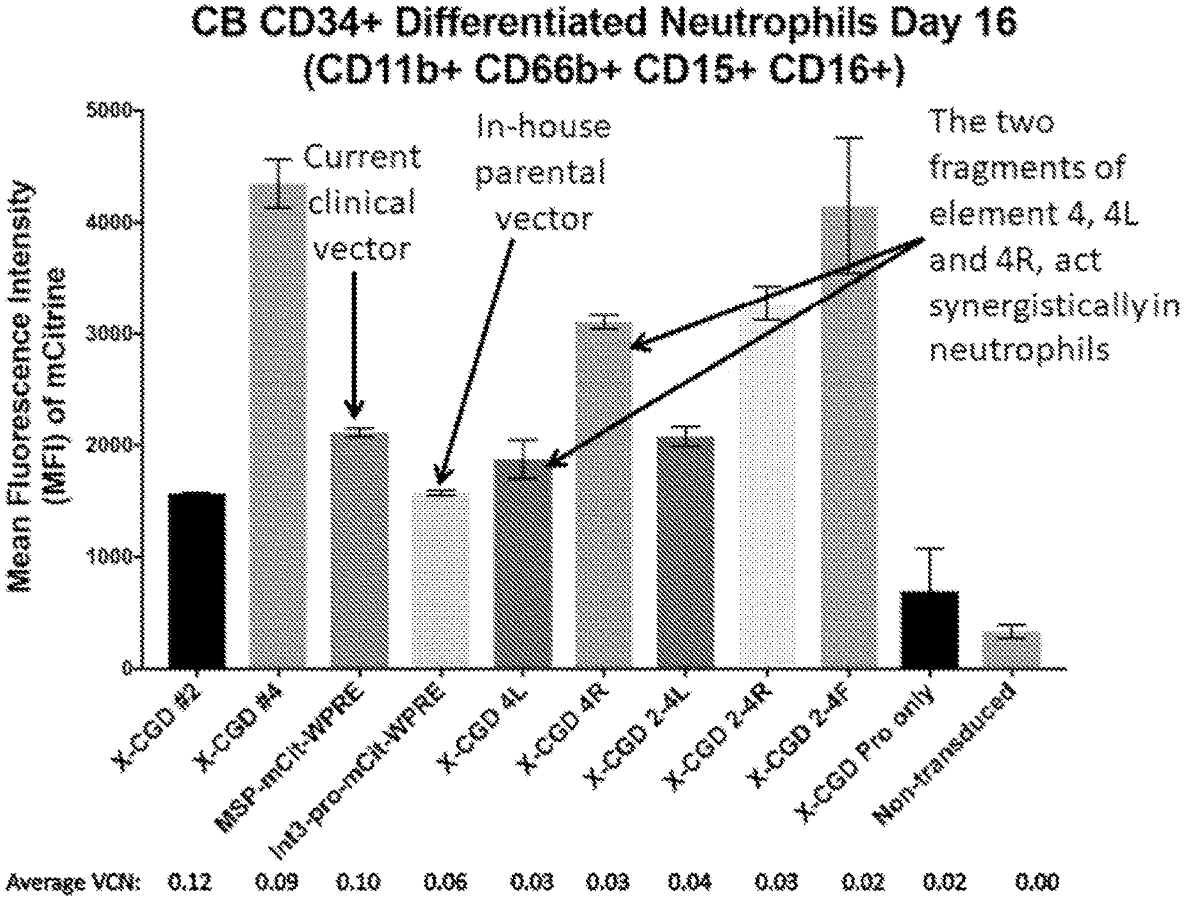
FIG. 7 shows expression of enhancer constructs in CB CD34+ differentiated Neutrophils Day 16 (CD11b+ CD66b+ CD15+ CD16+).
Figure 8:
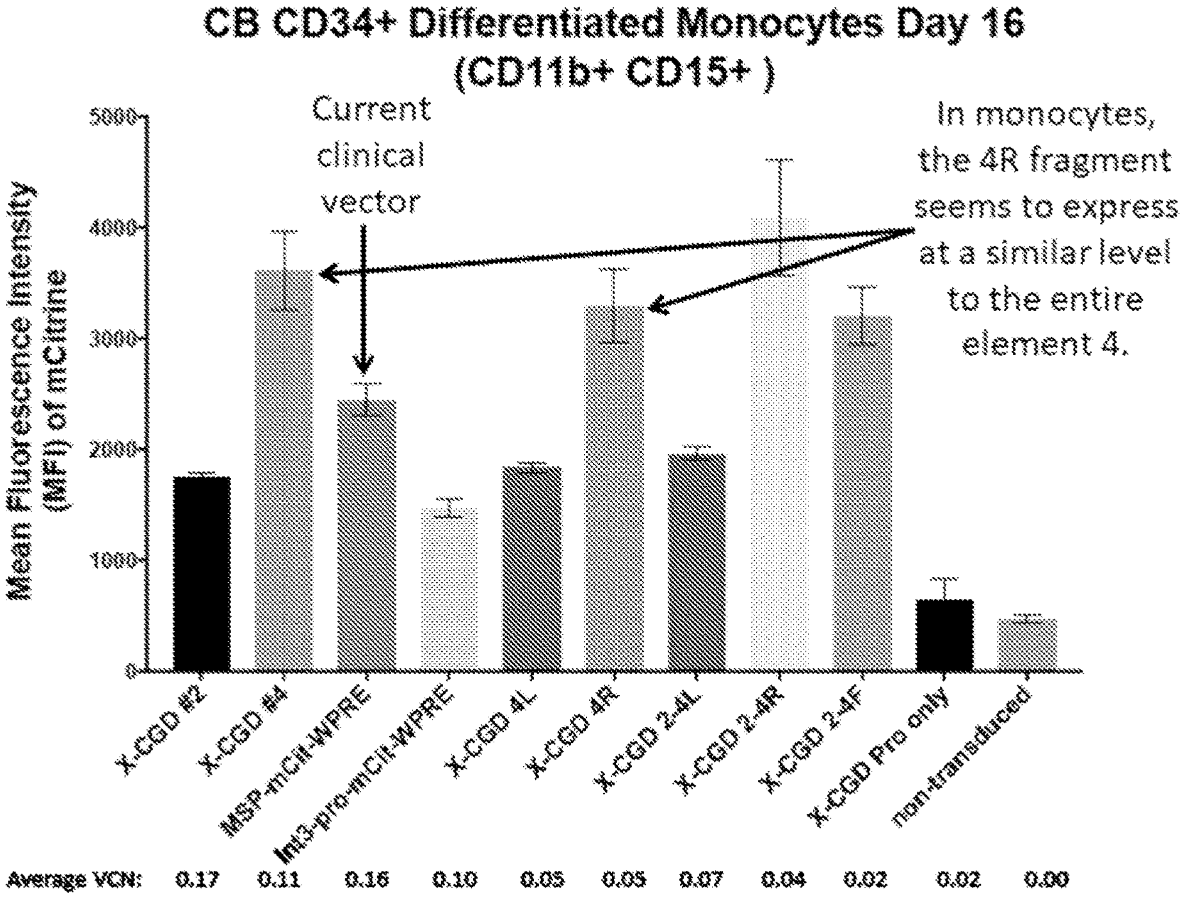
FIG. 8 shows expression of enhancer constructs in CB CD34+ differentiated Monocytes Day 16 (CD11b+ CD15+).
Figure 9:
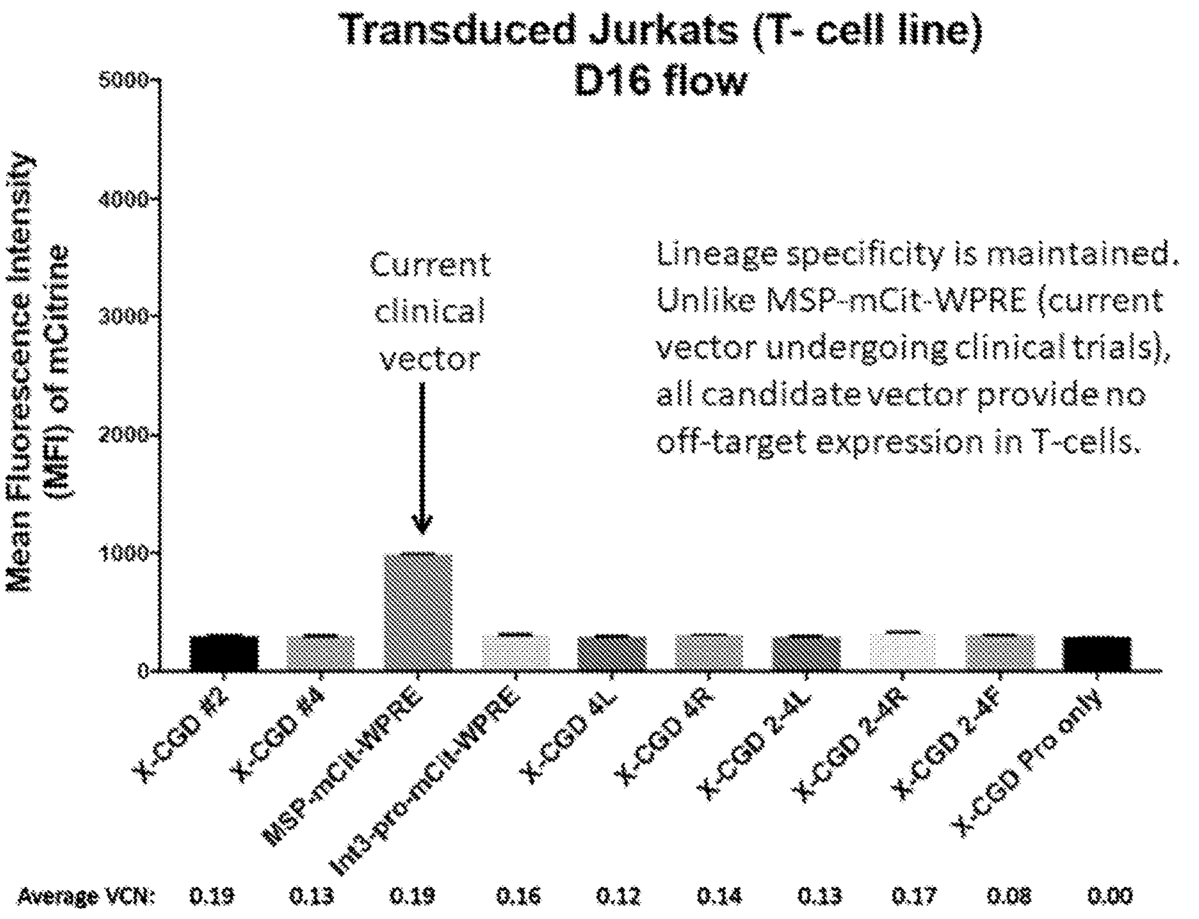
FIG. 9 shows expression of enhancer constructs in transduced Jurkats (T-cell line) D16 flow.
Figure 10:
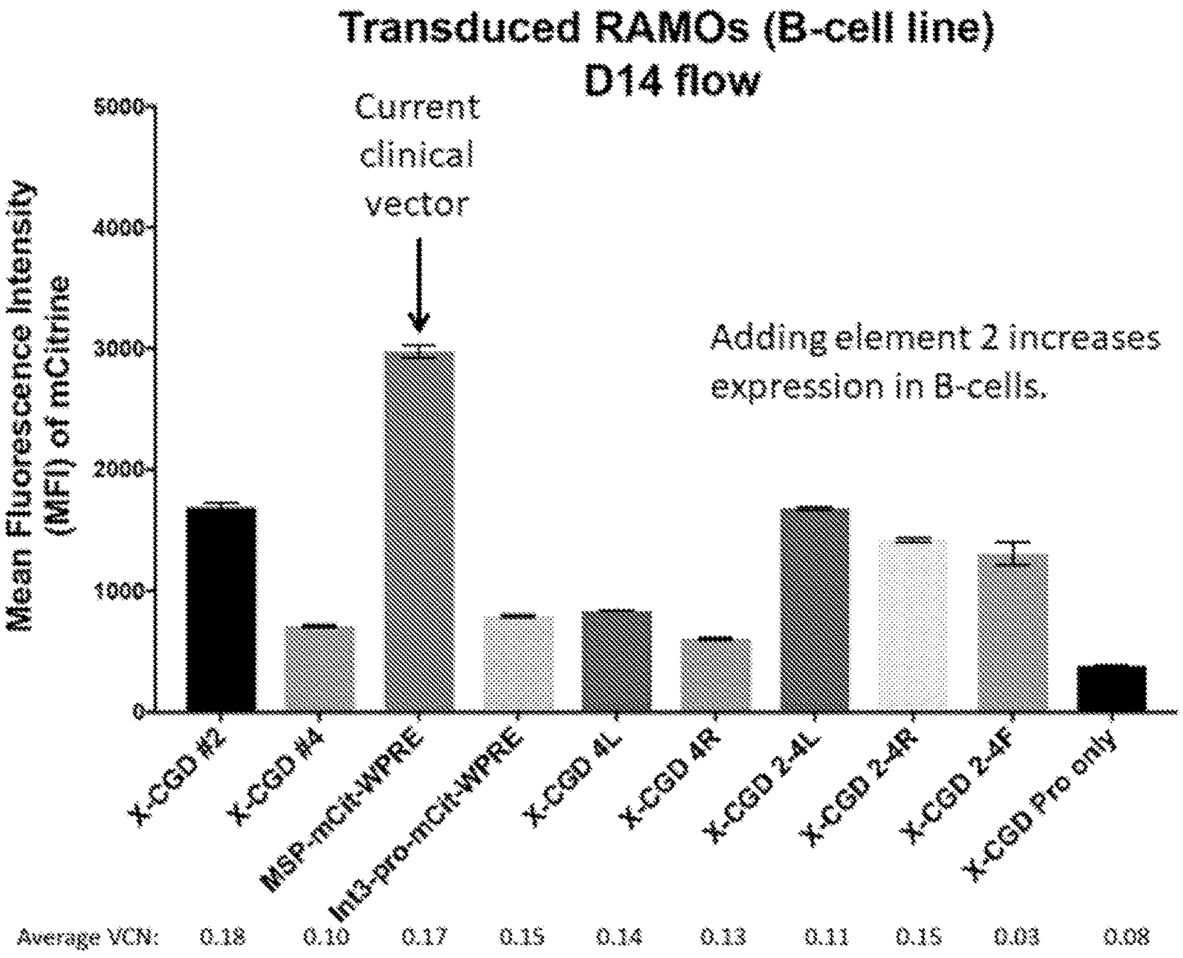
FIG. 10 shows expression of enhancer constructs in transduced RAMOs (B-cell line) D14 flow.

As shown in FIG. 7, the two fragments of enhancer element 4, 4L and 4R, act synergistically in neutrophils. However, element 4R alone still has higher expression than the MSP vector (current vector undergoing clinical trials). In monocytes, the 4R fragment seems to express at a similar level to the entire element 4 (see, FIG. 8). Lineage specificity was maintained (see, FIG. 9). Unlike MSP-mCit-WPRE (current vector undergoing clinical trials), all candidate vectors provided no off-target expression in T-cells. Additionally, incorporation of enhancer element 2 appears to increase expression in B cells (see, FIG. 10).

In view of these results, we conclude that the right half of element 4 (4R) seems to be the key contributor to lineage specific enhancer activity in neutrophils and monocytes. However, 4L and 4R seem to have a synergistic increase in expression when combined together in neutrophils and an additive effect when combined together in monocytes. Element 2 when combined with either of the myeloid enhancer elements 4, 4L or 4R remains a B-cell enhancer and is inert in the myeloid lineage. The vector 2-4R-Int3-pro-mCit-WPRE expresses 1.6 fold higher than MSP-mCit-WPRE in CB CD34+ differentiated neutrophils and monocytes. However it has 50% of the expression of MSP-mCit-WPRE in RAMO cells (B-cell lineage), but this may be a sufficient amount of expression to be therapeutic.

The 2-4Full-Int3-pro-mCit-WPRE expresses 2 fold and 1.6 fold higher than MSP-mCit-WPRE in neutrophils and monocytes, respectively.

Figure 11:
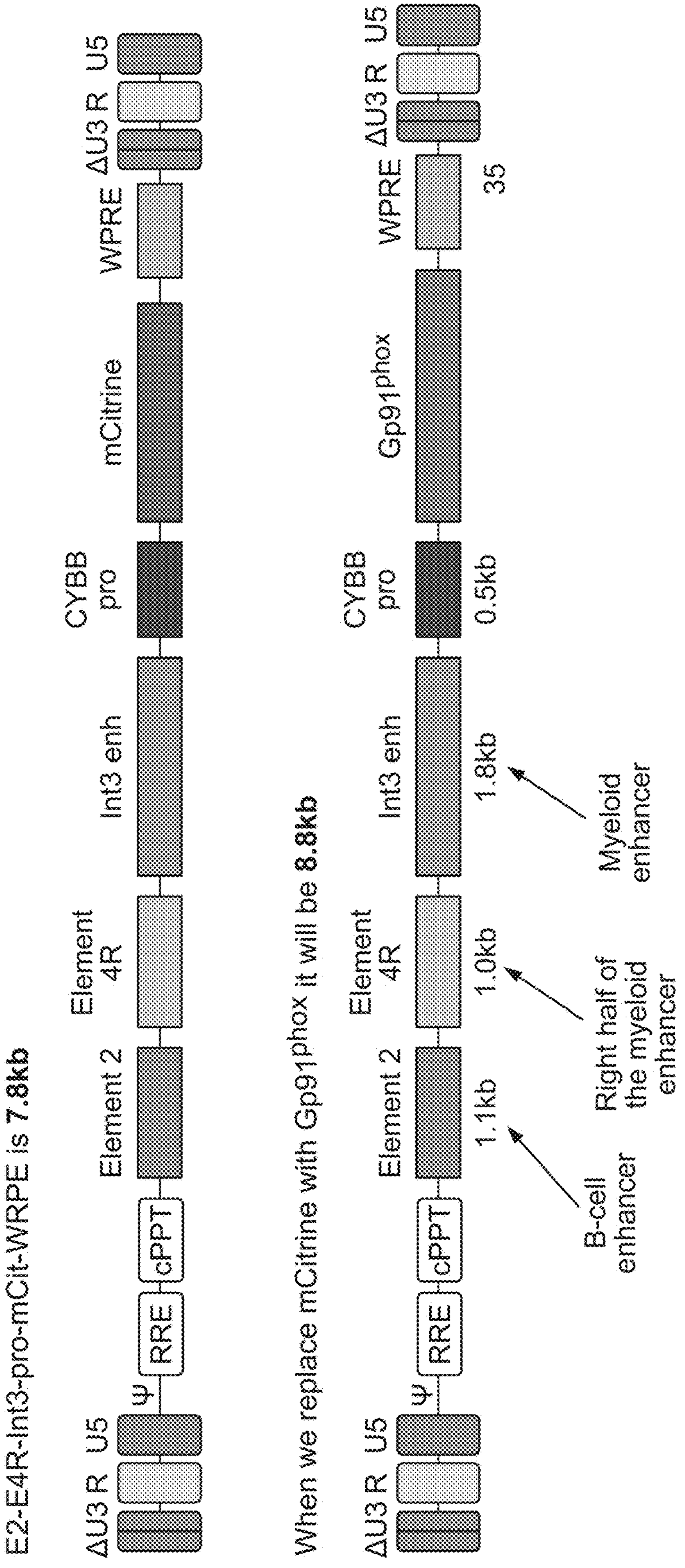
FIG. 11 shows structure of E2-E4R-Int3-pro-mCit-WPRE vector (top) and the same vector where mCitrine is replaced with nucleic acid encoding Gp91$^{phox}$ (bottom).

One X-CGD vector candidate of particular interest is 2-4R-Int3-pro-mCit-WPRE in which mCit can be replaced with a nucleic acid encoding Gp91$^{phox}$ (see e.g., FIG. 11) and which achieves the goal of possessing lineage specific expression, recapitulating the expression pattern of the native CYBB gene, and also expressing higher than the MSP-mCit-WPRE in mature neutrophils and monocytes.

Another goal is to decrease the size of vector while maintaining expression. In certain embodiments designed deletions can make the "core" and "ultra-core" variants. Modifications to make vectors of 7.6 kb and 5.9 kb respectively (w/Gp91$^{phox}$ in ORF). A secondary goal is to shrink the vector while increasing expression. In certain embodiments this can involve adding the "extra 4L core" and/or "extra 2" to the core and ultra core variants. Additionally, different codon optimizations of Gp91$^{phox}$ can be utilized to replace mCitrine in the open reading frame (ORF).

Full-length element 2 comprises 1092 base pairs. A 200 bp deletion was made to generate the 892 bp "core" variant (see, e.g., Table 1, SEQ ID NO:5). A 745 bp deletion was made to generate the 347 bp enhancer element 2 "ultra core" variant (see, e.g., Table 1, SEQ ID NO:6).

Similarly, full length element 4R comprises 995 bp and a 496 bp deletion was made to generate the 500 bp enhancer element 4R "core" variant (see, e.g., Table 1, SEQ ID NO:10). A 741 bp deletion was made to generate the 254 bp element 4R enhancer "ultra core" variant (see, e.g., Table 1, SEQ ID NO:11).

Similarly, a 242 bp deletion was made to the intron 3 enhancer (1778 bp) to generate a 1536 bp intron 3 enhancer "core" variant and a 1058 bp deletion was made to generate the 720 bp intron 3 enhancer "ultra core" fragment which comprises a middle fragment (see, e.g., Table 1, SEQ ID NO:15) and a right fragment (see, e.g., Table 1, SEQ ID NO:16).

A 240 bp deletion was made to the 507 bp full length CYBB endogenous promoter (see, e.g., Table 1, SEQ ID NO:1) to generate a 267 bp CYBB promoter "core" fragment (SEQ ID NO:2) and a 337 bp deletion was made to generate a minimal CYBB promoter "CYBB ultra core promoter" (see, e.g., Table 1, SEQ ID NO:3).

By making the "core" and "ultra-core" deletions, the vector size decreases by 1182 bp and 2882 bp, respectively as shown in Table 2.

TABLE 2

Size of "core" and "ultra core" vector variants.

| | |
|---|---|
| Original: | 7.8 kb w/mCit and 8.8 kb w/Gp91$^{phox}$; |
| Core: | 6.6 kb w/mCit and 7.6 kb w/Gp91$^{phox}$; |
| Ultra-core: | 4.9 kb w/mCit and 5.9 kb w/Gp91$^{phox}$. |
| Extra (E2 core and 4L core) Core | 7.4 kb w/mCit and 8.4kb w/Gp91$^{phox}$ |
| Extra (E2 core and 4L core) Ultra-core | 5.7 kb w/mCit and 6.7kb w/Gp91$^{phox}$ |

Additionally, in certain embodiments "extra" fragment are included. Thus for example we hypothesized that the RELA TF binding site may increase B-cell expression. RELA plays role in many cellular processes including inflammation and immunity. Moreover, there is a B-cell lineage specific DNAseI hypersensitivity at the RELA binding size. Accordingly, in certain embodiments, the TF binding footprint can be included in the element 2 component (see, e.g., Table 1, SEQ ID NO:7).

Additionally, in certain embodiments 4L "core" variant or a 4L "ultra core" variant can be included with the 4R component. Sizes of these "extra" fragment constructs are also shown in Table 2.

The constructs shown in Table 3 were tested:

TABLE 3

Lentiviral constructs tested.

Figure 12:
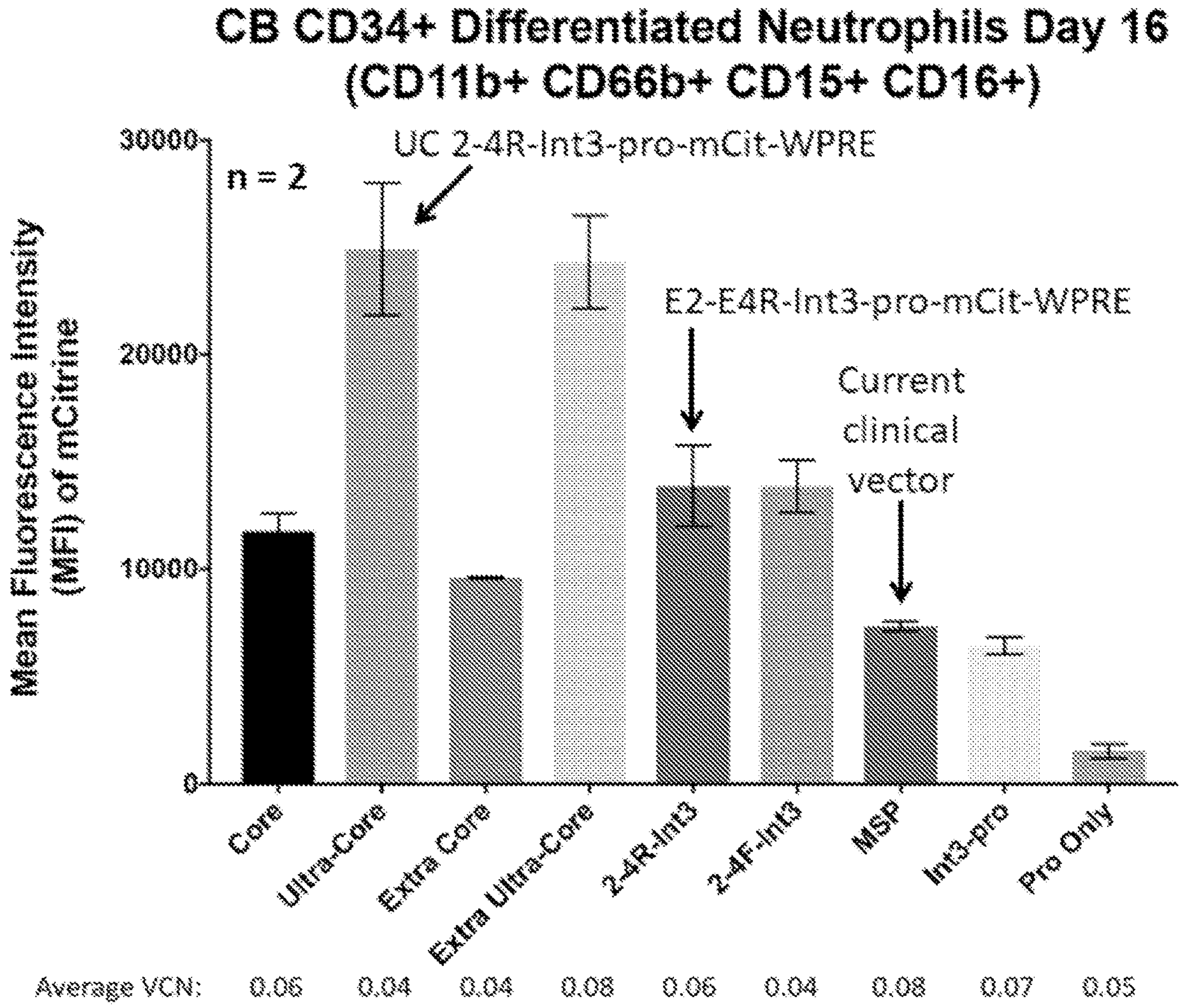
FIG. 12 shows expression of the reduced size vectors in CB CD34+ Differentiated Neutrophils Day 16. (CD11b+ CD66b+ CD15+ CD16+)

| Construct | Description |
|---|---|
| 1 Core | Core consists of: the 892 bp core fragment of element 2 (b-cell enhancer), the 500 bp fragment of 4R (myeloid enhancer), a 1536 bp core fragment of intron 3 consisting of a left, middle and right core fragments and a 267 bp core fragment of the endogenous CYBB promoter. In the context of FIG. 12, the opening reading frame was mCitrine. There is also presence of the WPRE element in the 3' UTR. |
| 2 Ultra core | Ultra-core consists of: 347 bp ultra-core element 2, a 254 bp ultra-core fragment of element 4R, a 720 bp ultra-core fragment of intron 3 consisting of the ultra-core middle and right fragments, and a 170 bp ultra-core fragment of the endogenous CYBB promoter. In the context of FIG. 12, the opening reading frame was mCitrine. There is also presence of the WPRE element in the 3' UTR. |
| 3 Extra core | Same as "CORE" but has the addition of a 556 bp extra element 2 fragment containing the RELA binding site, and the addition of 208 bp extra 4 L core fragment. |
| 4 Extra ultra core | Same as "Ultra core" but has the addition of a 556 bp extra element 2 fragment containing the RELA binding site, and the addition of 208 bp extra 4 L core fragment |
| 5 E2-E4R-Int3-pro-mCit-WPRE | The vector consist of the full sized 1092 bp element 2, the full sized 995 bp element 4R, the full sized 1778 bp intron 3 enhancer and the full sized 507 bp CYBB endogenous promoter. In the context of FIG. 12, the opening reading frame was mCitrine. There is also presence of the WPRE element in the 3' UTR. |
| 6 MSP | The current lentiviral vector undergoing clinical trials. The MSP is made from a fusion of the cathepsin G and c-fes promoter elements. See, e.g,. Santilli et al.(2011) *Mol. Therapy.*, 19(1): 122-122. |
| 7 Int3-pro | This vector consists of the full sized 1778 bp intron 3 enhancer and the full sized 507 bp CYBB endogenous promoter. In the context of FIG. 12, the opening reading frame was mCitrine. There is also presence of the WPRE element in the 3' UTR. |
| 8 Pro only | This vector contains just the full sized 507 bp CYBB endogenous promoter. In the context of FIG. 12, the opening reading frame was mCitrine. There is also presence of the WPRE element in the 3' UTR. |

Figure 13:
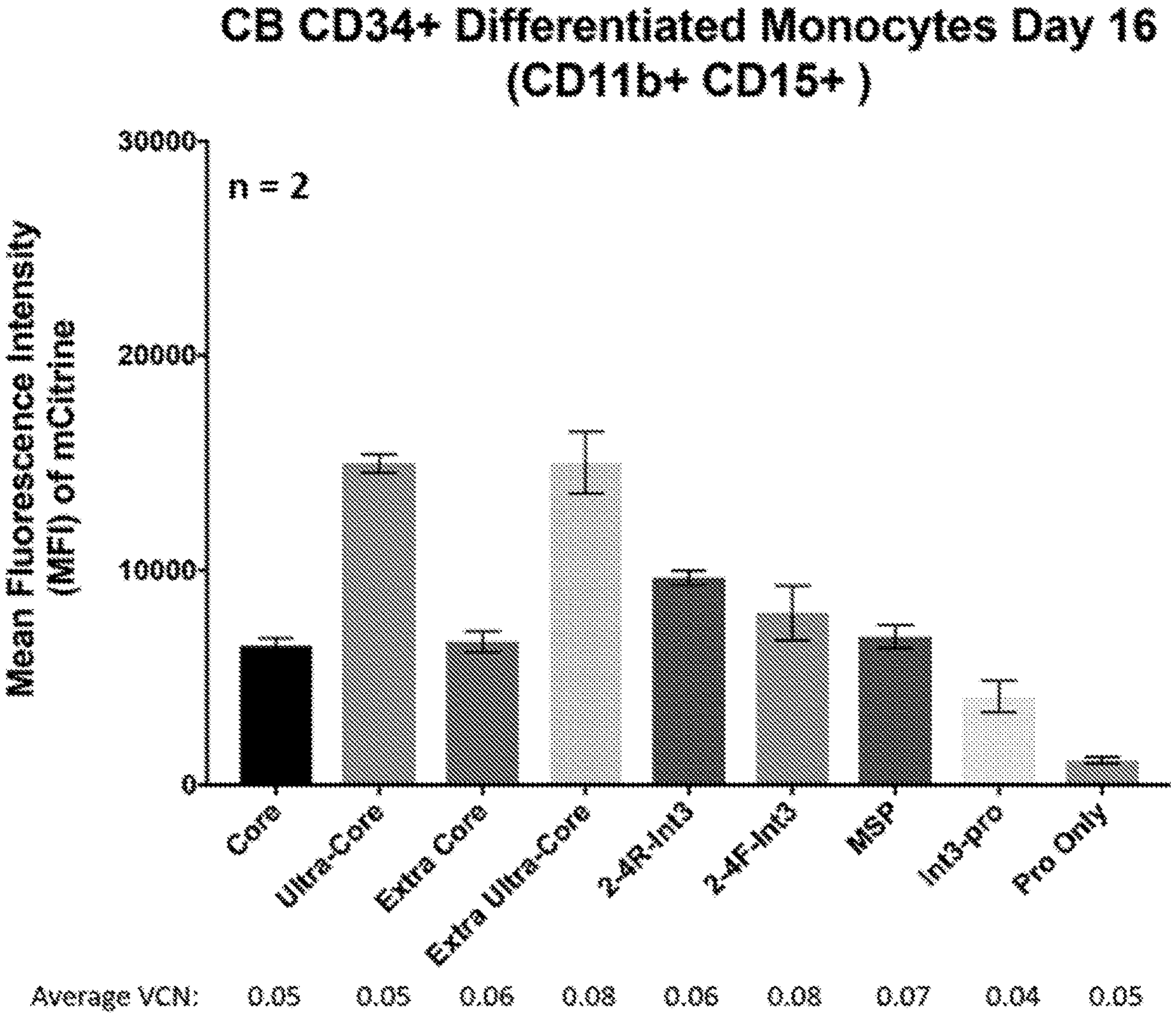
FIG. 13 shows expression of the reduced size vectors in CB CD34+ Differentiated Monocytes Day 16 (CD11b+ CD15+)

The ultra-core and extra ultracore variant vectors shows significantly higher expression in CB CD34+ differentiated neutrophils (CD11b+ CD66b+ CD15+ CD16+) (FIG. 12) and in CB CD34+ differentiated monocytes (CD11b+ CD15+) (FIG. 13) than the E2-E4R-Int3-pro-mCit-WPRE construct or the current clinical vector (MSP-Gp91$^{phox}$-WPRE).

Figure 14:
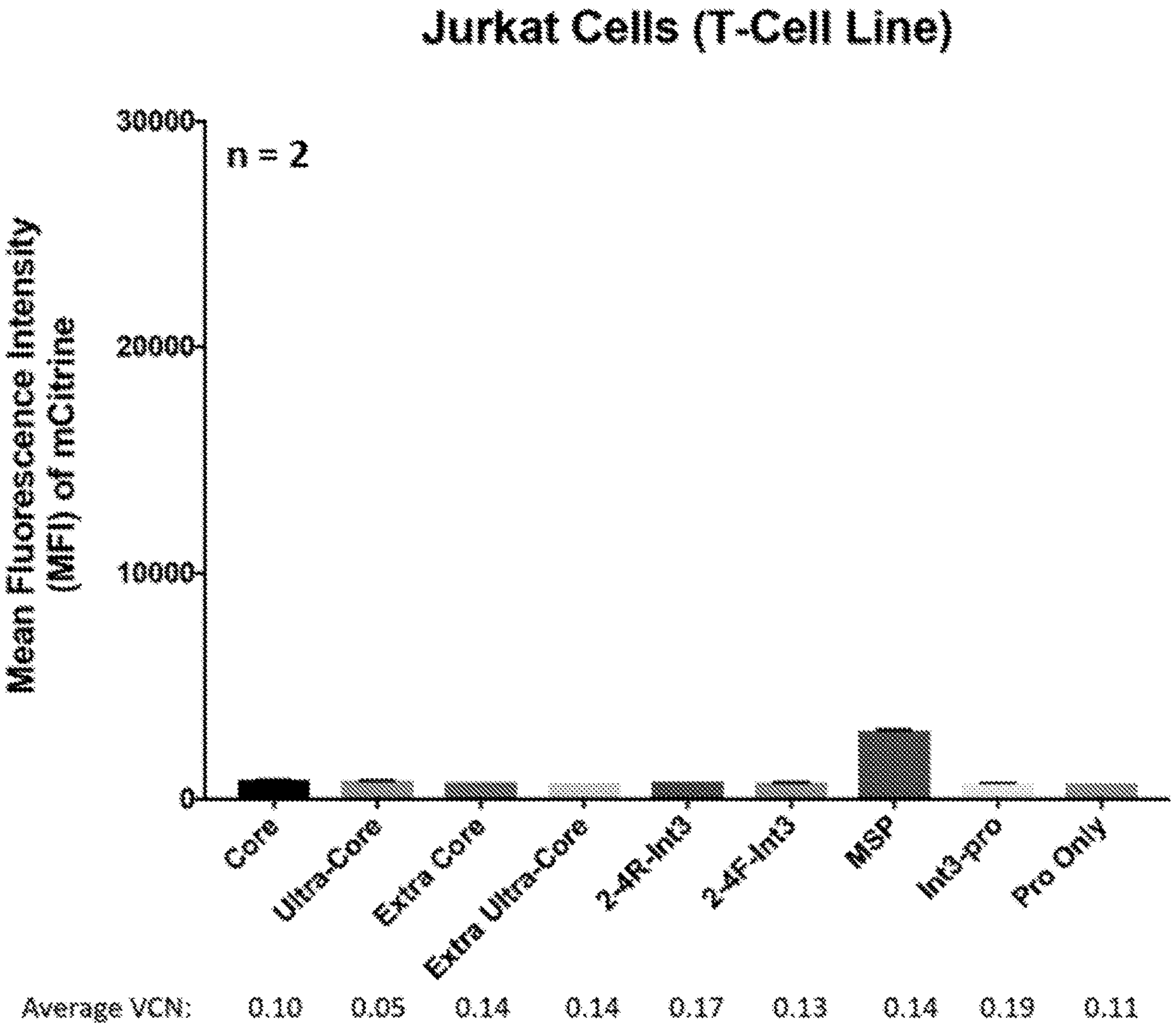
FIG. 14 shows expression of the reduced size vectors in Jurkat Cells (T-Cell Line).
Figure 15:
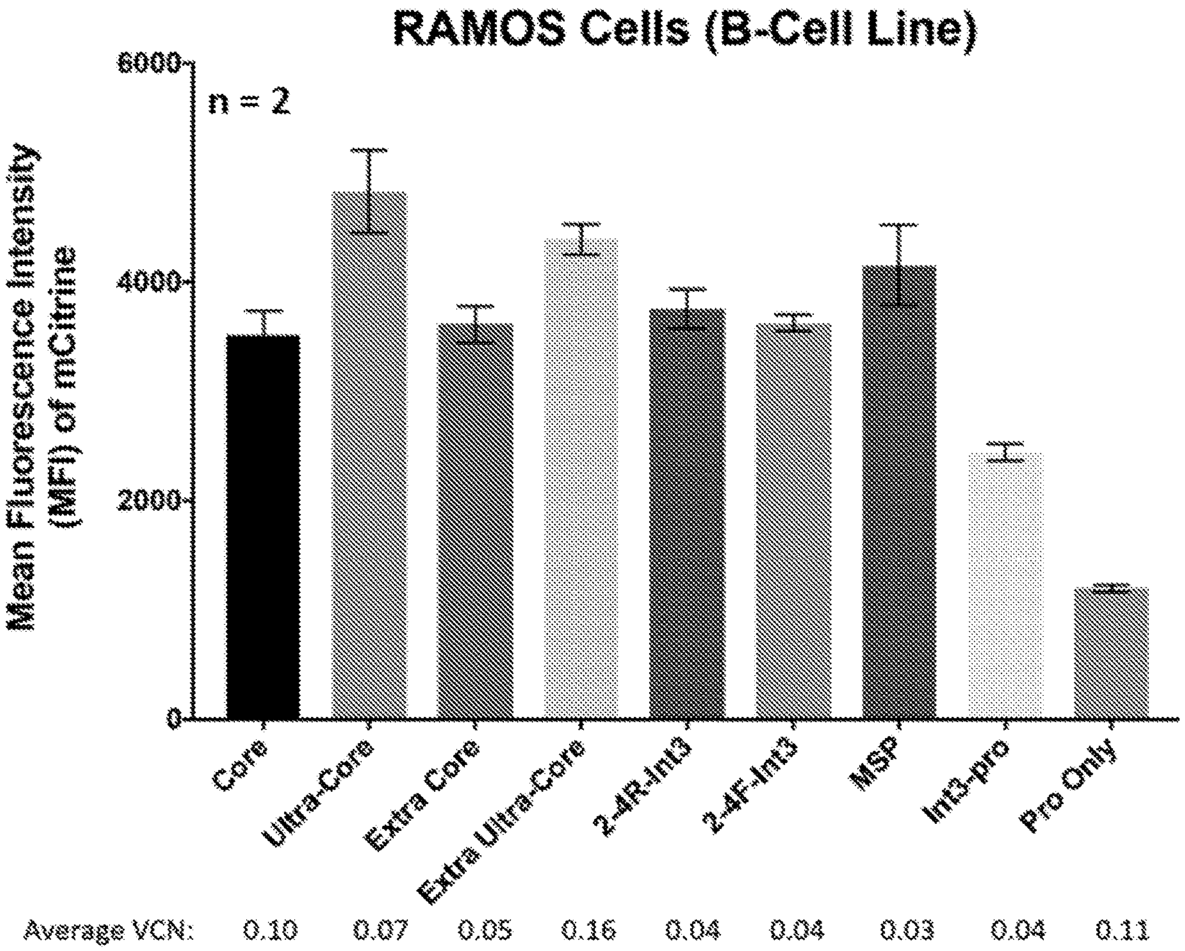
FIG. 15 shows expression of the reduced size vectors in RAMOS Cells (B-Cell Line).

All of the ultra-core and extra ultra core variant vectors showed low expression (lower than the current clinical vector) in Jurkat Cells (FIG. 14).

Figure 16:
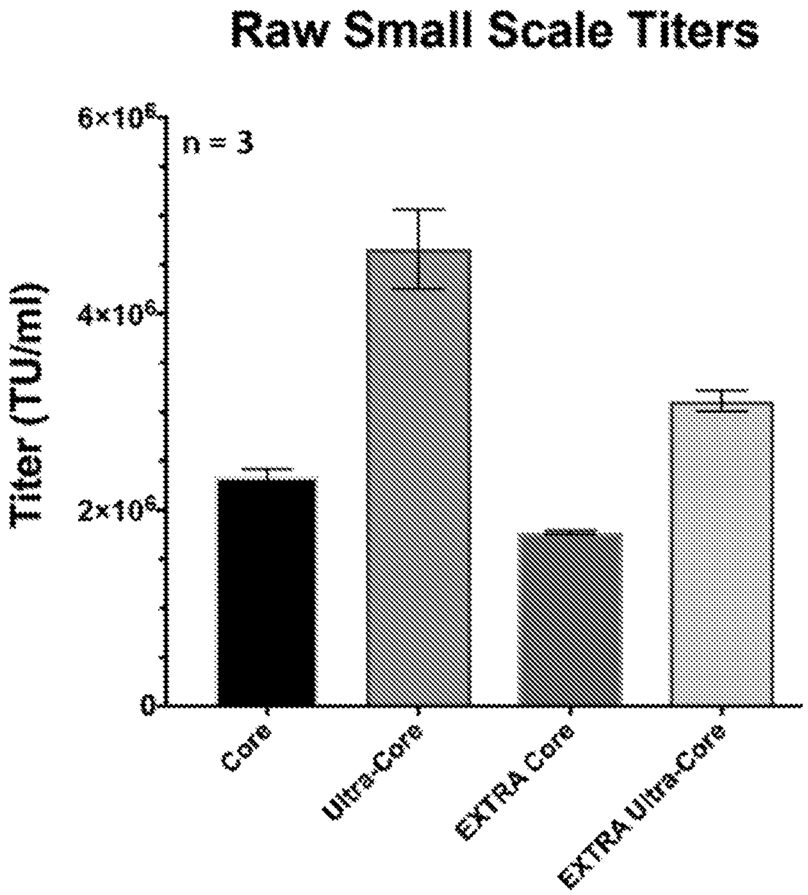
FIG. 16 shows raw small scale titers of the "core", the "ultra core", the "extra core" and the "extra ultra core" constructs.

As show in FIG. 16 ultra core vector and extra ultra core vectors showed higher titers than the core and extra core variants.

In view of this we conclude that by making 2.9 kb of deletions to our lead vector, we have increased expression as follows:

180% increase in neutrophils (3.4× higher than MSP)

150% increase in monocytes (2.2× higher than MSP)

129% increase in RAMOs (B-cell line) (1.16× higher than MSP)

The vector also retains specificity with no T-cell expression (no change). Additionally, by making 1.2 kb of deletions, we have decreased expression as follows:

15% reduction in neutrophils

33% reduction in monocytes

6% reduction in RAMOS (B-cell line)

In certain embodiments one particularly suitable vector is the ultra-core variant of 2-4R-Int3-pro-mCit-WPRE (UC 2-4R-Int3-pro-mCit-WPRE). The ORF of mCitrine can be replaced with the therapeutic transgene (a nucleic acid encoding Gp91$^{phox}$) to provide a clinically relevant vector.

Moreover, to maximize expression and titer a number of different codon optimizations were evaluated. These include jCAT, GeneArt, IDT, the codon optimized sequence in the current clinical vector (MSP-Gp91$^{phox}$-WPRE) and a Gp91$^{phox}$ cDNA.

We originally screened the different codon optimization in the Int3-pro-Gp91$^{phox}$-WPRE vector backbone. However, the Int3-pro vector has high lineage specific expression and only expresses in mature neutrophils and did not express well in the PLB-985 CYBB$^{-/-}$ cell line (human promyeloblasts cell line). In order to use the PLB-985 X-CGD cell line, we decided to screen the different codon optimizations of Gp91$^{phox}$ with the MSP-Gp91$^{phox}$-WPRE vector backbone.

The lead codon optimized sequence can be transferred to the various X-CGD vectors described herein. We note that codon optimization is for optimization of expression within a specific species (possibly even cell type), however the ideal codon optimization should be independent of which promoter/vector it is expressed from.

Figure 17:
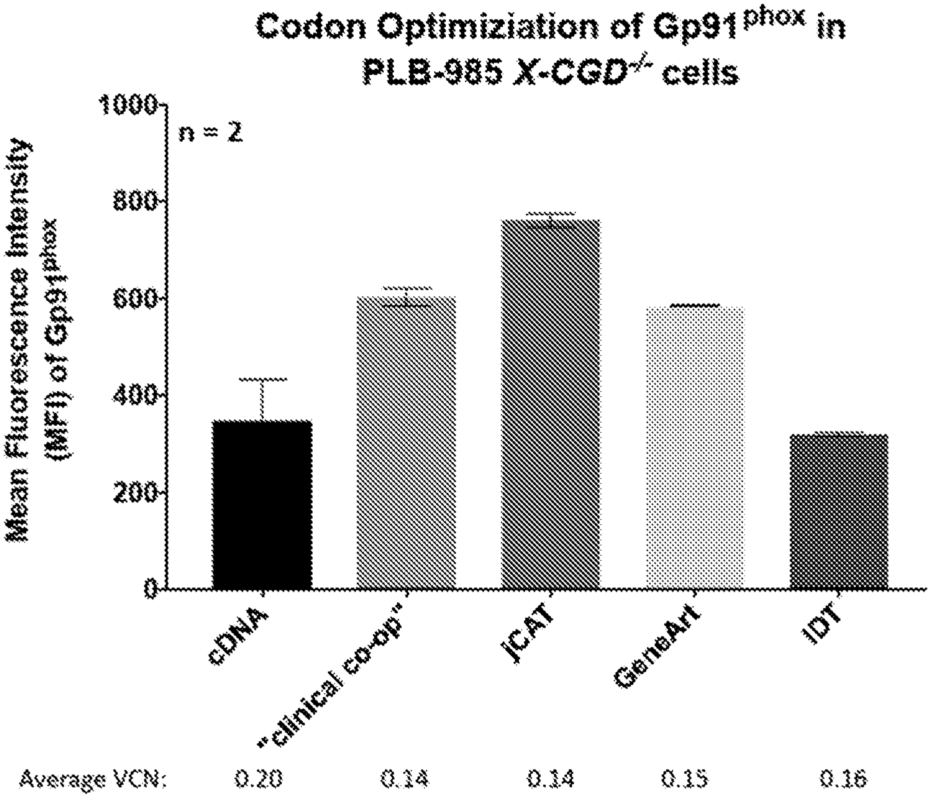
FIG. 17 shows the expression levels produced by various codon optimizations of Gp91$^{phox}$ in PLB-985 X-CGD$^{-/-}$ cells.
Figure 18:
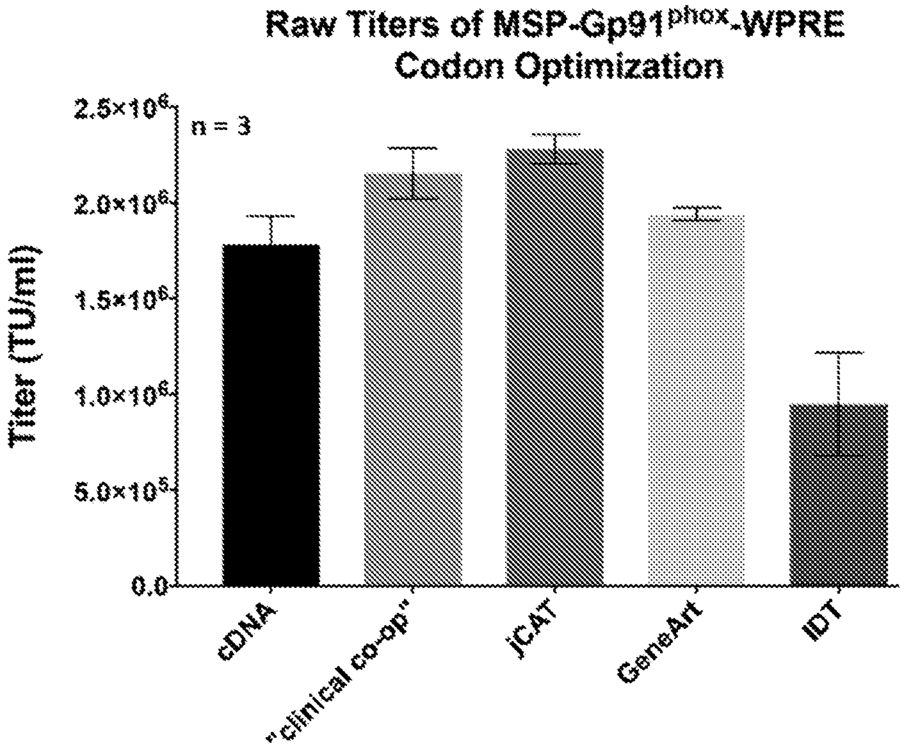
FIG. 18 shows the raw titers of various codon optimizations of MSP-Gp91$^{phox}$-WPRE.

As shown in FIG. 17, the jCAT optimization of gp91$^{phox}$ produced the highest expression level of the optimizations tested. The raw titers of the various optimizations are shown in (MSP-Gp91$^{phox}$-WPRE) optimization and the jCAT optimization did not significantly differ (FIG. 18).

In view of the foregoing, we conclude that jCAT is the optimal codon optimization of Gp91$^{phox}$. This codon optimization increases expression over 2-fold higher than the native cDNA sequence and 1.2 fold higher than the current codon optimized sequence in the clinical MSP-Gp91$^{phox}$-WPRE vector. This optimization also increases titer 1.2× higher than the native cDNA sequence (MSP-Gp91$^{phox}$-WPRE).

By implementing a bioinformatics guided approach, we have rationally designed a novel X-CGD lentiviral vector possessing strict lineage and stage specific expression which mimics the expression pattern of the native CYBB gene. One lead candidate vector is the ultra core: UC 2-4R-Int3-pro-Gp91$^{phox}$(jCAT)-WPRE vector, e.g., as illustrated in FIG. 20, panel A. A map of this vector is shown in FIG. 20, panel B, and the sequence is shown in Table 1, (SEQ ID NO:22).

Example 2

Lineage-Specific Expression of MeloVec

Example 1, above describes the generation of an optimized lead candidate vector: UC 2-4R-Int3-pro-mCit-WPRE (aka MyeloVec). This vector showed improved titer, improved infectivity, and improved expression.

A number of different codon optimizations were screened and it was decided to replace the open reading frame of mCtrine with a jCAT codon optimization Gp91$^{phox}$ to express the actual therapeutic transgene.

As described herein in-vitro lineage specific expression of MyeloVec (expressing mCitrine) was demonstrated by transplanting transduced human healthy donor (HD) cord blood (CB) CD34+ cells into NOD.Cg-Prkdcscid Il2rgtm1Wjl/SzJ (NSG) mice. Additionallyh the ability of MyeloVec (expressing codon optimized Gp91$^{phox}$) to functionally correct for the X-CGD phenotype was demonstrated by:

1) Transducing murine X-CGD lineage negative (Lin−) hematopoietic stem and progenitor cells (HSPCs) and in-vitro differentiating to neutrophils to evaluate restoration of Gp91$^{phox}$ expression and restoration of functional oxidase activity;

2) Transducing murine X-CGD Lin-HSPCs and transplanting cells into congenic B6.SJL-Ptprca Pepcb/BoyJ (Pepboy) mice to demonstrate in-vivo functional correct of the disease; and 3) Transducing human X-CGD patient cells and in-vitro differentiating to neutrophils to demonstrate restoration of Gp91$^{phox}$ expression and functional oxidase activity.

Figure 21:
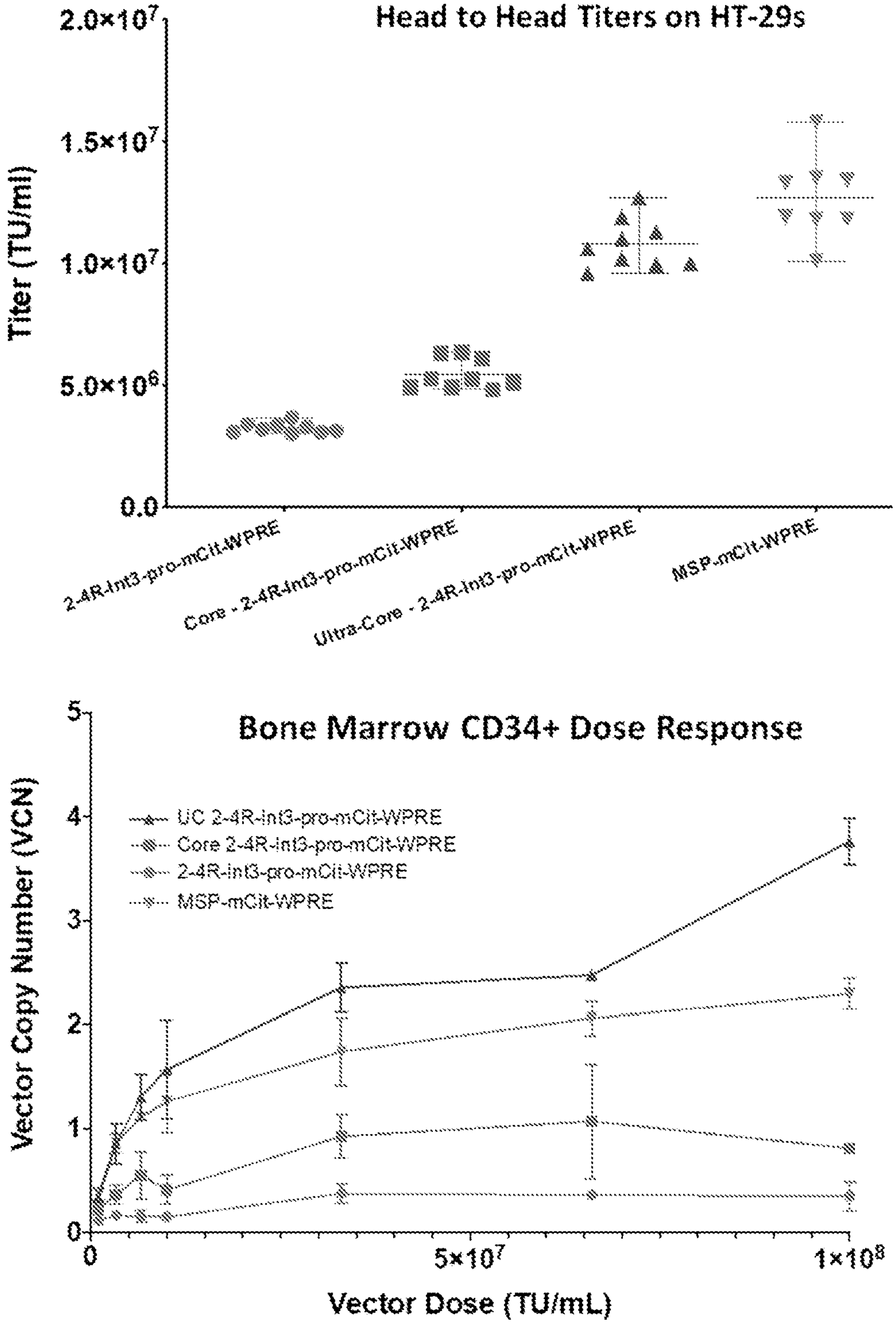
FIG. 21 illustrates improvement in titer (top panel) and infectivity (bottom panel) as the vector was optimized from the original 2-4R-Int3-pro-mCit-WPRE to the CORE variant and to the ULTRA CORE (UC) variant. The UC variant (MyeloVec is a lead candidate vector).

FIG. 21 demonstrates the improvement in titer (top panel) and infectivity (bottom panel) as we optimized our vector from the original 2-4R-Int3-pro-mCit-WPRE to the CORE variant and to the ULTRA CORE (UC) variant. We improved titer and infectivity of as we decreased size of our vector from the original 2-4R-Int3-pro-mCit-WPRE to the CORE variant and to the Ultra Core (UC) variant.

Figure 22:
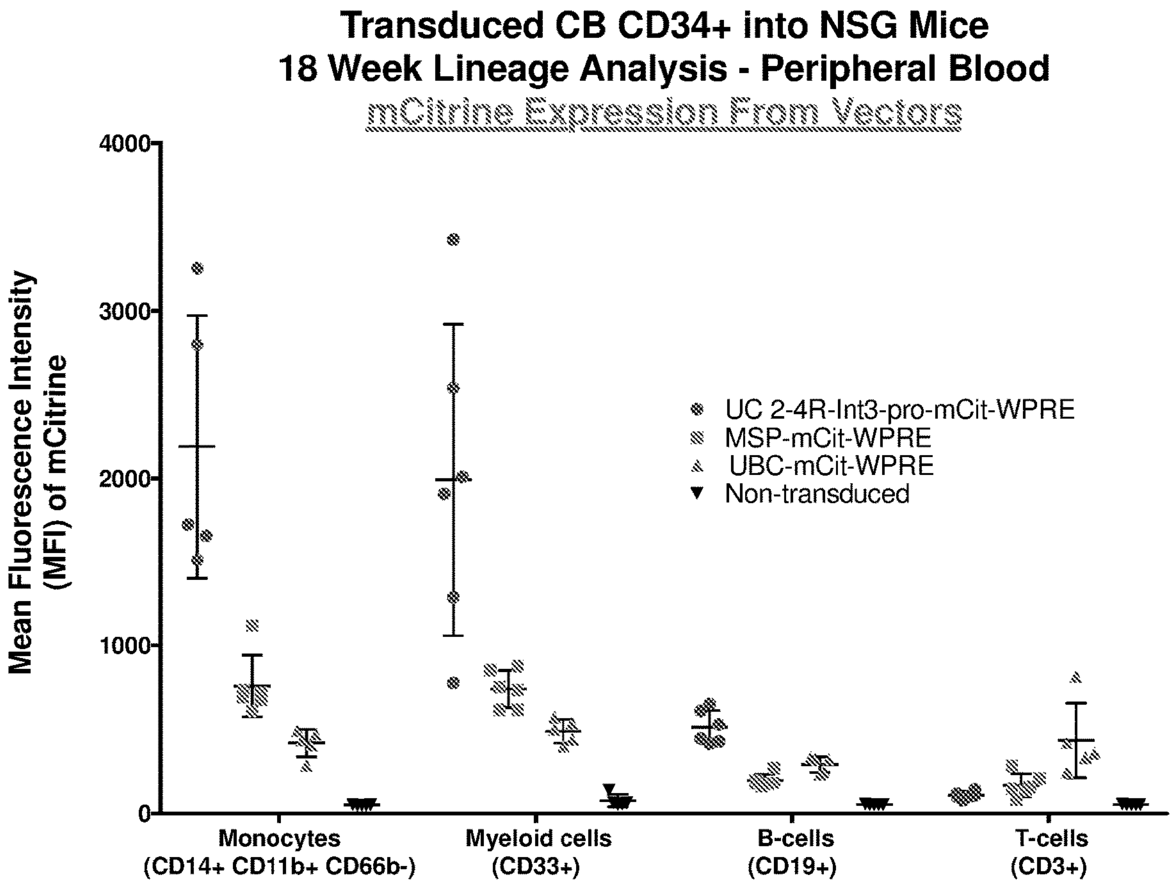
FIG. 22, panels A-B, shows that MyeloVec is able to recapitulate the endogenous expression pattern of the native CYBB gene in blood cells (panel A) and bone marrow cells (panel B) respectively.

As shown in FIG. 22 MyeloVec (expressing mCitrine) is able to recapitulate the endogenous expression pattern of the native CYBB gene. In this experiment, we transduced healthy donor (HD) cord blood (CB) CD34+ hematopoietic stem and progenitor cells (HSPCs) and transplanted the cells into NOD.Cg-Prkdcscid Il2rgtm1Wjl/SzJ (NSG) mice. The gene modified cells will give rise to all the different lineages of the hematopoietic system. By evaluating which lineages are expressing mCitrine and to what degree, we can determine the lineage specific expression pattern of our vector and see if it mimics the endogenous expression pattern of the native CYBB gene.

MyeloVec is able to recapitulate the endogenous expression pattern of the native CYBB gene—very high expression in neutrophils, high bulk myeloid expression, medium levels of B-cell expression and minimal expression in T-cells and HSPCs. This is shown in blood FIG. 22, panel A, and bone marrow (FIG. 22, panel B).

Figure 23:
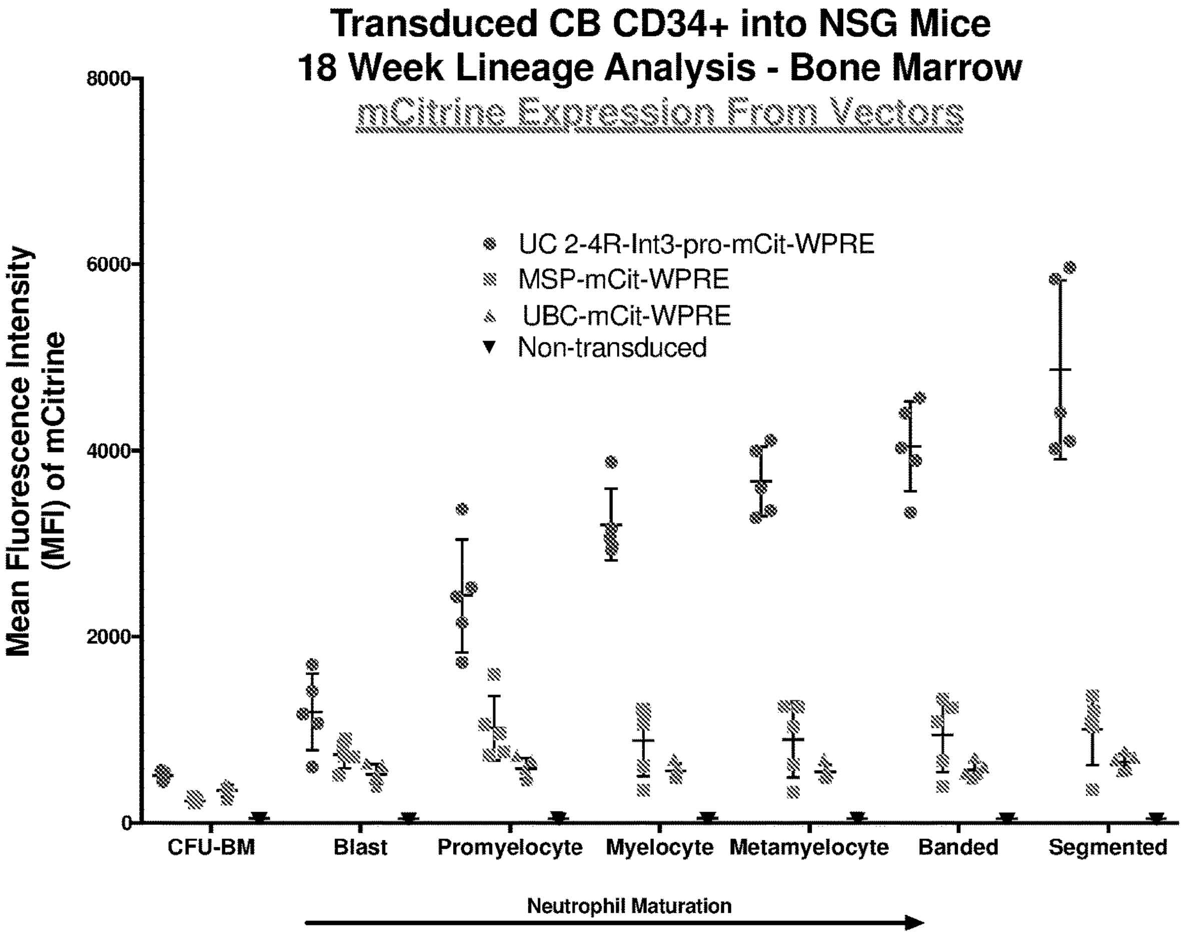
FIG. 23 shows that MyeloVec is able to recapitulate the temporal expression pattern of the native CYBB gene throughout neutrophil development. The expression gets higher as the neutrophils mature, mimicking the pattern of the native CYBB gene.

MyeloVec is also able to recapitulate the temporal expression pattern of the native CYBB gene throughout neutrophil development. The expression gets higher as the neutrophils mature, mimicking the pattern of the native CYBB gene (see, e.g., FIG. 23).

Thus, in transduced human cord blood CD34+ cells transplanted into NSG mice, the pattern of mCitrine expression from MyeloVec recapitulated the endogenous expression pattern of Gp91$^{phox}$ across multiple lineages in the blood and bone marrow cells (see, e.g., Table 4).

TABLE 4

Expression pattern of MyeloVec.

| Bone Marrow | Blood |
|---|---|
| Extremely high expression in neutrophils-4.8× MSP | Very high expression in monocytes-2.9× MSP |
| Very high expression in monocytes-2.6× MSP | Very high expression in bulk myeloid cells-2.7× MSP |
| Very high expression in bulk myeloid cells-2.9× MSP | High expression in B-cells-2.6× MSP |
| High expression in B-cells-3.2× MSP | No expression in T-cells-62% of MSP |
| No expression in T-cells-73% of MSP | |
| Low expression in HSCs-65% of MSP | |

We then replaced the open reading frame containing the mCitrine reporter gene with a jCAT codon optimized version of Gp91$^{phox}$ to express the therapeutic transgene for our functional studies.

Figure 24:
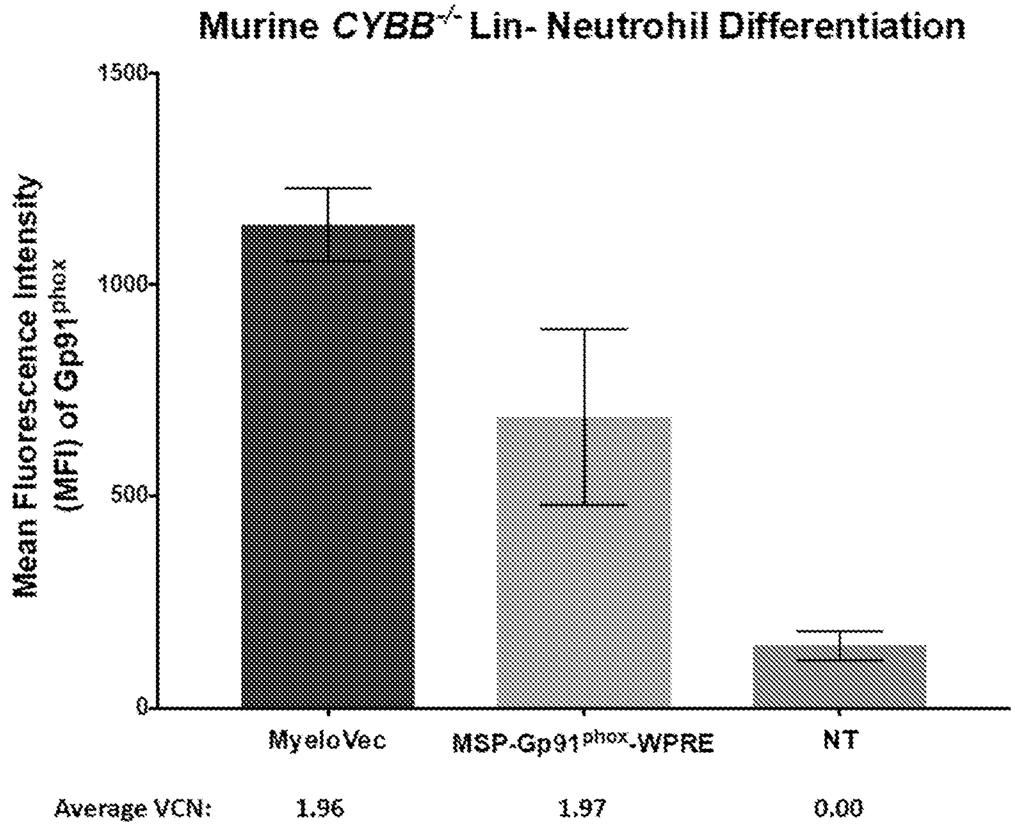
FIG. 24 shows the restoration of Gp91$^{phox}$ expression.
Figure 25:
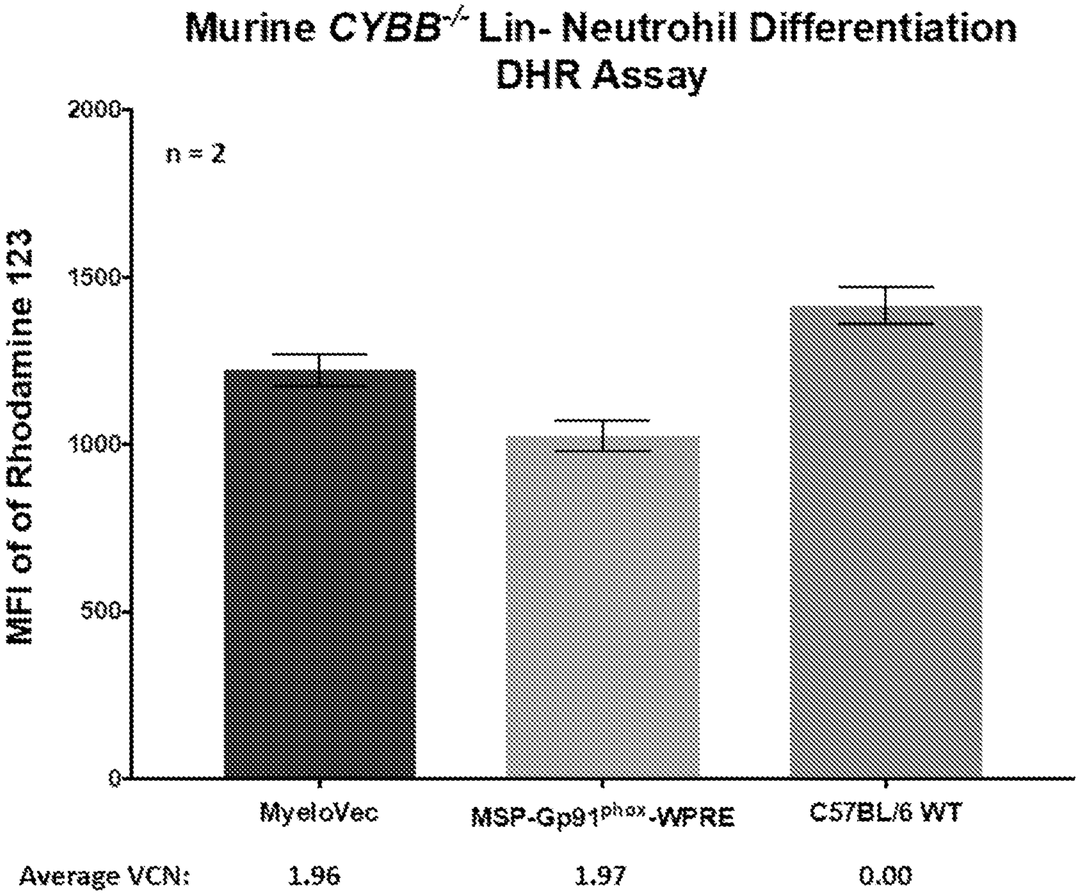
FIG. 25 shows show the restoration of oxidase activity to wildtype levels.

FIGS. 24 and 25 demonstrate the ability of MyeloVec to functionally correct for the X-CGD phenotype in-vitro in mouse X-CGD HSPCs. For this experiment, we transduced murine X-CGD lineage negative (Lin−) Hematopoietic Stem and Progenitor Cells (HSPCs) and differentiate the cells to mature neutrophils to demonstrate the ability of our lead candidate vector (UC-2-4R-Int3-pro-Gp91$^{phox}$(jCAT)-WPRE) to restore expression of Gp91$^{phox}$ (FIG. 24) and oxidase activity FIG. 25. In these experiments, oxidase activity was assessed by the Dihydrorhodamine (DHR) assay.

As shown in FIG. 24, it is believed that MyeloVec can restore higher levels of Gp91$^{phox}$ than the current clinical vector (MSP) in neutrophils differentiated from X-CGD mouse HPSCs. Additionally, MyeloVec is able to restore oxidase activity to WT levels in transduced murine X-CGD cells differentiation into mature neutrophils (see, e.g., FIG.

25). Thus, it appears that MyeloVec expresses Gp91$^{phox}$ 1.6 fold higher than MSP (current clinical vector) in murine CYBB Lin-in-vitro differentiated neutrophils and MyeloVec is able to restore oxidase activity to WT levels in murine CYBB Lin-in-vitro differentiated neutrophils.

FIGS. 26-29 demonstrate the ability of MyeloVec to correct the X-CGD phenotype in-vivo in the X-CGD mouse model. Briefly, HPSCs were isolated from X-CGD mice and transduced with MyeloVec. The gene modified cells were then transplanted into congenic B6.SJL-Ptprca Pepcb/BoyJ (Pepboy) mice. Mice were harvested 16 weeks post-transplant for analysis of Gp91$^{phox}$ expression and restoration of oxidase activity across the different hematopoietic lineages.

Figure 26:
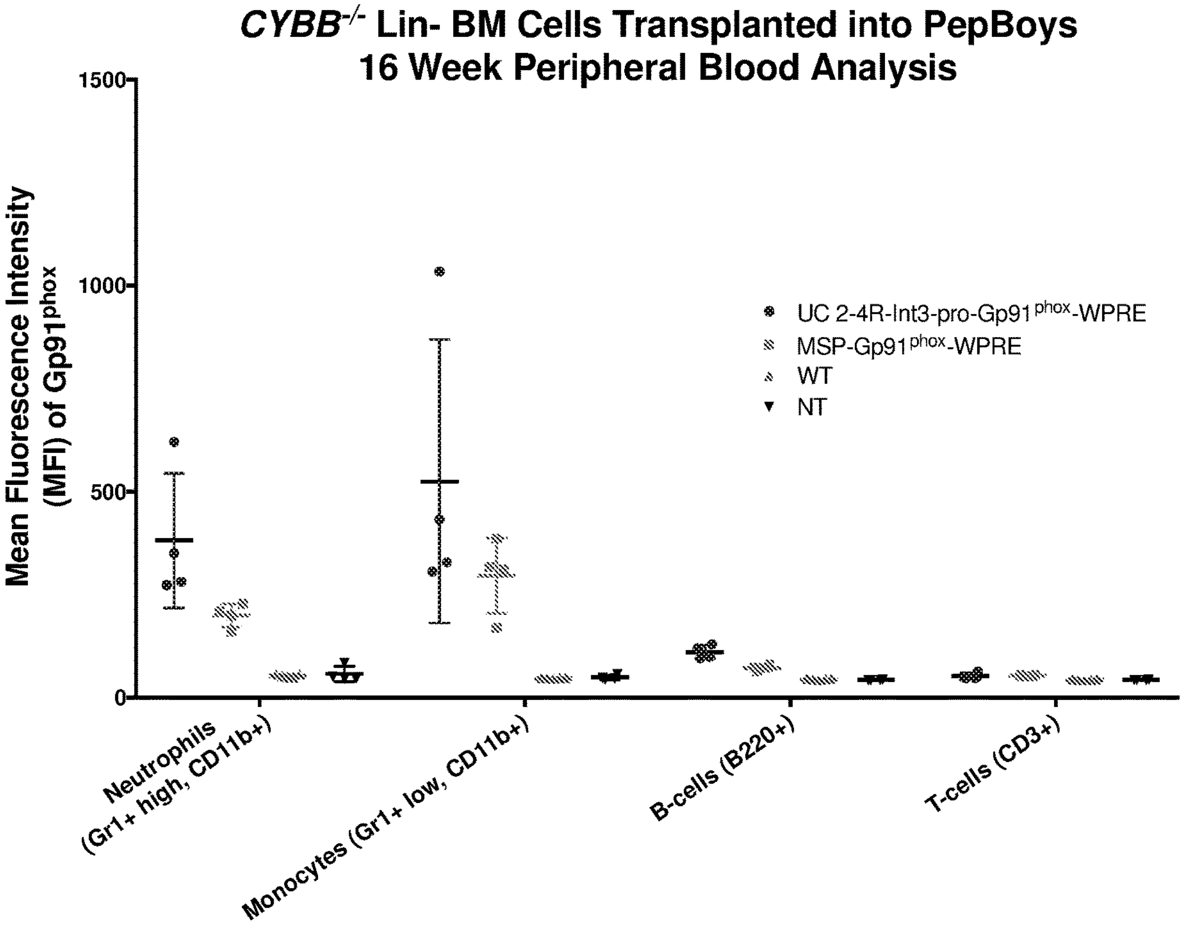
FIG. 26 shows restoration of Gp91$^{phox}$ expression in neutrophils and monocytes in the peripheral blood.
Figure 27:
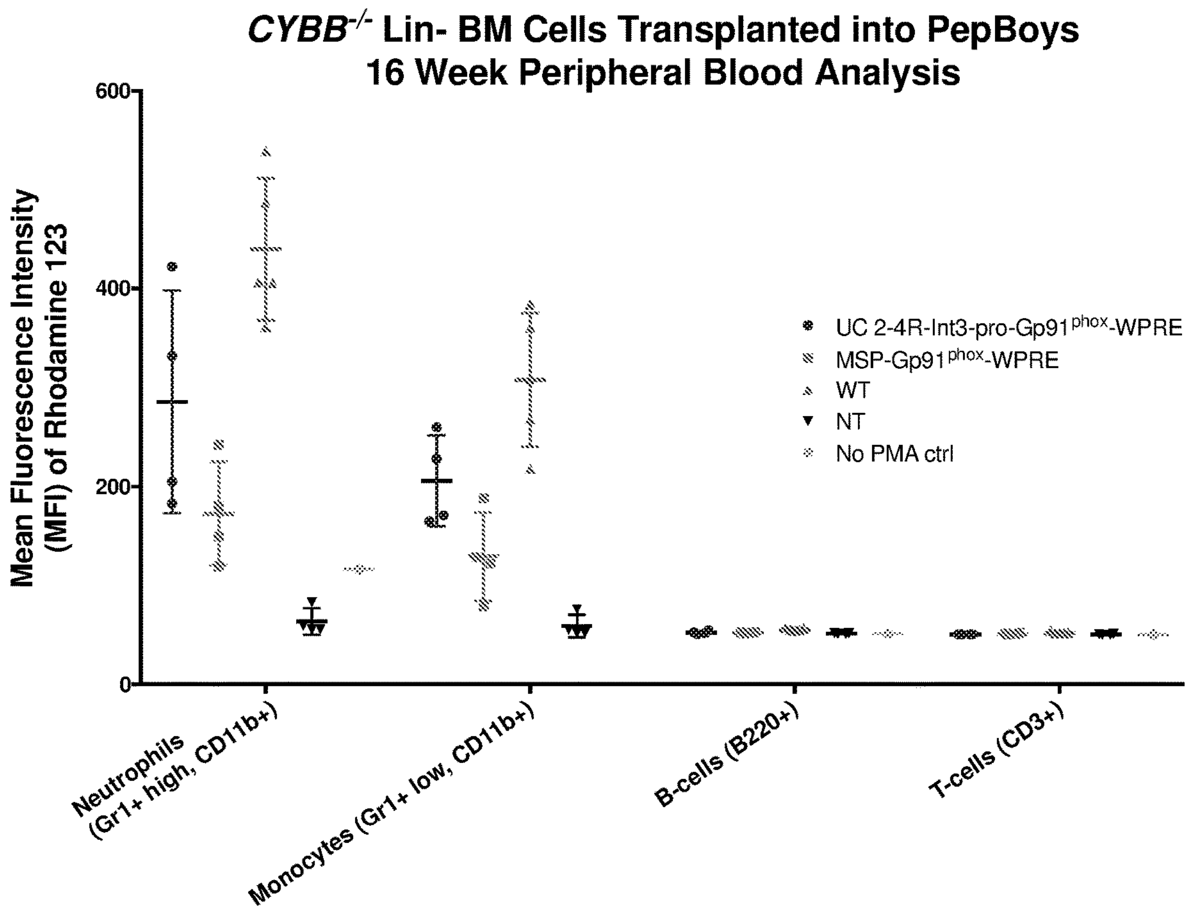
FIG. 27 shows restoration of oxidase activity near wild-type levels in the blood neutrophils and monocytes.
Figure 28:
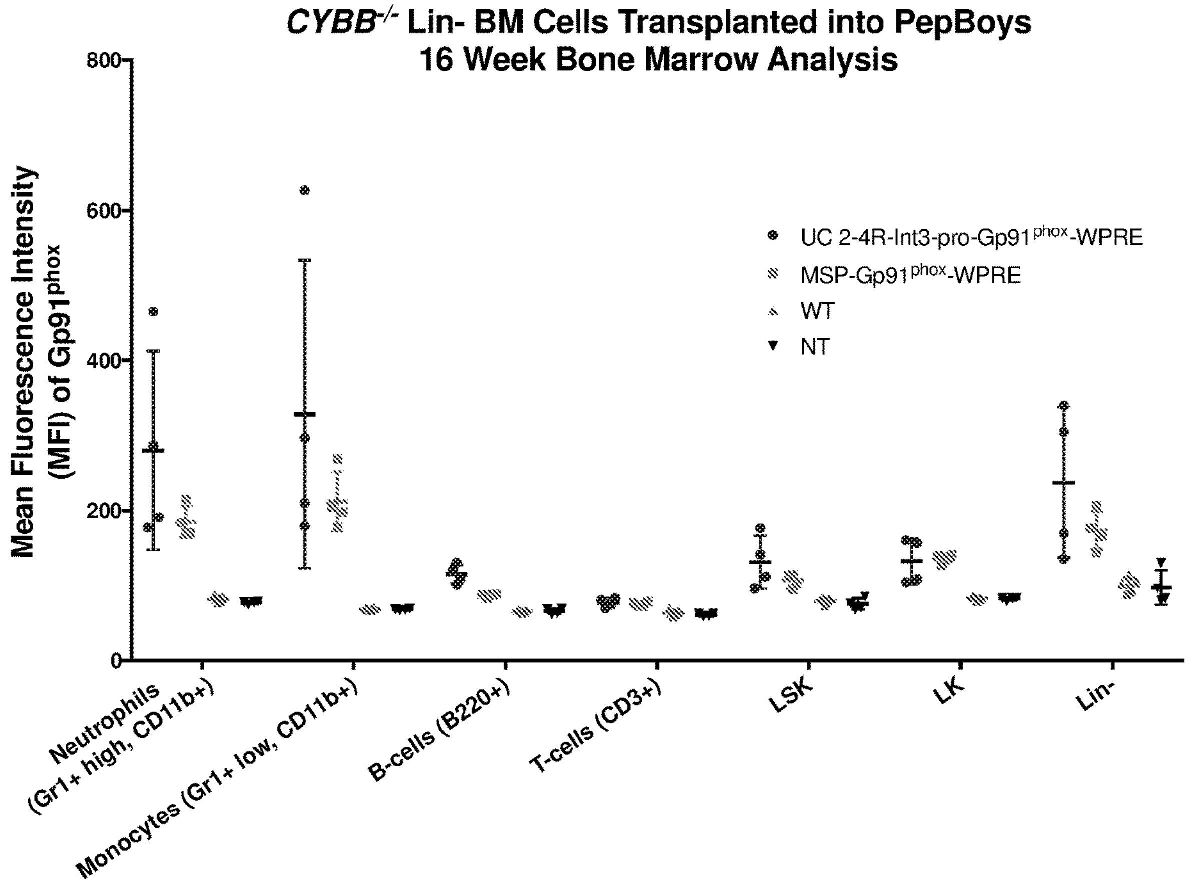
FIG. 28 shows restoration of high levels of Gp91$^{phox}$ expression in the bone marrow neutrophils and monocytes.
Figure 29:
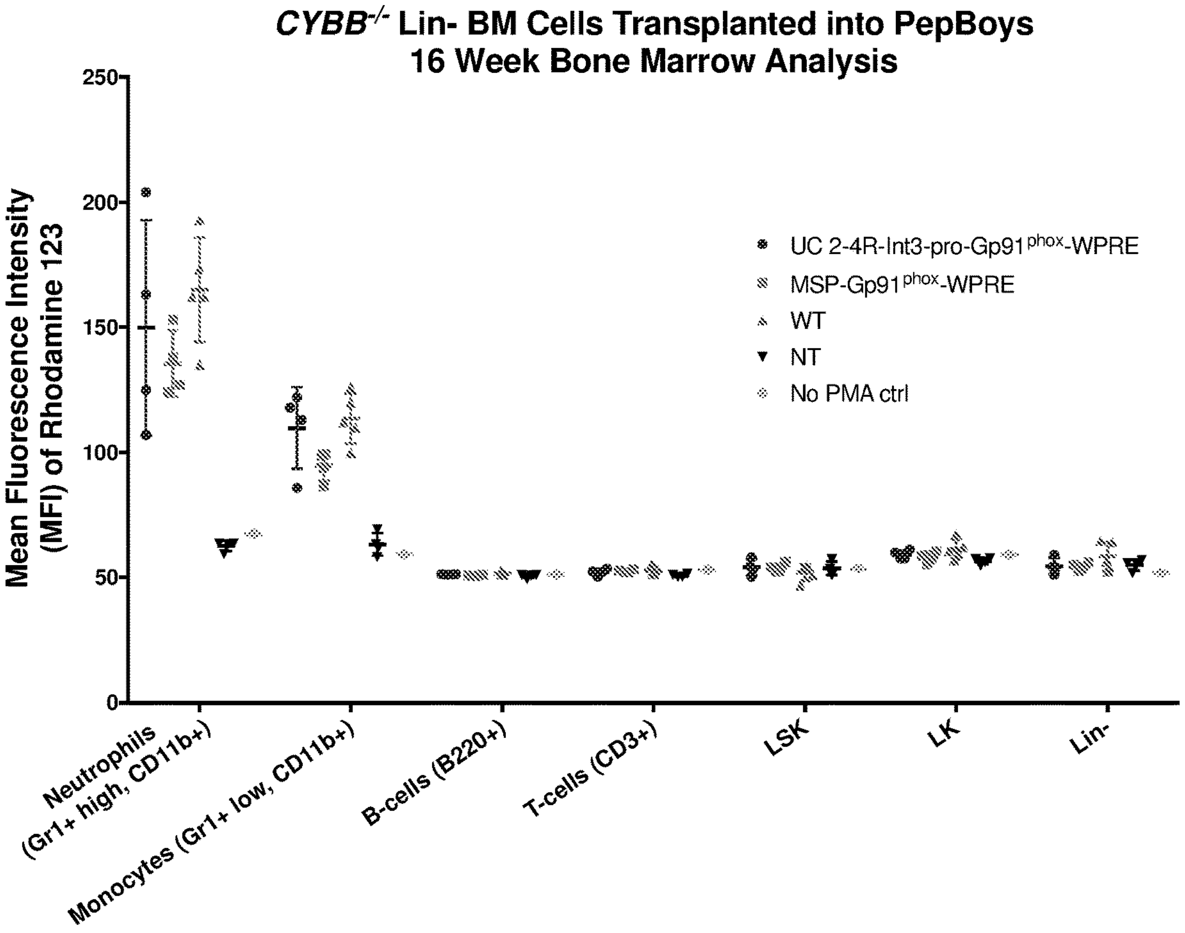
FIG. 29 shows restoration of wildtype levels of oxidase activity.

High levels of Gp91$^{phox}$ expression was restored in neutrophils and monocytes in the peripheral blood (see, e.g., FIG. 26). This led to a restoration of oxidase activity near wildtype levels in the blood neutrophils and monocytes (see, e.g., FIG. 27). High levels of Gp91$^{phox}$ expression was also restored in the bone marrow neutrophils and monocytes (see, e.g., FIG. 28) which led to restoration of wildtype levels of oxidase activity (see, e.g., FIG. 26). Thus, it appears that we have corrected the X-CGD mouse model in-vivo.

Figure 30:
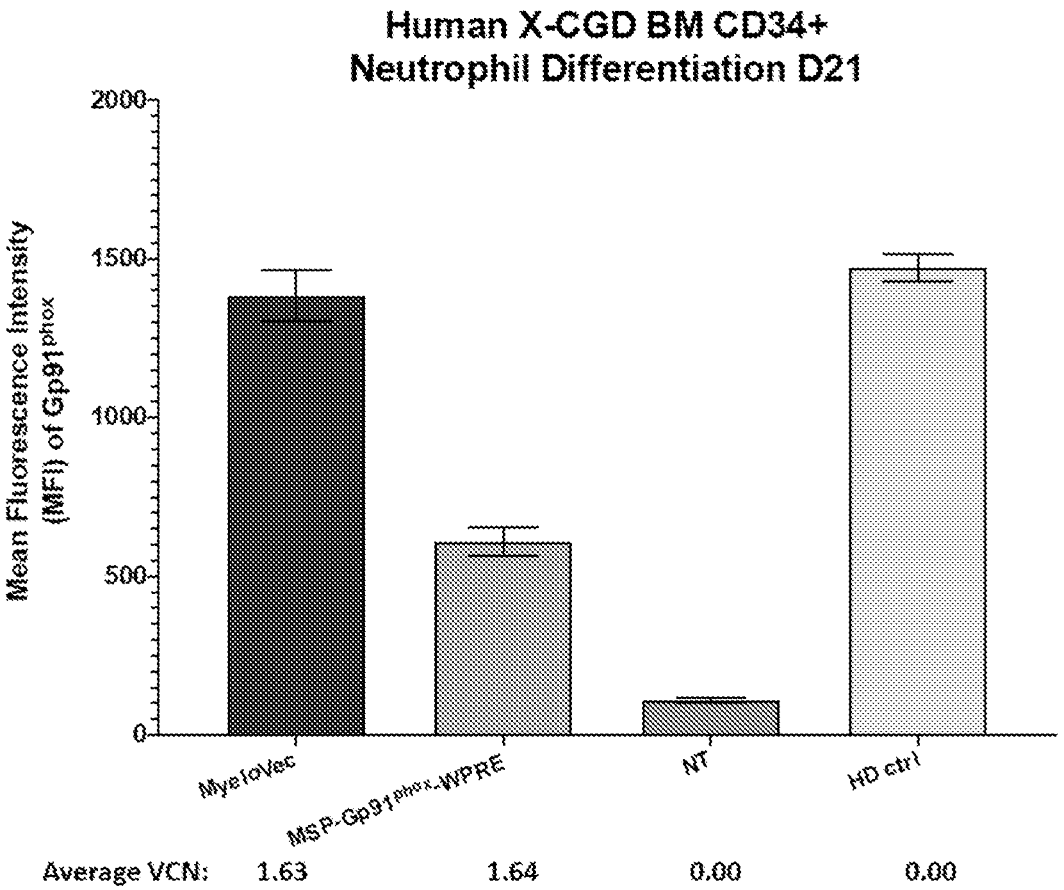
FIG. 30 shows the ability of MyeloVec to restore wildtype levels of Gp91$^{phox}$ expression in the human X-CGD neutrophils.
Figure 31:
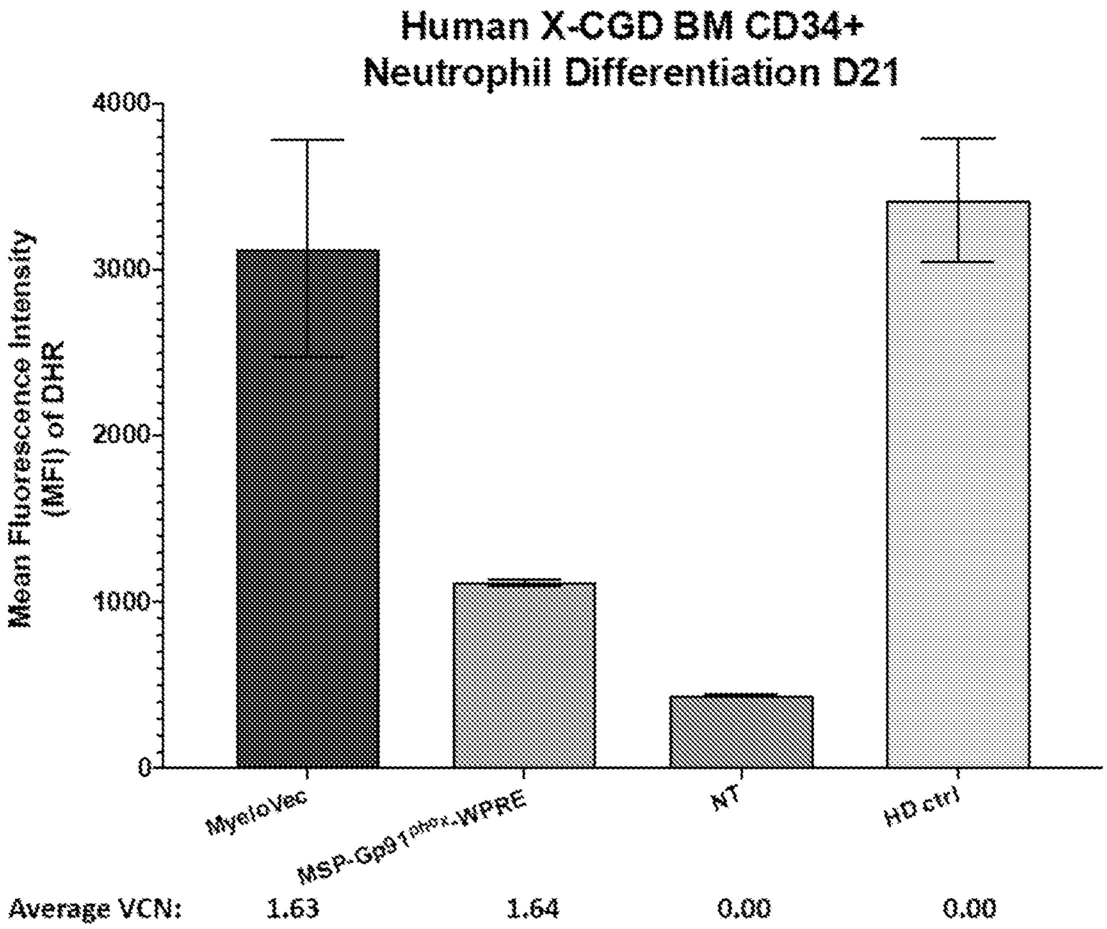
FIG. 31 shows the ability of MyeloVec to restore wildtype levels of cellular oxidase activity in the human X-CGD neutrophils (DHR assay).
Figure 32:
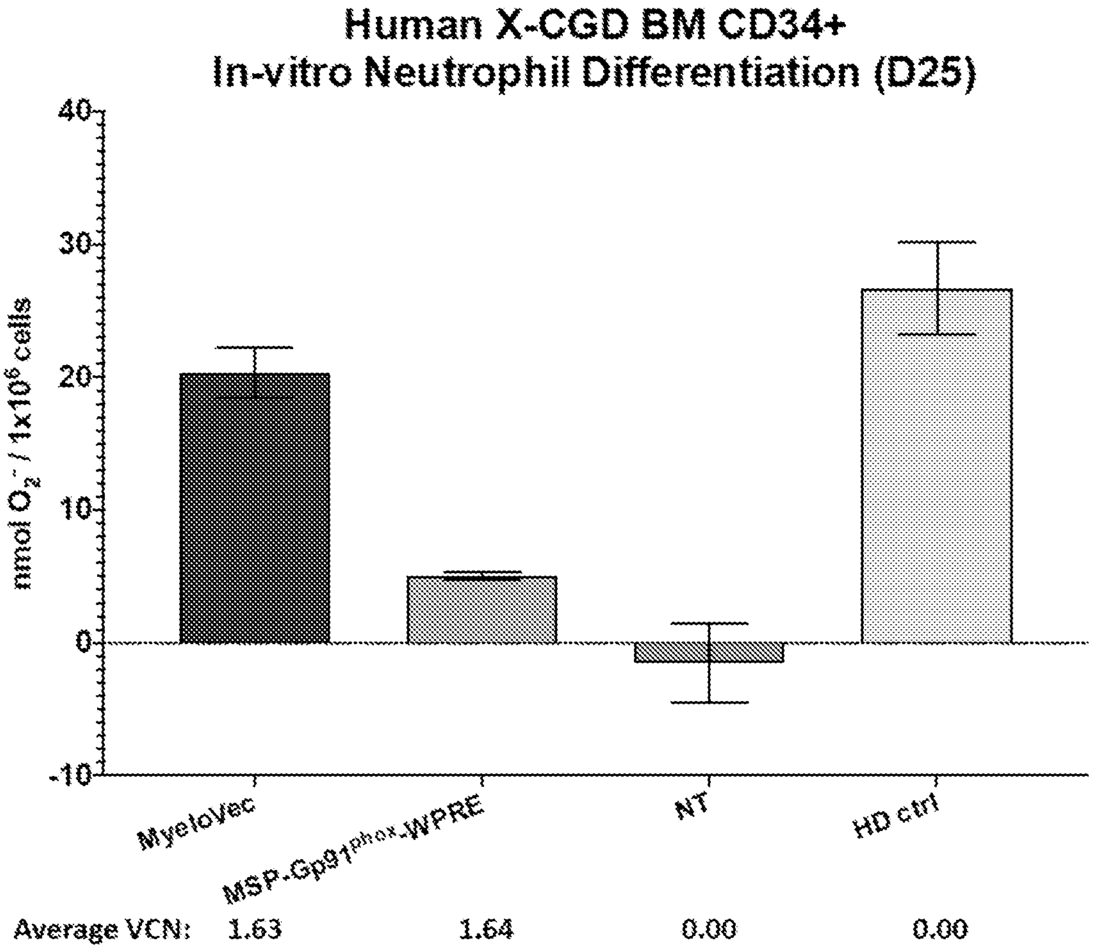
FIG. 32 shows the ability of MyeloVec to restore wildtype levels of bulk oxidase activity in human X-CGD neutrophils at an average VCN of 1.63 (cytochrome C assay).

To demonstrate the ability of MyeloVec to functionally correct human patient X-CGD cells in vitro, we transduced human X-CGD HSPCs with MyeloVec and differentiated the cells to mature neutrophils in-vitro. We then measured restoration of Gp91$^{phox}$ expression and restoration of oxidase activity by the DHR assay and the cytochrome C assay. FIG. 30 shows the ability of MyeloVec to restore wildtype levels of Gp91$^{phox}$ expression in the human X-CGD neutrophils. FIG. 31 shows the ability of MyeloVec to restore wildtype levels of cellular oxidase activity in the human X-CGD neutrophils (DHR assay). FIG. 32 shows the ability of MyeloVec to restore wildtype levels of bulk oxidase activity in human X-CGD neutrophils at an average VCN of 1.63 (cytochrome C assay).

Thus, by implementing a bioinformatic-based design approach we developed our lead candidate X-CGD vector UC-2-4R-Int3-pro-coGp91$^{phox}$-WPRE (MyeloVec) (see, e.g., FIG. 20, panels A and B, and SEQ ID NO: 22).

Conclusions

The experiments described above, demonstrate the ability to correct the X-CGD phenotype in-vivo in the murine X-CGD mouse model. In transduced murine X-CGD Lin-cells transplanted into lethally irradiated PepBoy mice:

MyeloVec was able to restore oxidase activity to WT levels in bone marrow neutrophils and monocytes;

MyeloVec achieved close to WT levels of oxidase activity in peripheral blood neutrophils and monocytes at a VCN of 1.74 and greater; and In-vitro differentiated neutrophils from human X-CGD patient CD34+ HSPCs transduced with MyeloVec restored Gp91$^{phox}$ expression and functional oxidase activity to healthy donor levels at an average VCN of 1.63.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

CYBB promoter

SEQ ID NO: 1

```
tagcacataaaattggcacatattaagcattttgtaaatatcaaccattacaattgttacta

cttttctcagcaaggctatgaatgctgttccagcctgtcaaaatcacacctgtttaatgtgt

tttacccagcacgaagtcatgtctagttgagtggcttaaaaattgtgatcaaatagctggtt

agttaaaaagttatttcactgtgtaaaatacatcccttaaaatgcactgttatttatctctt

agttgtagaaattggtttcattttccactatgtttaattgtgactggatcattatagaccct

ttttttgtagttgttgaggtttaaagatttaagtttgttatggatgcaagcttttcagttga

ccaatgattattagccaatttctgataaaagaaaaggaaaccgattgccccagggctgctgt

tttcatttcctcattggaagaagaagcatagtatagaagaaaggcaaacacaacacattcaa

cctctgccacc
```

Minimal CYBB promoter (core)

SEQ ID NO: 2

```
tatctcttagttgtagaaattggtttcattttccactatgtttaattgtgactggatcatt

atagacccttttttgtagttgttgaggtttaaagatttaagtttgttatggatgcaagct

tttcagttgaccaatgattattagccaatttctgataaaagaaaaggaaaccgattgcccc

agggctgctgttttcatttcctcattggaagaagaagcatagtatagaagaaaggcaaaca

caacacattcaacctctgccacc
```

Minimal CYBB promoter (ultra-core)

SEQ ID NO: 3

```
tttaagtttgttatggatgcaagcttttcagttgaccaatgattattagccaatttctgat

aaaagaaaaggaaaccgattgccccagggctgctgttttcatttcctcattggaagaagaa

gcatagtatagaagaaaggcaaacacaacacattcaacctctgccacc
```

-continued

Enhancer element 2

SEQ ID NO: 4 gcttagtcatgttggtcccaaagtcatagttgatgagaagtagcaagttaagagagaaaga cttctagagataggtacatacacaatgataacaagtgacatcagagaacctaaggaagggc aaagaaagaaacactgcaaagcagactcaaacacttaaaagcatagcagcttggggccagt tagtgtaagagaaaaggagctccatatgcctcaatagaacctaagagcatcattgtactgc atttattcattcattcacttcacatgtttattcaacaaatgctatgtatactgagatttt ctctggtcattgtactggctagaacctaaaggagtgagactattaattagagtttacaatc tggcaatgatattaacagtctattcacaaaagggttaactcaagttaagccggcctaaatg tttatgcaaaataggatttttgcctaagtctaaagggtatcagaaaagtgtagccattgag aatgactcatttcatggtgttctcggatggcttaagtattattaatatgtctccatttcta gtgcaggaacctccacgttttagaggaaaggaggaaagaatttgtgaagactgtgcctaaa aaaggtagaaatttgtttacaatttatttaaagataaaagtaaagaactaggttgctttaa aaaagggagggaaagaaaatcaaaatacatcttatttgaggcattaaaactttttttaagaa aataaaatttaaaataaagttgtattcttctaaaaataatttttttaaaccagctgaaaatg aaaaatgcagattatactaagaagcaactgttttacattctgctttctgaatggtatttaa aaactcagttattttcagaaatgaggaagtcttgatctgctagatgaaggtcggctgcagg tggtgtttattgctttatgatggcaacaaaccgtaaacccatcactcagtaaatattaaac tggctgaatgaatccaaagcatgtctaacatacaggaaaaacacagccctgttaagcagtc ttgaaacccacaagctacatggaaaacacagattcaactacatcataaaaattca Enhancer element 2 core

SEQ ID NO: 5 gagctccatatgcctcaatagaacctaagagcatcattgtactgcatttattcattcattc acttcacatgtttattcaacaaatgctatgtatactgagattttctctggtcattgtact ggctagaacctaaaggagtgagactattaattagagtttacaatctggcaatgatattaac agtctattcacaaaagggttaactcaagttaagccggcctaaatgtttatgcaaaatagga tttttgcctaagtctaaagggtatcagaaaagtgtagccattgagaatgactcatttcatg gtgttctcggatggcttaagtattattaatatgtctccatttctagtgcaggaacctccac gttttagaggaaaggaggaaagaatttgtgaagactgtgcctaaaaaaaggtagaaatttgt ttacaatttatttaaagataaaagtaaagaactaggttgctttaaaaaagggagggaaaga aaatcaaaatacatcttatttgaggcattaaaactttttttaagaaaataaaatttaaaata aagttgtattcttctaaaaataatttttttaaaccagctgaaaatgaaaaatgcagattata ctaagaagcaactgttttacattctgctttctgaatggtatttaaaaactcagttattttc agaaatgaggaagtcttgatctgctagatgaaggtcggctgcaggtggtgtttattgcttt atgatggcaacaaaccgtaaacccatcactcagtaaatattaaactggctgaatgaatcca aagcatgtctaacatacaggaaaaacacagccctgttaagcagtcttgaaacccacaagct acatggaaaacacagattcaactacatcataaaaattc Enhancer element 2 ultra core

SEQ ID NO: 6

Aaatcaaaatacatcttatttgaggcattaaaactttttttaagaaaataaaatttaaaata aagttgtattcttctaaaaataatttttttaaaccagctgaaaatgaaaaatgcagattata ctaagaagcaactgttttacattctgctttctgaatggtatttaaaaactcagttattttc agaaatgaggaagtcttgatctgctagatgaaggtcggctgcaggtggtgtttattgcttt -continued atgatggcaacaaaccgtaaacccatcactcagtaaatattaaactggctgaatgaatcca aagcatgtctaacatacaggaaaaacacagccctgttaagca Element 2 RELA TF binding site

SEQ ID NO: 7 aactgcccaggccatccacagatgactgtagatacatgtgtaagttcagttcacatcctca gaaccacccagatgtcctgtagatgcatgagaaatgttaaatgcttgttgttttaagccac taacttcagagtagtttgttatataacaaaaccgctgatgcaaatggcatcaaaaattgtt gaaagagagatgggggttcagggtgagagctgtaggtgattgtatctgtgctaataccaca tagcccttttttggggattgccatgaataatatattagctttgctatgagtaaaatactat atcctctgaattgtcatgaattacgtggagtcatacgtgttttggaagtgtgaaagtccct gggctcagataaaaggtgttgccatctggaaagtacaggtagtttatttcaattctgctcc aataactagcacgtcattccattcatgtagaaataagctactggctatctcactatctgaa atagaagtatgaactgtgggtaagtgggtgaggacaatgtctgagcaaccaaaaaggagct caaatcc Enhancer element 4

SEQ ID NO: 8 aaactaatatgaccttataagaggaggaagttggggcacaggcatgtacacacagaggaaa gaccatacagaggaaagaccatattaagataaaggaagaggatgaccatctacaagccaag caaaggggccccagaaggaaaccaaacatgctgaaaccttgatcttgaatttgtagcttct aaaactgtgagaaaataaatttctgttgtttaaaacatccaggctgaggtactttgttatg gaagccctgtcaaactaatgcaacaacatttcctcccattagatttcttaattcgtgtata gctggcctgataatgtcttatcagctaccccaactcaattgctgcaaatacatttttaaaa gttctggtggttgtagttgattgcacacttctgtatgagccaataatgtgaggcaagtctt taaaagggtagcacaatcagtctgaggttacaccatagatatggttaaccatagtgtggtc tccataacataggaagtcaagatccccccttcactcttgaccagtcagattgcacctagaac atttttctcaattctgcataccacatttaaagaggaagacaaaacccatgcgttgtgcagc taccacatgtcgagcatcagactatgtgcactgtgtacacttagtcctcccaccaacccaa tgaagatggtattaatacccacctcccattgtacagatgaggagactggggctaaatgagg tcaaataggttgctcaacagagatcttcacctccatggactcccatagccacactctgaac cctgtcatctctcagaagtgcactgcttctgaaatctgcatctcatacacccatcctctga ctaccacctcctgttccctggcttcctaattcactcacacccaagatgactgtccttcaac ctcatcaaactttgagttctttttgactctttgactttgctcccatcttgtgttcacttct tggcattctactcatcttagactcagttcacttctgccattttcttgcacaaatcctgaat tctctcatgcagtgcccttctgtaccacctgcaggcaaaaaccaaccctgatcaactcaat tgtcctctatacttgctcgtgggtgggtaagaaaagctagaaaagctacccacagactcct accattactgatttatgagctccaggctcaactgggcccttatctgggcctggaaatcatt ttgcatttctacagtcaagtctcctttctgaacaaaagatacaacattgaaaactgtcttc tgtttcctgaaatgtctactcactacctcactttcaacagataaccttgccctctctttca caaaggaaatggaaaccacaaagaggaagtccctcaccctgctgtccccagccctacaaat cctcctgcatctgcactctgctccttccctctttttacagagaggaggcccctcctgtcta aagcaaattccatttccttcctgccttgggctcagaaatctcaccccatccaaaatcttcc atggttagcctgtccctttgttgcgactctttctcaatatttacaagctcctatattttt aaaataataaaactaggtcctcctggtgttcacatgttttcccaattgtagccaagtcctc -continued tcattcttatcacagcctcagacattttgaggtgtctcactacctcacctcaacccacaac atctggcttccctcattgttttccagtaggcccctt Enhancer element 4R

SEQ ID NO: 9 cagagatcttcacctccatggactcccatagccacactctgaaccctgtcatctctcagaa gtgcactgcttctgaaatctgcatctcatacacccatcctctgactaccacctcctgttcc ctggcttcctaattcactcacacccaagatgactgtccttcaacctcatcaaactttgagt tctttttgactctttgactttgctcccatcttgtgttcacttcttggcattctactcatct tagactcagttcacttctgccattttcttgcacaaatcctgaattctctcatgcagtgccc ttctgtaccacctgcaggcaaaaaccaaccctgatcaactcaattgtcctctatacttgct cgtgggtgggtaagaaaagctagaaaagctacccacagactcctaccattactgatttatg agctccaggctcaactgggcccttatctgggcctggaaatcattttgcatttctacagtca agtctcctttctgaacaaaagatacaacattgaaaactgtcttctgtttcctgaaatgtct actcactacctcactttcaacagataaccttgccctctctttcacaaaggaaatggaaacc acaaagaggaagtccctcaccctgctgtccccagccctacaaatcctcctgcatctgcact ctgctccttccctctttttacagagaggaggcccctcctgtctaaagcaaattccatttcc ttcctgccttgggctcagaaatctcaccccatccaaaatcttccatggttagcctgtccct ttgttgcgactctttctcaatatttacaagctcctatatttttttaaaataataaaactagg tcctcctggtgttcacatgttttcccaattgtagccaagtcctctcattcttatcacagcc tcagacattttgaggtgtctcactacctcacctcaacccacaacatctggcttccctcatt gttttccagtaggcccctt Enhancer element 4R Core

SEQ ID NO: 10 catgcagtgcccttctgtaccacctgcaggcaaaaaccaaccctgatcaactcaattgtcc tctatacttgctcgtgggtgggtaagaaaagctagaaaagctacccacagactcctaccat tactgatttatgagctccaggctcaactgggcccttatctgggcctggaaatcattttgca tttctacagtcaagtctcctttctgaacaaaagatacaacattgaaaactgtcttctgttt cctgaaatgtctactcactacctcactttcaacagataaccttgccctctctttcacaaag gaaatggaaaccacaaagaggaagtccctcaccctgctgtccccagccctacaaatcctcc tgcatctgcactctgctccttccctctttttacagagaggaggcccctcctgtctaaagca aattccatttccttcctgccttgggctcagaaatctcaccccatccaaaatcttccatggt tagcctgtccct Enhancer element 4R ultra core

SEQ ID NO: 11 gcccttatctgggcctggaaatcattttgcatttctacagtcaagtctcctttctgaacaa aagatacaacattgaaaactgtcttctgtttcctgaaatgtctactcactacctcactttc aacagataaccttgccctctctttcacaaaggaaatggaaaccacaaagaggaagtccctc accctgctgtccccagccctacaaatcctcctgcatctgcactctgctccttccctctttt tacagagagg Enhancer element 4L

SEQ ID NO: 12 aaactaatatgaccttataagaggaggaagttggggcacaggcatgtacacacagaggaaa gaccatacagaggaaagaccatattaagataaaggaagaggatgaccatctacaagccaag caaaggggccccagaaggaaaccaaacatgctgaaaccttgatcttgaatttgtagcttct -continued aaaactgtgagaaaataaatttctgttgtttaaaacatccaggctgaggtactttgttatg gaagccctgtcaaactaatgcaacaacatttcctcccattagatttcttaattcgtgtata gctggcctgataatgtcttatcagctaccccaactcaattgctgcaaatacatttttaaaa gttctggtggttgtagttgattgcacacttctgtatgagccaataatgtgaggcaagtctt taaaagggtagcacaatcagtctgaggttacaccatagatatggttaaccatagtgtggtc tccataacataggaagtcaagatccccccttcactcttgaccagtcagattgcacctagaac atttttctcaattctgcataccacatttaaagaggaagacaaaacccatgcgttgtgcagc taccacatgtcgagcatcagactatgtgcactgtgtacacttagtcctcccaccaacccaa tgaagatggtattaatacccacctcccattgtacagatgaggagactggggctaaatgagg tcaaataggttgctcaa Enhancer element 4L core

SEQ ID NO: 13 agccaataatgtgaggcaagtctttaaaagggtagcacaatcagtctgaggttacaccata gatatggttaaccatagtgtggtctccataacataggaagtcaagatccccccttcactctt gaccagtcagattgcacctagaacatttttctcaattctgcataccacatttaaagaggaa gacaaaacccatgcgttgtgcagct Full Intron 3 Enhancer

SEQ ID NO: 14 gatcatccctccttgacttccatacatgtggggattacaggcatgagtcacctgcctggcg agttccttgtttctaaggagacacaattcatttttattctccctacccccattagaatagt ttctatttagaggaagtaaagcctgagaaacaggcaatgttttcaccaagatggcctgtta agaaatcttggttagtctacaagtccaaatttcactgccggtgagcaccatgtcccatgag cagcacatgttgtaatgccagctagaggtctcaatcattgaaactttgctttgtaatcctt ctggttacctagagaaagaaagccccagggttgcccaccccaccactccaggaaaggtagg ggtaaaggctctcagactgctttgttgagaaaaatggagaatgggtgaagctcagcacaca aaaatctctgaggaagccttaaaaacccccaacttgccatgcagaaactaatttctgtctg gatggcagtcctagtcttaagatcagaaagaaacaggaaggtgagagggtgaggttttatc tgttaccttatatagtctgggagtcagaggcactcagtgtgcctctatctttaatcacgtg gtctagcactagtctcttgggctttctgtctcatagtttttttttttagttgaaaaacagg tcaactaacacaaatgtaagaaggcatatgttggtctaaaagtatattaattgtttaagtc tgtcaattagtgagttgtcagtcaataaatatttgttgagtgccatttatgtgctaagcac tggggacatgtggtaagtaaagattaagttatagataggccatgagcttaaggagcttaga gtgttaacaggagagacagagaataaatatggaacttccaaattataaacagtgctatgca aataaggtagtgttattcatatttatcagatattctactgccagcaggtgtggatattact gtcaacttacttgcctgagttctgtagattcaaagttggattttgtaatttctcccagttg cgtataaatatctaaatcagatacattgatggtgcgtgtggtgagatcaagtgtacaaaaa gtagagcttttgagtttctgtaaagtgttacaccccataaaatatgtacttctttttagtt ccacttcccatttcttgaaatattttttttcttactcagtttcaatagagcatagaaatct gctgaagtgactcaataatctcccttgcattagaatggtagtttattgaaatcgggcaagg cttccggtgacagtaacagagaaacttccctttagaagtcaatggcagaaagtaaagtaag ttagtaaggaagctatggggcatgatggcaacgtggataattgggaagtggctggcaataa tttagaagtaactcaaagcatataaatgcaatctgcctgatgatggggaacaaaaaattat gggcagtcacagacagtaaagtccttccttcctatgccaccaaccggttgtctcgcctcct -continued tttttaaggaagtggtgaggagatggtattcttaaaagcccagtatcagcatgacttgtgg cttctttttggatttgtttgccattcctgtccacaccaaagagggtaggtgggaaaaatta gggatttgtgccctgatggttggacccactccactgatccattagttactagtaatctcac tttttcctttcaatataatatatgtgttttacattaactagctttttaaaaattacctatt aagatgaaa Middle fragment INT3 enhancer ultra core

SEQ ID NO: 15 cttaaaaacccccaacttgccatgcagaaactaatttctgtctggatggcagtcctagtct taagatcagaaagaaacaggaaggtgagagggtgaggttttatctgttaccttatatagtc tgggagtcagaggcactcagtgtgcctctatctttaatcacgtggtctagcactagtctct tgggctttctgtctcatagtttttttttttagttgaaaaacaggtcaactaacacaaatgt aagaaggcatatgttggtctaaaagtatatta INT3 enhancer right fragment ultra core

SEQ ID NO: 16

Agcttttgagtttctgtaaagtgttacaccccataaaatatgtacttctttttagttccac ttcccattttcttgaaatatttttttcttactcagtttcaatagagcatagaaatctgctg aagtgactcaataatctcccttgcattagaatggtagtttattgaaatcgggcaaggcttc cggtgacagtaacagagaaacttccctttagaagtcaatggcagaaagtaaagtaagttag taaggaagctatggggcatgatggcaacgtggataattgggaagtggctggcaataattta gaagtaactcaaagcatataaatgcaatctgcctgatgatggggaacaaaaaattatgggc agtcacagacagtaaagtccttccttcctatgccaccaaccggttgtctcgcctccttttt taaggaagtggtgagga Gp91*phox* cDNA

SEQ ID NO: 17 atggggaactgggctgtgaatgaggggctctccatttttgtcattctggtttggctggggt tgaacgtcttcctctttgtctggtattaccgggtttatgatattccacctaagttctttta cacaagaaaacttcttgggtcagcactggcactggccagggcccctgcagcctgcctgaat ttcaactgcatgctgattctcttgccagtctgtcgaaatctgctgtccttcctcaggggtt ccagtgcgtgctgctcaacaagagttcgaagacaactggacaggaatctcacctttcataa aatggtggcatggatgattgcacttcactctgcgattcacaccattgcacatctatttaat gtggaatggtgtgtgaatgcccgagtcaataattctgatccttattcagtagcactctctg aacttggagacaggcaaaatgaaagttatctcaattttgctcgaaagagaataaagaaccc tgaaggaggcctgtacctggctgtgaccctgttggcaggcatcactggagttgtcatcacg ctgtgcctcatattaattatcacttcctccaccaaaaccatccggaggtcttactttgaag tcttttggtacacacatcatctctttgtgatcttcttcattggccttgccatccatggagc tgaacgaattgtacgtgggcagaccgcagagagtttggctgtgcataatataacagtttgt gaacaaaaaatctcagaatggggaaaaataaaggaatgcccaatccctcagtttgctggaa accctcctatgacttggaaatggatagtgggtcccatgtttctgtatctctgtgagaggtt ggtgcggttttggcgatctcaacagaaggtggtcatcaccaaggtggtcactcacccttc aaaaccatcgagctacagatgaagaagaaggggttcaaaatggaagtgggacaatacattt ttgtcaagtgcccaaaggtgtccaagctggagtggcaccccttttacactgacatccgcccc tgaggaagacttctttagtatccatatccgcatcgttggggactggacagaggggctgttc aatgcttgtggctgtgataagcaggagtttcaagatgcgtggaaactacctaagatagcgg -continued ttgatgggccctttggcactgccagtgaagatgtgttcagctatgaggtggtgatgttagt gggagcagggattggggtcacacccttcgcatccattctcaagtcagtctggtacaaatat tgcaataacgccaccaatctgaagctcaaaaagatctacttctactggctgtgccgggaca cacatgcctttgagtggtttgcagatctgctgcaactgctggagagccagatgcaggaaag gaacaatgccggcttcctcagctacaacatctacctcactggctgggatgagtctcaggcc aatcactttgctgtgcaccatgatgaggagaaagatgtgatcacaggcctgaaacaaaaga ctttgtatggacggcccaactgggataatgaattcaagacaattgcaagtcaacaccctaa taccagaataggagttttcctctgtggacctgaagccttggctgaaaccctgagtaaacaa agcatctccaactctgagtctggccctcggggagtgcatttcattttcaacaaggaaaact tctaa jCAT Codon optimized Gp91$^{phox}$

SEQ ID NO: 18 atgggcaactgggccgtgaacgagggcctgagcatcttcgtgatcctggtgtggctgggcc tgaacgtgttcctgttcgtgtggtactaccgcgtgtacgacatcccccccaagttcttcta cacccgcaagctgctgggcagcgccctggccctggcccgcgcccccgccgcctgcctgaac ttcaactgcatgctgatcctgctgcccgtgtgccgcaacctgctgagcttcctgcgcggca gcagcgcctgctgcagcacccgcgtgcgccgccagctggaccgcaacctgaccttccacaa gatggtggcctggatgatcgccctgcacagcgccatccacaccatcgcccacctgttcaac gtggagtggtgcgtgaacgcccgcgtgaacaacagcgacccctacagcgtggccctgagcg agctgggcgaccgccagaacgagagctacctgaacttcgcccgcaagcgcatcaagaaccc cgagggcggcctgtacctggccgtgaccctgctggccggcatcaccggcgtggtgatcacc ctgtgcctgatcctgatcatcaccagcagcaccaa gaccatccgccgcagctacttcgaggtgttctggtacacccaccacctgt tcgtgatcttcttcatcggcctggccatccacggcgccgagcgcatcgtgcgcggccagac cgccgagagcctggccgtgcacaacatcaccgtgtgcgagcagaagatcagcgagtggggc aagatcaaggagtgccccatcccccagttcgccggcaacccccccatgacctggaagtgga tcgtgggccccatgttcctgtacctgtgcgagcgcctggtgcgcttctggcgcagccagca gaaggtggtgatcaccaaggtggtgacccaccccttcaagaccatcgagctgcagatgaag aagaagggcttcaagatggaggtgggccagtacatcttcgtgaagtgccccaaggtgagca agctggagtggcaccccttcaccctgaccagcgcccccgaggaggacttcttcagcatcca catccgcatcgtgggcgactggaccgagggcctgttcaacgcctgcggctgcgacaagcag gagttccaggacgcctggaagctgcccaagatcgccgtggacggccccttcggcaccgcca gcgaggacgtgttcagctacgaggtggtgatgctggtgggcgccggcatcggcgtgacccc cttcgccagcatcctgaagagcgtgtggtacaagtactgcaacaacgccaccaacctgaag ctgaagaagatctacttctactggctgtgccgcgacacccacgccttcgagtggttcgccg acctgctgcagctgctggagagccagatgcaggagcgcaacaacgccggcttcctgagcta caacatctacctgaccggctgggacgagagccaggccaaccacttcgccgtgcaccacgac gaggagaaggacgtgatcaccggcctgaagcagaagaccctgtacggccgccccaactggg acaacgagttcaagaccatcgccagccagcaccccaacacccgcatcggcgtgttcctgtg cggccccgaggccctggccgagaccctgagcaagcagagcatcagcaacagcgagagcggc ccccgcggcgtgcacttcatcttcaacaaggagaacttctaa -continued Clinical co-op Gp91$^{phox}$

SEQ ID NO: 19 atgggcaactgggccgtgaacgagggcctgagcatcttcgtgatcctggtgtggctgggcc tgaacgtgttcctgttcgtgtggtactaccgggtgtacgacatcccccccaagttcttcta cacccggaagctgctgggcagcgccctggccctggccagagcccctgccgcctgcctgaac ttcaactgcatgctgatcctgctgcccgtgtgccggaacctgctgtccttcctgcggggca gcagcgcctgctgcagcaccagagtgcggcggcagctggaccggaacctgaccttccacaa gatggtggcctggatgatcgccctgcacagcgccatccacaccatcgcccacctgttcaac gtggagtggtgcgtgaacgcccgggtgaacaacagcgacccctacagcgtggccctgagcg agctgggcgaccggcagaacgagagctacctgaacttcgcccggaagcggatcaagaaccc cgagggcggcctgtacctggccgtgaccctgctggccggcatcaccggcgtggtgatcacc ctgtgcctgatcctgatcatcaccagcagcaccaagaccatccggcggagctacttcgagg tgttctggtacacccaccacctgttcgtgatctttttcatcggcctggccatccacggcgc cgagcggatcgtgaggggccagaccgccgagagcctggccgtgcacaacatcaccgtgtgc gagcagaaaatcagcgagtggggcaagatcaaagagtgccccatcccccagttcgccggca acccccccatgacctggaagtggatcgtgggccccatgttcctgtacctgtgcgagcggct ggtgcggttctggcggagccagcagaaagtggtgattaccaaggtggtgacccaccccttc aagaccatcgagctgcagatgaagaaaaagggcttcaagatggaagtgggccagtacatct ttgtgaagtgccccaaggtgtccaagctggaatggcaccccttcaccctgaccagcgcccc tgaagaggacttcttcagcatccacatcagaatcgtgggcgactggaccgagggcctgttc aatgcctgcggctgcgacaagcaggaattccaggacgcctggaagctgcccaagatcgccg tggacggcccctttggcaccgccagcgaggacgtgttcagctacgaggtggtgatgctggt cggagccggcatcggcgtgaccccctttcgccagcatcctgaagagcgtgtggtacaagtac tgcaacaacgccaccaacctgaagctgaagaagatctacttctactggctgtgccgggaca cccacgccttcgagtggttcgccgatctgctgcagctgctggaaagccagatgcaggaacg gaacaacgccggcttcctgagctacaacatctacctgaccggctgggacgagagccaggcc aaccacttcgccgtgcaccacgacgaggaaaaggacgtgatcaccggcctgaagcagaaaa ccctgtacggcaggcccaactgggacaacgagtttaagaccatcgccagccagcaccccaa cacccggatcggcgtgtttctgtgcggccctgaggccctggccgagacactgagcaagcag agcatcagcaacagcgagagcggccccaggggcgtgcacttcatcttcaacaaagaaaact tctga GeneArt optimized Gp91$^{phox}$

SEQ ID NO: 20 atgggaaactgggccgtgaatgagggcctgagcatcttcgtgatcctcgtgtggctgggcc tgaacgtgttcctgttcgtgtggtactaccgggtgtacgacatccctcctaagttcttcta cacccggaagctgctgggctctgctctggctcttgctagagcaccagccgcctgcctgaac ttcaactgcatgctgatcctgctgcctgtgtgccggaacctgctgagctttctgagaggca gcagcgcctgctgtagcaccagagttagacggcagctggacagaaacctgaccttccacaa gatggtggcctggatgatcgccctgcacagcgccattcacacaatcgcccacctgttcaac gtcgagtggtgcgtgaacgccagagtgaacaacagcgacccttacagcgtggccctgagcg agctgggcgatagacagaatgagagctacctgaatttcgcccggaagcggatcaagaaccc tgaaggcggactgtacctggccgtgacactgctggctggaatcacaggcgtggtcatcacc ctgtgcctgatcctgatcatcaccagcagcaccaagaccatccggcggagctacttcgagg -continued tgttctggtacacccaccacctgtttgtgatctttttcatcggcctggccatccacggcgc
cgagagaatcgttagaggacagacagccgagtctctggccgtgcacaatatcaccgtgtgc
gagcagaaaatcagcgagtggggcaagatcaaagagtgccccattcctcagttcgccggca
atcctcctatgacctggaagtggatcgtgggccccatgttcctgtacctgtgcgaaagact
cgtgcggttctggcggagccagcagaaggtggtcattaccaaggtcgtgacacacccctttt
aagaccatcgagctgcagatgaagaaaaagggcttcaagatggaagtgggccagtacatct
ttgtgaagtgccccaaggtgtccaagctggaatggcaccccttcacactgacaagcgcccc
tgaagaggacttcttcagcatccacatccggatcgtcggcgattggaccgagggcctgttt
aatgcctgcggctgcgacaagcaagagttccaggatgcttggaagctgcccaagatcgccg
tggacggaccttttggaacagccagcgaggacgtgttcagctacgaggtcgtgatgctcgt
tggagccggcatcggcgtgacaccttttgccagcatcctgaagtctgtgtggtacaagtac
tgcaacaacgccaccaacctgaagctcaagaagatctacttctactggctgtgccgggaca
cccacgcctttgagtggttcgctgatctcctgcagctgctggaaagccagatgcaagagag
aaacaacgccggcttcctgagctacaacatctacctgaccggctgggatgagagccaggcc
aatcactttgccgtgcaccacgacgaagagaaggacgtgatcaccggcctgaagcagaaaa
ccctgtacggcagacccaactgggacaacgagttcaagacaatcgcctctcagcaccccaa
taccagaatcggagtgtttctgtgcggccctgaggctctggccgaaacactgagcaagcag
agcatcagcaacagcgagtctggccctagaggcgtgcacttcatcttcaacaaagagaact
tctga IDT optimized Gp91$^{phox}$

SEQ ID NO: 21 atgggtaactgggcagtgaacgaggggctttctatctttgtcatactcgtgtggcttggcc
tcaacgtgttcttgttcgtctggtactaccgagtgtacgacattcctcctaaattctttta
cacacgcaaactccttgggtctgctttggcgctcgctcgggcacctgcagcgtgcctgaat
tttaactgtatgctgatcctccttcctgtgtgccgaaaccttctttcattcctgcgaggta
gttccgcttgctgctcaactcgggtgcgcaggcagcttgaccgcaacctgacgttccataa
gatggtagcatggatgattgcgttgcattccgcgatccacactatcgcgcacctctttaac
gtggaatggtgtgtaaacgcgagagtaaataacagcgacccatactctgtagcactttccg
aacttggagaccggcagaacgaatcttaccttaacttcgctaggaagagaattaaaaaccc
agaaggtggcctttatctcgcggttacgctgcttgctggcattaccggcgttgtcataact
ctctgtttgatacttataattacaagctccaccaagactataagacgatcctactttgaag
tcttctggtacacgcaccacctgttcgtaattttctttataggactggctattcacggtgc
ggaaaggattgtacgaggtcagacagctgaatccctcgcggtgcacaacattacggtatgc
gagcagaagataagtgagtggggaaaaattaaagagtgccccataccacagttcgccggca
atccaccaatgacatggaagtggatcgtgggcccaatgttcctctacctgtgtgagcgcct
tgtaaggttttggcgaagccaacagaaagtagtgataacgaaagtagttacacacccgttc
aagacaatagagctccagatgaaaaaaaaaggcttcaagatggaagtcggtcaatacatat
tcgtgaagtgcccgaaagtctcaaagttggaatggcacccattcactctcacatcagcgcc
tgaagaagactttttctccattcatattcgcattgtgggcgattggacggaagggctcttt
aacgcttgcgggtgtgataaacaagagtttcaagacgcatggaaattgcctaagatagcag
ttgatggcccgttcggaaccgccagcgaagatgttttcagttacgaggtcgtcatgctcgt -continued tggtgctggaatcggagttactccgtttgcttccatacttaagagcgtctggtacaaatat tgtaataatgccaccaatttgaaactcaagaagatttacttttattggttgtgtagggata ctcacgctttcgaatggttcgcagaccttctccagctccttgaaagccaaatgcaggaacg aaataacgcaggatttttgagctacaatatataccttacgggttgggacgaatctcaggct aatcatttcgcggtacaccatgatgaagaaaaggatgttataacgggtttgaaacaaaaaa cactctatggacgacctaactgggataatgaatttaaaacaatcgccagccaacatcctaa cacccggattggagttttcctgtgcgggccagaggcactcgcggagacgctgagtaaacaa tcaattagcaactctgagtccgggccacgcggggtgcattttatttttaacaaagagaact tctag full vector

SEQ ID NO: 22

AGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACG

TCAATGGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCCAGTAC

ATGACCTTATGGGACTTTCCTACTTGGCAGTACATCTACGTATTAGTCATCGCTATTACCAT

GGTGATGCGGTTTTGGCAGTACATCAATGGGCGTGGATAGCGGTTTGACTCACGGGGATTTC

CAAGTCTCCACCCCATTGACGTCAATGGGAGTTTGTTTTGGCACCAAAATCAACGGGACTTT

CCAAAATGTCGTAACAACTCCGCCCCATTGACGCAAATGGGCGGTAGGCGTGTACGGTGGGA

GGTCTATATAAGCAGAGCTCGTTTAGTGAACCGGGGTCTCTCTGGTTAGACCAGATCTGAGC

CTGGGAGCTCTCTGGCTAACTAGGGAACCCACTGCTTAAGCCTCAATAAAGCTTGCCTTGAG

TGCTTCAAGTAGTGTGTGCCCGTCTGTTGTGTGACTCTGGTAACTAGAGATCCCTCAGACCC

TTTTAGTCAGTGTGGAAAATCTCTAGCagtggcgcccgaacagggacttgaaagcgaaaggg aaaccagaggagctctctcgacgcaggactcggcttgctgaagcgcgcacggcaagaggcga ggggcggcgactggtgagtacgccaaaaattttgactagcggaggctagaaggagagagatg ggtgcgagagcgtcagtattaagcgggggagaattagatcgcgatgggaaaaaattcggtta aggccagggggaaagaaaaaatataaattaaaacatatagtatgggcaagcagggagctaga acgattcgcagttaatcctggcctgttagaaacatcagaaggctgtagacaaatactgggac agctacaaccatcccttcagacaggatcagaagaacttagatcattatataatacagtagca accctctattgtgtgcatcaaaggatagagataaaagacaccaaggaagctttagacaagat agaggaagagcaaaacaaaagtaagaccaccgcacagcaagcggccgctgatcttcagacct ggaggaggagatatgagggacaattggagaagtgaattatataaatataaagtagtaaaaat tgaaccattaggagtagcacccaccaaggcaaagagaagagtggtgcagagagaaaaaagag cagtgggaataggagctttgttccttgggttcttgggagcagcaggaagcactatgggcgca gcgtcaatgacgctgacggtacaggccagacaattattgtctggtatagtgcagcagcagaa caatttgctgagggctattgaggcgcaacagcatctgttgcaactcacagtctggggcatca agcagctccaggcaagaatcctggctgtggaaagatacctaaaggatcaacagctcctgggg atttggggttgctctggaaaactcatttgcaccactgctgtgccttggaatgctagttggag taataaatctctggaacagatttggaatcacacgacctggatggagtgggacagagaaatta acaattacacaagcttaatacactccttaattgaagaatcgcaaaaccagcaagaaaagaat gaacaagaattattggaattagataaatgggcaagtttgtggaattggtttaacataacaaa ttggctgtggtatataaaattattcataatgatagtaggaggcttggtaggtttaagaatag -continued tttttgctgtactttctatagtgaatagagttaggcagggatattcaccattatcgtttcag acccacctcccaaccccgaggggacccgacaggcccgaaggaatagaagaagaaggtggaga gagagacagagacagatccattcgattagtgaacggatctcgacggtatcggttaacttta aaagaaaagggggggattggggggtacagtgcaggggaaagaatagtagacataatagcaaca gacatacaaactaaagaattacaaaaacaaattacaaaaattcaaaattttatcgatcacga gactagcctcgagAAATCAAAATACATCTTATTTGAGGCATTAAAACTTTTTTAAGAAAATA

AAATTTAAAATAAAGTTGTATTCTTCTAAAAATAATTTTTTAAACCAGCTGAAAATGAAAAA

TGCAGATTATACTAAGAAGCAACTGTTTTACATTCTGCTTTCTGAATGGTATTTAAAAACTC

AGTTATTTTCAGAAATGAGGAAGTCTTGATCTGCTAGATGAAGGTCGGCTGCAGGTGGTGTT

TATTGCTTTATGATGGCAACAAACCGTAAACCCATCACTCAGTAAATATTAAACTGGCTGAA

TGAATCCAAAGCATGTCTAACATACAGGAAAAACACAGCCCTGTTAAGCAGCCCTTATCTGG

GCCTGGAAATCATTTTGCATTTCTACAGTCAAGTCTCCTTTCTGAACAAAAGATACAACATT

GAAAACTGTCTTCTGTTTCCTGAAATGTCTACTCACTACCTCACTTTCAACAGATAACCTTG

CCCTCTCTTTCACAAAGGAAATGGAAACCACAAAGAGGAAGTCCCTCACCCTGCTGTCCCCA

GCCCTACAAATCCTCCTGCATCTGCACTCTGCTCCTTCCCTCTTTTTACAGAGAGGCTTAAA

AACCCCCAACTTGCCATGCAGAAACTAATTTCTGTCTGGATGGCAGTCCTAGTCTTAAGATC

AGAAAGAAACAGGAAGGTGAGAGGGTGAGGTTTTATCTGTTACCTTATATAGTCTGGGAGTC

AGAGGCACTCAGTGTGCCTCTATCTTTAATCACGTGGTCTAGCACTAGTCTCTTGGGCTTTC

TGTCTCATAGTTTTTTTTTTTAGTTGAAAAACAGGTCAACTAACACAAATGTAAGAAGGCAT

ATGTTGGTCTAAAAGTATATTAAGCTTTTGAGTTTCTGTAAAGTGTTACACCCCATAAAATA

TGTACTTCTTTTTAGTTCCACTTCCCATTTTCTTGAAATATTTTTTTCTTACTCAGTTTCAA

TAGAGCATAGAAATCTGCTGAAGTGACTCAATAATCTCCCTTGCATTAGAATGGTAGTTTAT

TGAAATCGGGCAAGGCTTCCGGTGACAGTAACAGAGAAACTTCCCTTTAGAAGTCAATGGCA

GAAAGTAAAGTAAGTTAGTAAGGAAGCTATGGGGCATGATGGCAACGTGGATAATTGGGAAG

TGGCTGGCAATAATTTAGAAGTAACTCAAAGCATATAAATGCAATCTGCCTGATGATGGGGA

ACAAAAAATTATGGGCAGTCACAGACAGTAAAGTCCTTCCTTCCTATGCCACCAACCGGTTG

TCTCGCCTCCTTTTTTAAGGAAGTGGTGAGGATTTAAGTTTGTTATGgatgcaagcttttca gttgaccaatgattattagccaatttctgataaaagaaaaggaaaccgattgccccagggct gctgttttcatttcctcattggaAGAAGAAGCATAGTATAGAAGAAAGGCAAACACAACACA

TTCAACCTCTGCCACCATGGGCAACTGGGCCGTGAACGAGGGCCTGAGCATCTTCGTGATCC

TGGTGTGGCTGGGCCTGAACGTGTTCCTGTTCGTGTGGTACTACCGCGTGTACGACATCCCC

CCCAAGTTCTTCTACACCCGCAAGCTGCTGGGCAGCGCCCTGGCCCTGGCCCGCGCCCCCGC

CGCCTGCCTGAACTTCAACTGCATGCTGATCCTGCTGCCCGTGTGCCGCAACCTGCTGAGCT

TCCTGCGCGGCAGCAGCGCCTGCTGCAGCACCCGCGTGCGCCGCCAGCTGGACCGCAACCTG

ACCTTCCACAAGATGGTGGCCTGGATGATCGCCCTGCACAGCGCCATCCACACCATCGCCCA

CCTGTTCAACGTGGAGTGGTGCGTGAACGCCCGCGTGAACAACAGCGACCCCTACAGCGTGG

CCCTGAGCGAGCTGGGCGACCGCCAGAACGAGAGCTACCTGAACTTCGCCCGCAAGCGCATC

AAGAACCCCGAGGGCGGCCTGTACCTGGCCGTGACCCTGCTGGCCGGCATCACCGGCGTGGT

GATCACCCTGTGCCTGATCCTGATCATCACCAGCAGCACCAAGACCATCCGCCGCAGCTACT

TCGAGGTGTTCTGGTACACCCACCACCTGTTCGTGATCTTCTTCATCGGCCTGGCCATCCAC

-continued

GGCGCCGAGCGCATCGTGCGCGGCCAGACCGCCGAGAGCCTGGCCGTGCACAACATCACCGT
GTGCGAGCAGAAGATCAGCGAGTGGGGCAAGATCAAGGAGTGCCCCATCCCCCAGTTCGCCG
GCAACCCCCCCATGACCTGGAAGTGGATCGTGGGCCCCATGTTCCTGTACCTGTGCGAGCGC
CTGGTGCGCTTCTGGCGCAGCCAGCAGAAGGTGGTGATCACCAAGGTGGTGACCCACCCCTT
CAAGACCATCGAGCTGCAGATGAAGAAGAAGGGCTTCAAGATGGAGGTGGGCCAGTACATCT
TCGTGAAGTGCCCCAAGGTGAGCAAGCTGGAGTGGCACCCCTTCACCCTGACCAGCGCCCCC
GAGGAGGACTTCTTCAGCATCCACATCCGCATCGTGGGCGACTGGACCGAGGGCCTGTTCAA
CGCCTGCGGCTGCGACAAGCAGGAGTTCCAGGACGCCTGGAAGCTGCCCAAGATCGCCGTGG
ACGGCCCCTTCGGCACCGCCAGCGAGGACGTGTTCAGCTACGAGGTGGTGATGCTGGTGGGC
GCCGGCATCGGCGTGACCCCCTTCGCCAGCATCCTGAAGAGCGTGTGGTACAAGTACTGCAA
CAACGCCACCAACCTGAAGCTGAAGAAGATCTACTTCTACTGGCTGTGCCGCGACACCCACG
CCTTCGAGTGGTTCGCCGACCTGCTGCAGCTGCTGGAGAGCCAGATGCAGGAGCGCAACAAC
GCCGGCTTCCTGAGCTACAACATCTACCTGACCGGCTGGGACGAGAGCCAGGCCAACCACTT
CGCCGTGCACCACGACGAGGAGAAGGACGTGATCACCGGCCTGAAGCAGAAGACCCTGTACG
GCCGCCCCAACTGGGACAACGAGTTCAAGACCATCGCCAGCCAGCACCCCAACACCCGCATC
GGCGTGTTCCTGTGCGGCCCCGAGGCCCTGGCCGAGACCCTGAGCAAGCAGAGCATCAGCAA
CAGCGAGAGCGGCCCCCGCGGCGTGCACTTCATCTTCAACAAGGAGAACTTCTAActgcagg
aattcgagcatcttaccgccatttattcccatatttgttctgtttttcttgatttgggtata
catttaaatgttaataaaacaaaatggtggggcaatcatttacatttttagggatatgtaat
tactagttcaggtgtattgccacaagacaaacatgttaagaaactttcccgttatttacgct
ctgttcctgttaatcaacctctggattacaaaatttgtgaaagattgactgatattcttaac
tatgttgctccttttacgctgtgtggatatgctgctttaatgcctctgtatcatgctattgc
ttcccgtacggctttcgttttctcctccttgtataaatcctggttgctgtctctttatgagg
agttgtggcccgttgtccgtcaacgtggcgtggtgtgctctgtgtttgctgacgcaaccccc
actggctggggcattgccaccacctgtcaactcctttctgggactttcgctttccccctccc
gatcgccacggcagaactcatcgccgcctgccttgcccgctgctggacaggggctaggttgc
tgggcactgataattccgtggtgttgtcggggaagggcctgctgccggctctgcggcctctt
ccgcgtcttcgccttcgccctcagacgagtcggatctccctttgggccgcctccccgcctgg
aattcgagctcggtacctttaagaccaatgacttacaaggcagctgtagatcttagccactt
tttaaaagaaaaggggggactggaagggctaattcactcccaacgaagacaagatctgcttt
ttgcttgtactgggtctctctggttagaccagatctgagcctgggagctctctggctaacta
gggaacctactgcttaagcctcaataaagcttgccttgagtgcttCAAGTAGTGTGTGCCCG
TCTGTTGTGTGACTCTGGTAACTAGAGATCCCTCAGACCCTTTTAGTCAGTGTGGAAAATCT
CTAGCagtagtagttcatgtcatcttattattcagtatttataacttgcaaagaaatgaata
tcagagagtgagaggaacttgtttattgcagcttataatggttacaaataaagcaatagcat
cacaaatttcacaaataaagcatttttttcactgcattctagttgtggtttgtccaaactca
tcaatgtatcttatcatgtctggctctagctatcccgcccctaactccgcccatcccgcccc
taactccgcccagttccgcccattctccgccccatggctgactaattttttttatttatgca
gaggccgaggccgcctcggcctctgagctattccagaagtagtgaggaggcttttttggagg
cctagggacgtacccaattcgccctatagtgagtcgtattacgcgcgctcactggccgtcgt
tttacaacgtcgtgactgggaaaaccctggcgttacccaacttaatcgccttgcagcacatc -continued cccctttcgccagctggcgtaatagcgaagaggcccgcaccgatcgcccttcccaacagttg cgcagcctgaatggcgaatgggacgcgccctgtagcggcgcattaagcgcggcgggtgtggt ggttacgcgcagcgtgaccgctacacttgccagcgccctagcgcccgctcctttcgctttct tcccttcctttctcgccacgttcgccggctttccccgtcaagctctaaatcgggggctccct ttagggttccgatttagtgctttacggcacctcgaccccaaaaaacttgattagggtgatgg ttcacgtagtgggccatcgccctgatagacggtttttcgccctttgacgttggagtccacgt tctttaatagtggactcttgttccaaactggaacaacactcaaccctatctcggtctattct tttgatttataagggattttgccgatttcggcctattggttaaaaaatgagctgatttaaca aaaatttaacgcgaattttaacaaaatattaacgcttacaatttaggtggcacttttcgggg aaatgtgcgcggaacccctatttgtttatttttctaaatacattcaaatatgtatccgctca tgagacaataaccctgataaatgcttcaataatagcacctagatcaagagacaggatgagga tcgtttcgcatgattgaacaagatggattgcacgcaggttctccggccgcttgggtggagag gctattcggctatgactgggcacaacagacaatcggctgctctgatgccgccgtgttccggc tgtcagcgcaggggcgcccggttctttttgtcaagaccgacctgtccggtgccctgaatgaa ctgcaagacgaggcagcgcggctatcgtggctggccacgacgggcgttccttgcgcagctgt gctcgacgttgtcactgaagcgggaagggactggctgctattgggcgaagtgccggggcagg atctcctgtcatctcaccttgctcctgccgagaaagtatccatcatggctgatgcaatgcgg cggctgcatacgcttgatccggctacctgcccattcgaccaccaagcgaaacatcgcatcga gcgagcacgtactcggatggaagccggtcttgtcgatcaggatgatctggacgaagagcatc aggggctcgcgccagccgaactgttcgccaggctcaaggcgagcatgcccgacggcgaggat ctcgtcgtgacccatggcgatgcctgcttgccgaatatcatggtggaaaatggccgcttttc tggattcatcgactgtggccggctgggtgtggcggaccgctatcaggacatagcgttggcta cccgtgatattgctgaagagcttggcggcgaatgggctgaccgcttcctcgtgctttacggt atcgccgctcccgattcgcagcgcatcgccttctatcgccttcttgacgagttcttctgaat tattaacgcttacaatttcctgatgcggtattttctccttacgcatctgtgcggtatttcac accgcatcaggtggcacttttcggggaaatgtgcgcggaacccctatttgtttatttttcta aatacattcaaatatgtatccgctcatgaccaaaatcccttaacgtgagttttcgttccact gagcgtcagaccccgtagaaaagatcaaaggatcttcttgagatcctttttttctgcgcgta atctgctgcttgcaaacaaaaaaaccaccgctaccagcggtggtttgtttgccggatcaaga gctaccaactctttttccgaaggtaactggcttcagcagagcgcagataccaaatactgttc ttctagtgtagccgtagttaggccaccacttcaagaactctgtagcaccgcctacatacctc gctctgctaatcctgttaccagtggctgctgccagtggcgataagtcgtgtcttaccgggtt ggactcaagacgatagttaccggataaggcgcagcggtcgggctgaacggggggttcgtgca cacagcccagcttggagcgaacgacctacaccgaactgagatacctacagcgtgagctatga gaaagcgccacgcttcccgaagggagaaaggcggacaggtatccggtaagcggcagggtcgg aacaggagagcgcacgagggagcttccagggggaaacgcctggtatctttatagtcctgtcg ggtttcgccacctctgacttgagcgtcgatttttgtgatgctcgtcaggggggcggagccta tggaaaaacgccagcaacgcggcctttttacggttcctggccttttgctggccttttgctca catgttctttcctgcgttatcccctgattctgtggataaccgtattaccgcctttgagtgag ctgataccgctcgccgcagccgaacgaccgagcgcagcgagtcagtgagcgaggaagcggaa -continued gagcgcccaatacgcaaaccgcctctccccgcgcgttggccgattcattaatgcagctggca cgacaggtttcccgactggaaagcgggcagtgagcgcaacgcaattaatgtgagttagctca ctcattaggcaccccaggctttacactttatgcttccggctcgtatgttgtgtggaattgtg agcggataacaatttcacacaggaaacagctatgaccatgattacgccaagcgcgcaattaa ccctcactaaagggaacaaaagct ggagctgcaagcttggccattgcatacgttgtatccatatcataatatgtacatttatattg gctcatgtccaacattaccgccatgttgacattgattattgactagttattaatagtaatca attacggggtcattagttcatagcccatatatgg

CMV:

SEQ ID NO: 23

AGTTCCGCGTTACATAACTTACGGTAAATGGCCCGCCTGGCTGACCGCCCAACGACCCCCGC

CCATTGACGTCAATAATGACGTATGTTCCCATAGTAACGCCAATAGGGACTTTCCATTGACG

TCAATGGGTGGAGTATTTACGGTAAACTGCCCACTTGGCAGTACATCAAGTGTATCATATGC

CAAGTACGCCCCCTATTGACGTCAATGACGGTAAATGGCCCGCCTGGCATTATGCCCAGTAC

ATGACCTTATGGGACTTTCCTACTTGGCAGTACATCTACGTATTAGTCATCGCTATTACCAT

GGTGATGCGGTTTTGGCAGTACATCAATGGGCGTGGATAGCGGTTTGACTCACGGGGATTTC

CAAGTCTCCACCCCATTGACGTCAATGGGAGTTTGTTTTGGCACCAAAATCAACGGGACTTT

CCAAAATGTCGTAACAACTCCGCCCCATTGACGCAAATGGGCGGTAGGCGTGTACGGTGGGA

GGTCTATATAAGCAGAGCTCGTTTAGTGAACCG

3'R/U5:

SEQ ID NO: 24

GGGTCTCTCTGGTTAGACCAGATCTGAGCCTGGGAGCTCTCTGGCTAACTAGGGAACCCACT

GCTTAAGCCTCAATAAAGCTTGCCTTGAGTGCTTCAAGTAGTGTGTGCCCGTCTGTTGTGTG

ACTCTGGTAACTAGAGATCCCTCAGACCCTTTTAGTCAGTGTGGAAAATCTCTAGC

PSI:

SEQ ID NO: 25

Tcgacgcaggactcggcttgctgaagcgcgcacggcaagaggcgaggggcggcgactggtga gtacgccaaaaattttgactagcggaggctagaaggagagagatgggtgcgagagcgtcagt attaagcgggggag

RRE:

SEQ ID NO: 26

Tccttgggttcttgggagcagcaggaagcactatgggcgcagcgtcaatgacgctgacggta caggccagacaattattgtctggtatagtgcagcagcagaacaatttgctgagggctattga ggcgcaacagcatctgttgcaactcacagtctggggcatcaagcagctccaggcaagaatcc tggctgtggaaagatacct

WPRE:

SEQ ID NO: 27

Cccatatttgttctgtttttcttgatttgggtatacatttaaatgttaataaaacaaaatgg tggggcaatcatttacatttttagggatatgtaattactagttcaggtgtattgccacaaga caaacatgttaagaaactttcccgttatttacgctctgttcctgttaatcaacctctggatt acaaaatttgtgaaagattgactgatattcttaactatgttgctccttttacgctgtgtgga tatgctgctttaatgcctctgtatcatgctattgcttcccgtacggctttcgttttctcctc cttgtataaatcctggttgctgtctctttatgaggagttgtggcccgttgtccgtcaacgtg gcgtggtgtgctctgtgtttgctgacgcaacccccactggctggggcattgccaccacctgt caactcctttctgggactttcgctttccccctcccgatcgccacggcagaactcatcgccgc ctgccttgcccgctgctggacaggggctaggttgctgggcactgataattccgtggtgttgt cggggaagggcctgctgccggctctgcggcctcttccgcgtcttcgccttcgccctcagacg agtcggatctccctttgggccgcctccccgcctgga

3' PPT:

SEQ ID NO: 28 tttttaaaagaaaaggggggac

3' delta U3/R/U5

SEQ ID NO: 29 tggaagggctaattcactcccaacgaagacaagatctgctttttgcttgtactgggtctctc tggttagaccagatctgagcctgggagctctctggctaactagggaacctactgcttaagcc tcaataaagcttgccttgagtgcttCAAGTAGTGTGTGCCCGTCTGTTGTGTGACTCTGGTA

ACTAGAGATCCCTCAGACCCTTTTAGTCAGTGTGGAAAATCTCTAGC

SV40 ori:

SEQ ID NO: 30

Atcccgcccctaactccgcccagttccgcccattctccgccccatggctgactaattttttt tatttatgcagaggccgaggccgcctcggcctctgagctattccagaagtagtgaggaggct tttttggaggcctagg KANr:

SEQ ID NO: 31

Attgaacaagatggattgcacgcaggttctccggccgcttgggtggagaggctattcggcta tgactgggcacaacagacaatcggctgctctgatgccgccgtgttccggctgtcagcgcagg ggcgcccggttctttttgtcaagaccgacctgtccggtgccctgaatgaactgcaagacgag gcagcgcggctatcgtggctggccacgacgggcgttccttgcgcagctgtgctcgacgttgt cactgaagcgggaagggactggctgctattgggcgaagtgccggggcaggatctcctgtcat ctcaccttgctcctgccgagaaagtatccatcatggctgatgcaatgcggcggctgcatacg cttgatccggctacctgcccattcgaccaccaagcgaaacatcgcatcgagcgagcacgtac tcggatggaagccggtcttgtcgatcaggatgatctggacgaagagcatcaggggctcgcgc cagccgaactgttcgccaggctcaaggcgagcatgcccgacggcgaggatctcgtcgtgacc catggcgatgcctgcttgccgaatatcatggtggaaaatggccgcttttctggattcatcga ctgtggccggctgggtgtggcggaccgctatcaggacatagcgttggctacccgtgatattg ctgaagagcttggcggcgaatgggctgaccgcttcctcgtgctttacggtatcgccgctccc gattcgcagcgcatcgccttctatcgccttcttgacgagttcttctga

COLE1:

SEQ ID NO: 32 agatcaaaggatcttcttgagatcctttttttctgcgcgtaatctgctgcttgcaaacaaaa aaaccaccgctaccagcggtggtttgtttgccggatcaagagctaccaactctttttccgaa ggtaactggcttcagcagagcgcagataccaaatactgttcttctagtgtagccgtagttag gccaccacttcaagaactctgtagcaccgcctacatacctcgctctgctaatcctgttacca gtggctgctgccagtggcgataagtcgtgtcttaccgggttggactcaagacgatagttacc ggataaggcgcagcggtcgggctgaacggggggttcgtgcacacagcccagcttggagcgaa cgacctacaccgaactgagatacctacagcgtgagctatgagaaagcgccacgcttcccgaa gggagaaaggcggacaggtatccggtaagcggcagggtcggaacaggagagcgcacgaggga gcttccagggggaaacgcctggtatctttatagtcctgtcgggtttcgccacctctgacttg agcgtcgatttttgtgatgctcgtcaggggggcggagcctatggaaaaacgccagcaacgcg

What is claimed is:

1. A recombinant lentiviral vector (LV) comprising:

an expression cassette comprising a nucleic acid construct comprising:

a CYBB promoter or effective fragment thereof; and a nucleic acid that encodes a Gp91phox operably linked to said CYBB promoter or promoter fragment thereof;

wherein said CYBB promoter or effective fragment thereof comprises the nucleic acid sequence of SEQ ID NO: 3; and wherein said expression cassette further comprises regulatory nucleic acid sequences comprising enhancers consisting of SEQ ID NO: 6 and SEQ ID NO: 11 for expression of the nucleic acid that encodes the Gp91phox operably linked to said CYBB promoter.

2. The vector of claim 1, wherein said vector shows high expression in CD33+ (bulk myeloid cells), high expression in CD19+ B cells, high expression in CD66b+CD15+ CD11b+CD16+ (mature neutrophils), and low or no expression in CD3+ T cells.

3. A host cell transduced with a vector of claim 1.

4. The host cell of claim 3, wherein:

said cell is a stem cell; and/or said cell is a stem cell derived from bone marrow, and/or from umbilical cord blood, and/or from peripheral blood; and/or said cell is a human hematopoietic progenitor cell; and/or said cell is a human hematopoietic progenitor cell that is a CD34+ cell.

5. A method of treating a chronic granulomatous disease (X-CGD) in a subject, said method comprising:

transducing a stem cell and/or progenitor cell from said subject with a vector of claim 1; and transplanting said transduced cell or cells derived therefrom into said subject where said cells or derivatives therefrom express said $Gp91^{phox}$.

6. The method of claim 5, wherein:

said cell is a stem cell; and/or said cell is a stem cell derived from bone marrow; and/or said cell is a human hematopoietic stem and progenitor cell; and/or said cell is a human hematopoietic stem and progenitor cell that is a $CD34^+$ cell.

7. A recombinant lentiviral vector (LV) comprising SEQ ID NO: 22.

8. The vector of claim 7, wherein said vector shows high expression in CD33+ (bulk myeloid cells), high expression in CD19+B cells, high expression in CD66b+CD15+ CD11b+CD16+ (mature neutrophils), and low or no expression in CD3+ T cells.

9. A host cell transduced with a vector of claim 7.

10. The host cell of claim 9, wherein:

said cell is a stem cell; and/or said cell is a stem cell derived from bone marrow, and/or from umbilical cord blood, and/or from peripheral blood; and/or said cell is a human hematopoietic progenitor cell; and/or said cell is a human hematopoietic progenitor cell that is a CD34+ cell.

11. A method of treating a chronic granulomatous disease (X-CGD), in a subject, said method comprising:

transducing a stem cell and/or progenitor cell from said subject with a vector of claim 7; and transplanting said transduced cell or cells derived therefrom into said subject where said cells or derivatives therefrom express said $Gp91^{phox}$.

12. The method of claim 11, wherein:

said cell is a stem cell; and/or said cell is a stem cell derived from bone marrow; and/or said cell is a human hematopoietic stem and progenitor cell; and/or said cell is a human hematopoietic stem and progenitor cell that is a $CD34^+$ cell.

* * * * *

SEQUENCE LISTING

<160> NUMBER OF SEQ ID NOS: 32

<210> SEQ ID NO 1
<211> LENGTH: 507
<212> TYPE: DNA
<213> ORGANISM: Homo sapiens

<400> SEQUENCE: 1
tagcacataa aattggcaca tattaagcat tttgtaaata tcaaccatta caattgttac 60
tacttttctc agcaaggcta tgaatgctgt tccagcctgt caaaatcaca cctgtttaat 120
gtgttttacc cagcacgaag tcatgtctag ttgagtggct taaaaattgt gatcaaatag 180
ctggttagtt aaaaagttat ttcactgtgt aaaatacatc ccttaaaatg cactgttatt 240
tatctcttag ttgtagaaat tggtttcatt ttccactatg tttaattgtg actggatcat 300
tatagaccct ttttttgtag ttgttgaggt ttaaagattt aagtttgtta tggatgcaag 360
cttttcagtt gaccaatgat tattagccaa tttctgataa aagaaaagga aaccgattgc 420
cccagggctg ctgttttcat ttcctcattg gaagaagaag catagtatag aagaaaggca 480
aacacaacac attcaacctc tgccacc 507

<210> SEQ ID NO 2
<211> LENGTH: 267
<212> TYPE: DNA
<213> ORGANISM: Artificial
<220> FEATURE:
<223> OTHER INFORMATION: Reduced CYBB promonter

<400> SEQUENCE: 2
tatctcttag ttgtagaaat tggtttcatt ttccactatg tttaattgtg actggatcat 60
tatagaccct ttttttgtag ttgttgaggt ttaaagattt aagtttgtta tggatgcaag 120
cttttcagtt gaccaatgat tattagccaa tttctgataa aagaaaagga aaccgattgc 180
cccagggctg ctgttttcat ttcctcattg gaagaagaag catagtatag aagaaaggca 240
aacacaacac attcaacctc tgccacc 267

<210> SEQ ID NO 3
<211> LENGTH: 170
<212> TYPE: DNA
<213> ORGANISM: Artificial
<220> FEATURE:
<223> OTHER INFORMATION: CYBB reduced enhancer element

<400> SEQUENCE: 3
tttaagtttg ttatggatgc aagcttttca gttgaccaat gattattagc caatttctga 60
taaaagaaaa ggaaaccgat tgccccaggg ctgctgtttt catttcctca ttggaagaag 120
aagcatagta tagaagaaag gcaaacacaa cacattcaac ctctgccacc 170

<210> SEQ ID NO 4
<211> LENGTH: 1092
<212> TYPE: DNA
<213> ORGANISM: Homo sapiens

<400> SEQUENCE: 4
gcttagtcat gttggtccca aagtcatagt tgatgagaag tagcaagtta agagagaaag 60
acttctagag ataggtacat acacaatgat aacaagtgac atcagagaac ctaaggaagg 120
gcaaagaaag aaacactgca aagcagactc aaacacttaa aagcatagca gcttggggcc 180
agttagtgta agagaaaagg agctccatat gcctcaatag aacctaagag catcattgta 240

```
ctgcatttat tcattcattc acttcacatg tttattcaac aaatgctatg tatactgaga    300
tttttctctg gtcattgtac tggctagaac ctaaaggagt gagactatta attagagttt    360
acaatctggc aatgatatta acagtctatt cacaaaaggg ttaactcaag ttaagccggc    420
ctaaatgttt atgcaaaata ggatttttgc ctaagtctaa agggtatcag aaaagtgtag    480
ccattgagaa tgactcattt catggtgttc tcggatggct taagtattat taatatgtct    540
ccatttctag tgcaggaacc tccacgtttt agaggaaagg aggaaagaat ttgtgaagac    600
tgtgcctaaa aaaggtagaa atttgtttac aatttattta aagataaaag taaagaacta    660
ggttgcttta aaaaagggag ggaaagaaaa tcaaaataca tcttatttga ggcattaaaa    720
ctttttttaag aaaataaaat ttaaaataaa gttgtattct tctaaaaata attttttaaa    780
ccagctgaaa atgaaaaatg cagattatac taagaagcaa ctgttttaca ttctgctttc    840
tgaatggtat ttaaaaactc agttattttc agaaatgagg aagtcttgat ctgctagatg    900
aaggtcggct gcaggtggtg tttattgctt tatgatggca acaaaccgta aacccatcac    960
tcagtaaata ttaaactggc tgaatgaatc caaagcatgt ctaacataca ggaaaaacac   1020
agccctgtta agcagtcttg aaacccacaa gctacatgga aaacacagat tcaactacat   1080
cataaaaatt ca                                                       1092
```

<210> SEQ ID NO 5
<211> LENGTH: 892
<212> TYPE: DNA
<213> ORGANISM: Artificial
<220> FEATURE:
<223> OTHER INFORMATION: CYBB reduced enhancer element

<400> SEQUENCE: 5

```
gagctccata tgcctcaata gaacctaaga gcatcattgt actgcattta ttcattcatt     60
cacttcacat gtttattcaa caaatgctat gtatactgag atttttctct ggtcattgta    120
ctggctagaa cctaaaggag tgagactatt aattagagtt tacaatctgg caatgatatt    180
aacagtctat tcacaaaagg gttaactcaa gttaagccgg cctaaatgtt tatgcaaaat    240
aggatttttg cctaagtcta aagggtatca gaaaagtgta gccattgaga atgactcatt    300
tcatggtgtt ctcggatggc ttaagtatta ttaatatgtc tccatttcta gtgcaggaac    360
ctccacgttt tagaggaaag gaggaaagaa tttgtgaaga ctgtgcctaa aaaaggtaga    420
aatttgttta caatttattt aaagataaaa gtaaagaact aggttgcttt aaaaaaggga    480
gggaaagaaa atcaaaatac atcttatttg aggcattaaa actttttttaa gaaaataaaa    540
tttaaaataa agttgtattc ttctaaaaat aattttttaa accagctgaa aatgaaaaat    600
gcagattata ctaagaagca actgttttac attctgcttt ctgaatggta tttaaaaact    660
cagttatttt cagaaatgag gaagtcttga tctgctagat gaaggtcggc tgcaggtggt    720
gtttattgct ttatgatggc aacaaaccgt aaacccatca ctcagtaaat attaaactgg    780
ctgaatgaat ccaaagcatg tctaacatac aggaaaaaca cagccctgtt aagcagtctt    840
gaaacccaca agctacatgg aaaacacaga ttcaactaca tcataaaaat tc            892
```

<210> SEQ ID NO 6
<211> LENGTH: 347
<212> TYPE: DNA
<213> ORGANISM: Artificial
<220> FEATURE:
<223> OTHER INFORMATION: CYBB reduced enhancer element

<400> SEQUENCE: 6
aaatcaaaat acatcttatt tgaggcatta aaactttttt aagaaaataa aatttaaaat 60
aaagttgtat tcttctaaaa ataatttttt aaaccagctg aaaatgaaaa atgcagatta 120
tactaagaag caactgtttt acattctgct ttctgaatgg tatttaaaaa ctcagttatt 180
ttcagaaatg aggaagtctt gatctgctag atgaaggtcg gctgcaggtg gtgtttattg 240
ctttatgatg gcaacaaacc gtaaacccat cactcagtaa atattaaact ggctgaatga 300
atccaaagca tgtctaacat acaggaaaaa cacagccctg ttaagca 347

<210> SEQ ID NO 7
<211> LENGTH: 556
<212> TYPE: DNA
<213> ORGANISM: Artificial
<220> FEATURE:
<223> OTHER INFORMATION: Modified CYBB enhancer element

<400> SEQUENCE: 7
aactgcccag gccatccaca gatgactgta gatacatgtg taagttcagt tcacatcctc 60
agaaccaccc agatgtcctg tagatgcatg agaaatgtta aatgcttgtt gttttaagcc 120
actaacttca gagtagtttg ttatataaca aaaccgctga tgcaaatggc atcaaaaatt 180
gttgaaagag agatgggggt tcagggtgag agctgtaggt gattgtatct gtgctaatac 240
cacatagccc tttttttgggg attgccatga ataatatatt agctttgcta tgagtaaaat 300
actatatcct ctgaattgtc atgaattacg tggagtcata cgtgttttgg aagtgtgaaa 360
gtccctgggc tcagataaaa ggtgttgcca tctggaaagt acaggtagtt tatttcaatt 420
ctgctccaat aactagcacg tcattccatt catgtagaaa taagctactg gctatctcac 480
tatctgaaat agaagtatga actgtgggta agtgggtgag gacaatgtct gagcaaccaa 540
aaaggagctc aaatcc 556

<210> SEQ ID NO 8
<211> LENGTH: 1744
<212> TYPE: DNA
<213> ORGANISM: Artificial
<220> FEATURE:
<223> OTHER INFORMATION: CYBB reduced enhancer element

<400> SEQUENCE: 8
aaactaatat gaccttataa gaggaggaag ttggggcaca ggcatgtaca cacagaggaa 60
agaccataca gaggaaagac catattaaga taaaggaaga ggatgaccat ctacaagcca 120
agcaaagggg ccccagaagg aaaccaaaca tgctgaaacc ttgatcttga atttgtagct 180
tctaaaactg tgagaaaata aatttctgtt gtttaaaaca tccaggctga ggtactttgt 240
tatggaagcc ctgtcaaact aatgcaacaa catttcctcc cattagattt cttaattcgt 300
gtatagctgg cctgataatg tcttatcagc taccccaact caattgctgc aaatacattt 360
ttaaaagttc tggtggttgt agttgattgc acacttctgt atgagccaat aatgtgaggc 420
aagtctttaa aagggtagca caatcagtct gaggttacac catagatatg gttaaccata 480
gtgtggtctc cataacatag gaagtcaaga tccccccttca ctcttgacca gtcagattgc 540
acctagaaca tttttctcaa ttctgcatac cacatttaaa gaggaagaca aaacccatgc 600
gttgtgcagc taccacatgt cgagcatcag actatgtgca ctgtgtacac ttagtcctcc 660
caccaaccca atgaagatgg tattaatacc cacctcccat tgtacagatg aggagactgg 720
ggctaaatga ggtcaaatag gttgctcaac agagatcttc acctccatgg actcccatag 780

```
ccacactctg aaccctgtca tctctcagaa gtgcactgct tctgaaatct gcatctcata    840

cacccatcct ctgactacca cctcctgttc cctggcttcc taattcactc acacccaaga    900

tgactgtcct tcaacctcat caaactttga gttcttttg actctttgac tttgctccca    960

tcttgtgttc acttcttggc attctactca tcttagactc agttcacttc tgccattttc   1020

ttgcacaaat cctgaattct ctcatgcagt gcccttctgt accacctgca ggcaaaaacc   1080

aaccctgatc aactcaattg tcctctatac ttgctcgtgg gtgggtaaga aaagctagaa   1140

aagctaccca cagactccta ccattactga tttatgagct ccaggctcaa ctgggccctt   1200

atctgggcct ggaaatcatt ttgcatttct acagtcaagt ctcctttctg aacaaaagat   1260

acaacattga aaactgtctt ctgtttcctg aaatgtctac tcactacctc actttcaaca   1320

gataaccttg ccctctcttt cacaaaggaa atggaaacca caaagaggaa gtccctcacc   1380

ctgctgtccc cagccctaca aatcctcctg catctgcact ctgctccttc cctcttttta   1440

cagagaggag gcccctcctg tctaaagcaa attccatttc cttcctgcct tgggctcaga   1500

aatctcaccc catccaaaat cttccatggt tagcctgtcc ctttgttgcg actctttctc   1560

aatatttaca agctcctata ttttttaaaa taataaaact aggtcctcct ggtgttcaca   1620

tgttttccca attgtagcca agtcctctca ttcttatcac agcctcagac attttgaggt   1680

gtctcactac ctcacctcaa cccacaacat ctggcttccc tcattgtttt ccagtaggcc   1740

cctt                                                                1744
```

```
<210> SEQ ID NO 9
<211> LENGTH: 995
<212> TYPE: DNA
<213> ORGANISM: Artificial
<220> FEATURE:
<223> OTHER INFORMATION: CYBB reduced enhancer element

<400> SEQUENCE: 9

cagagatctt cacctccatg gactcccata gccacactct gaaccctgtc atctctcaga     60

agtgcactgc ttctgaaatc tgcatctcat acacccatcc tctgactacc acctcctgtt    120

ccctggcttc ctaattcact cacacccaag atgactgtcc ttcaacctca tcaaactttg    180

agttcttttt gactctttga ctttgctccc atcttgtgtt cacttcttgg cattctactc    240

atcttagact cagttcactt ctgccatttt cttgcacaaa tcctgaattc tctcatgcag    300

tgcccttctg taccacctgc aggcaaaaac caaccctgat caactcaatt gtcctctata    360

cttgctcgtg ggtgggtaag aaaagctaga aaagctaccc acagactcct accattactg    420

atttatgagc tccaggctca actgggccct tatctgggcc tggaaatcat tttgcatttc    480

tacagtcaag tctcctttct gaacaaaaga tacaacattg aaaactgtct tctgtttcct    540

gaaatgtcta ctcactacct cactttcaac agataacctt gccctctctt tcacaaagga    600

aatggaaacc acaaagagga agtccctcac cctgctgtcc ccagccctac aaatcctcct    660

gcatctgcac tctgctcctt ccctcttttt acagagagga ggcccctcct gtctaaagca    720

aattccattt ccttcctgcc ttgggctcag aaatctcacc ccatccaaaa tcttccatgg    780

ttagcctgtc cctttgttgc gactctttct caatatttac aagctcctat atttttttaaa    840

ataataaaac taggtcctcc tggtgttcac atgttttccc aattgtagcc aagtcctctc    900

attcttatca cagcctcaga cattttgagg tgtctcacta cctcacctca acccacaaca    960

tctggcttcc ctcattgttt tccagtaggc ccctt                               995
```

<210> SEQ ID NO 10
<211> LENGTH: 500
<212> TYPE: DNA
<213> ORGANISM: Artificial
<220> FEATURE:
<223> OTHER INFORMATION: CYBB reduced enhancer element

<400> SEQUENCE: 10
catgcagtgc ccttctgtac cacctgcagg caaaaaccaa ccctgatcaa ctcaattgtc 60
ctctatactt gctcgtgggt gggtaagaaa agctagaaaa gctacccaca gactcctacc 120
attactgatt tatgagctcc aggctcaact gggcccttat ctgggcctgg aaatcatttt 180
gcatttctac agtcaagtct cctttctgaa caaaagatac aacattgaaa actgtcttct 240
gtttcctgaa atgtctactc actacctcac tttcaacaga taaccttgcc ctctctttca 300
caaaggaaat ggaaaccaca aagaggaagt ccctcaccct gctgtcccca gccctacaaa 360
tcctcctgca tctgcactct gctccttccc tctttttaca gagaggaggc ccctcctgtc 420
taaagcaaat tccatttcct tcctgccttg ggctcagaaa tctcacccca tccaaaatct 480
tccatggtta gcctgtccct 500

<210> SEQ ID NO 11
<211> LENGTH: 254
<212> TYPE: DNA
<213> ORGANISM: Artificial
<220> FEATURE:
<223> OTHER INFORMATION: CYBB reduced enhancer element

<400> SEQUENCE: 11
gcccttatct gggcctggaa atcattttgc atttctacag tcaagtctcc tttctgaaca 60
aaagatacaa cattgaaaac tgtcttctgt ttcctgaaat gtctactcac tacctcactt 120
tcaacagata accttgccct ctctttcaca aaggaaatgg aaaccacaaa gaggaagtcc 180
ctcaccctgc tgtccccagc cctacaaatc ctcctgcatc tgcactctgc tccttccctc 240
tttttacaga gagg 254

<210> SEQ ID NO 12
<211> LENGTH: 749
<212> TYPE: DNA
<213> ORGANISM: Artificial
<220> FEATURE:
<223> OTHER INFORMATION: CYBB reduced enhancer element

<400> SEQUENCE: 12
aaactaatat gaccttataa gaggaggaag ttggggcaca ggcatgtaca cacagaggaa 60
agaccataca gaggaaagac catattaaga taaaggaaga ggatgaccat ctacaagcca 120
agcaaagggg ccccagaagg aaaccaaaca tgctgaaacc ttgatcttga atttgtagct 180
tctaaaactg tgagaaaata aatttctgtt gtttaaaaca tccaggctga ggtactttgt 240
tatggaagcc ctgtcaaact aatgcaacaa catttcctcc cattagattt cttaattcgt 300
gtatagctgg cctgataatg tcttatcagc taccccaact caattgctgc aaatacattt 360
ttaaaagttc tggtggttgt agttgattgc acacttctgt atgagccaat aatgtgaggc 420
aagtctttaa aagggtagca caatcagtct gaggttacac catagatatg gttaaccata 480
gtgtggtctc cataacatag gaagtcaaga tccccccttca ctcttgacca gtcagattgc 540
acctagaaca tttttctcaa ttctgcatac cacatttaaa gaggaagaca aaacccatgc 600
gttgtgcagc taccacatgt cgagcatcag actatgtgca ctgtgtacac ttagtcctcc 660
caccaaccca atgaagatgg tattaatacc cacctcccat tgtacagatg aggagactgg 720
ggctaaatga ggtcaaatag gttgctcaa 749

<210> SEQ ID NO 13
<211> LENGTH: 208
<212> TYPE: DNA
<213> ORGANISM: Artificial
<220> FEATURE:
<223> OTHER INFORMATION: CYBB reduced enhancer element

<400> SEQUENCE: 13
agccaataat gtgaggcaag tctttaaaag ggtagcacaa tcagtctgag gttacaccat 60
agatatggtt aaccatagtg tggtctccat aacataggaa gtcaagatcc cccttcactc 120
ttgaccagtc agattgcacc tagaacattt ttctcaattc tgcataccac atttaaagag 180
gaagacaaaa cccatgcgtt gtgcagct 208

<210> SEQ ID NO 14
<211> LENGTH: 1778
<212> TYPE: DNA
<213> ORGANISM: Homo sapiens

<400> SEQUENCE: 14
gatcatccct ccttgacttc catacatgtg gggattacag gcatgagtca cctgcctggc 60
gagttccttg tttctaagga gacacaattc atttttattc tccctacccc cattagaata 120
gtttctattt agaggaagta aagcctgaga aacaggcaat gttttcacca agatggcctg 180
ttaagaaatc ttggttagtc tacaagtcca aatttcactg ccggtgagca ccatgtccca 240
tgagcagcac atgttgtaat gccagctaga ggtctcaatc attgaaactt tgctttgtaa 300
tccttctggt tacctagaga aagaaagccc cagggttgcc caccccacca ctccaggaaa 360
ggtaggggta aaggctctca gactgctttg ttgagaaaaa tggagaatgg gtgaagctca 420
gcacacaaaa atctctgagg aagccttaaa aacccccaac ttgccatgca gaaactaatt 480
tctgtctgga tggcagtcct agtcttaaga tcagaaagaa acaggaaggt gagagggtga 540
ggttttatct gttaccttat atagtctggg agtcagaggc actcagtgtg cctctatctt 600
taatcacgtg gtctagcact agtctcttgg gctttctgtc tcatagtttt ttttttagt 660 tgaaaaacag gtcaactaac acaaatgtaa gaaggcatat gttggtctaa aagtatatta 720
attgtttaag tctgtcaatt agtgagttgt cagtcaataa atatttgttg agtgccattt 780
atgtgctaag cactggggac atgtggtaag taaagattaa gttatagata ggccatgagc 840
ttaaggagct tagagtgtta acaggagaga cagagaataa atatggaact tccaaattat 900
aaacagtgct atgcaaataa ggtagtgtta ttcatattta tcagatattc tactgccagc 960
aggtgtggat attactgtca acttacttgc ctgagttctg tagattcaaa gttggatttt 1020
gtaatttctc ccagttgcgt ataaatatct aaatcagata cattgatggt gcgtgtggtg 1080
agatcaagtg tacaaaaagt agagcttttg agtttctgta aagtgttaca ccccataaaa 1140
tatgtacttc tttttagttc cacttcccat tttcttgaaa tattttttc ttactcagtt 1200 tcaatagagc atagaaatct gctgaagtga ctcaataatc tcccttgcat tagaatggta 1260
gtttattgaa atcgggcaag gcttccggtg acagtaacag agaaacttcc ctttagaagt 1320
caatggcaga aagtaaagta agttagtaag gaagctatgg ggcatgatgg caacgtggat 1380
aattgggaag tggctggcaa taatttagaa gtaactcaaa gcatataaat gcaatctgcc 1440

```
tgatgatggg gaacaaaaaa ttatgggcag tcacagacag taaagtcctt ccttcctatg   1500

ccaccaaccg gttgtctcgc ctccttttttt aaggaagtgg tgaggagatg gtattcttaa   1560

aagcccagta tcagcatgac ttgtggcttc tttttggatt tgtttgccat tcctgtccac   1620

accaaagagg gtaggtggga aaaattaggg atttgtgccc tgatggttgg acccactcca   1680

ctgatccatt agttactagt aatctcactt tttcctttca atataatata tgtgttttac   1740

attaactagc tttttaaaaa ttacctatta agatgaaa                           1778
```

<210> SEQ ID NO 15
<211> LENGTH: 276
<212> TYPE: DNA
<213> ORGANISM: Artificial
<220> FEATURE:
<223> OTHER INFORMATION: CYBB reduced enhancer element

<400> SEQUENCE: 15

```
cttaaaaacc cccaacttgc catgcagaaa ctaatttctg tctggatggc agtcctagtc     60

ttaagatcag aaagaaacag gaaggtgaga gggtgaggtt ttatctgtta ccttatatag    120

tctgggagtc agaggcactc agtgtgcctc tatctttaat cacgtggtct agcactagtc    180

tcttgggctt tctgtctcat agtttttttt tttagttgaa aaacaggtca actaacacaa    240

atgtaagaag gcatatgttg gtctaaaagt atatta                              276
```

<210> SEQ ID NO 16
<211> LENGTH: 444
<212> TYPE: DNA
<213> ORGANISM: Artificial
<220> FEATURE:
<223> OTHER INFORMATION: CYBB reduced enhancer element

<400> SEQUENCE: 16

```
agcttttgag tttctgtaaa gtgttacacc ccataaaata tgtacttctt tttagttcca     60

cttcccattt tcttgaaata tttttttctt actcagtttc aatagagcat agaaatctgc    120

tgaagtgact caataatctc ccttgcatta gaatggtagt ttattgaaat cgggcaaggc    180

ttccggtgac agtaacagag aaacttccct ttagaagtca atggcagaaa gtaaagtaag    240

ttagtaagga agctatgggg catgatggca acgtggataa ttgggaagtg gctggcaata    300

atttagaagt aactcaaagc atataaatgc aatctgcctg atgatgggga acaaaaaatt    360

atgggcagtc acagacagta aagtccttcc ttcctatgcc accaaccggt tgtctcgcct    420

cctttttaa ggaagtggtg agga                                            444
```

<210> SEQ ID NO 17
<211> LENGTH: 1713
<212> TYPE: DNA
<213> ORGANISM: Artificial
<220> FEATURE:
<223> OTHER INFORMATION: Gp91phox (CYBB) cDNA

<400> SEQUENCE: 17

```
atggggaact gggctgtgaa tgaggggctc tccatttttg tcattctggt ttggctgggg     60

ttgaacgtct tcctctttgt ctggtattac cgggtttatg atattccacc taagttcttt    120

tacacaagaa aacttcttgg gtcagcactg gcactggcca gggcccctgc agcctgcctg    180

aatttcaact gcatgctgat tctcttgcca gtctgtcgaa atctgctgtc cttcctcagg    240

ggttccagtg cgtgctgctc aacaagagtt cgaagacaac tggacaggaa tctcaccttt    300

cataaaatgg tggcatggat gattgcactt cactctgcga ttcacaccat tgcacatcta    360
```

tttaatgtgg aatggtgtgt gaatgcccga gtcaataatt ctgatcctta ttcagtagca 420
ctctctgaac ttggagacag gcaaaatgaa agttatctca attttgctcg aaagagaata 480
aagaaccctg aaggaggcct gtacctggct gtgaccctgt tggcaggcat cactggagtt 540
gtcatcacgc tgtgcctcat attaattatc acttcctcca ccaaaaccat ccggaggtct 600
tactttgaag tcttttggta cacacatcat ctctttgtga tcttcttcat tggccttgcc 660
atccatggag ctgaacgaat tgtacgtggg cagaccgcag agagtttggc tgtgcataat 720
ataacagttt gtgaacaaaa aatctcagaa tggggaaaaa taaaggaatg cccaatccct 780
cagtttgctg gaaaccctcc tatgacttgg aaatggatag tgggtcccat gtttctgtat 840
ctctgtgaga ggttggtgcg gttttggcga tctcaacaga aggtggtcat caccaaggtg 900
gtcactcacc ctttcaaaac catcgagcta cagatgaaga agaaggggtt caaaatggaa 960
gtgggacaat acatttttgt caagtgccca aaggtgtcca agctggagtg gcaccctttt 1020
acactgacat ccgcccctga ggaagacttc tttagtatcc atatccgcat cgttggggac 1080
tggacagagg ggctgttcaa tgcttgtggc tgtgataagc aggagtttca agatgcgtgg 1140
aaactaccta agatagcggt tgatgggccc tttggcactg ccagtgaaga tgtgttcagc 1200
tatgaggtgg tgatgttagt gggagcaggg attggggtca cacccttcgc atccattctc 1260
aagtcagtct ggtacaaata ttgcaataac gccaccaatc tgaagctcaa aaagatctac 1320
ttctactggc tgtgccggga cacacatgcc tttgagtggt ttgcagatct gctgcaactg 1380
ctggagagcc agatgcagga aaggaacaat gccggcttcc tcagctacaa catctacctc 1440
actggctggg atgagtctca ggccaatcac tttgctgtgc accatgatga ggagaaagat 1500
gtgatcacag gcctgaaaca aaagactttg tatggacggc ccaactggga taatgaattc 1560
aagacaattg caagtcaaca ccctaatacc agaataggag ttttcctctg tggacctgaa 1620
gccttggctg aaaccctgag taaacaaagc atctccaact ctgagtctgg ccctcgggga 1680
gtgcatttca ttttcaacaa ggaaaacttc taa 1713

<210> SEQ ID NO 18
<211> LENGTH: 1713
<212> TYPE: DNA
<213> ORGANISM: Artificial
<220> FEATURE:
<223> OTHER INFORMATION: Codon optimized Gp91phox

<400> SEQUENCE: 18
atgggcaact gggccgtgaa cgagggcctg agcatcttcg tgatcctggt gtggctgggc 60
ctgaacgtgt tcctgttcgt gtggtactac cgcgtgtacg acatcccccc caagttcttc 120
tacacccgca agctgctggg cagcgccctg gccctggccc gcgcccccgc cgcctgcctg 180
aacttcaact gcatgctgat cctgctgccc gtgtgccgca acctgctgag cttcctgcgc 240
ggcagcagcg cctgctgcag cacccgcgtg cgccgccagc tggaccgcaa cctgaccttc 300
cacaagatgg tggcctggat gatcgccctg cacagcgcca tccacaccat cgcccacctg 360
ttcaacgtgg agtggtgcgt gaacgcccgc gtgaacaaca gcgaccccta cagcgtggcc 420
ctgagcgagc tgggcgaccg ccagaacgag agctacctga acttcgcccg caagcgcatc 480
aagaaccccg agggcggcct gtacctggcc gtgaccctgc tggccggcat caccggcgtg 540
gtgatcaccc tgtgcctgat cctgatcatc accagcagca ccaagaccat ccgccgcagc 600
tacttcgagg tgttctggta cacccaccac ctgttcgtga tcttcttcat cggcctggcc 660
atccacggcg ccgagcgcat cgtgcgcggc cagaccgccg agagcctggc cgtgcacaac 720
atcaccgtgt gcgagcagaa gatcagcgag tggggcaaga tcaaggagtg ccccatcccc 780
cagttcgccg gcaacccccc catgacctgg aagtggatcg tgggccccat gttcctgtac 840
ctgtgcgagc gcctggtgcg cttctggcgc agccagcaga aggtggtgat caccaaggtg 900
gtgacccacc ccttcaagac catcgagctg cagatgaaga agaagggctt caagatggag 960
gtgggccagt acatcttcgt gaagtgcccc aaggtgagca agctggagtg gcacccccttc 1020 accctgacca gcgcccccga ggaggacttc ttcagcatcc acatccgcat cgtgggcgac 1080
tggaccgagg gcctgttcaa cgcctgcggc tgcgacaagc aggagttcca ggacgcctgg 1140
aagctgccca agatcgccgt ggacggcccc ttcggcaccg ccagcgagga cgtgttcagc 1200
tacgaggtgg tgatgctggt gggcgccggc atcggcgtga ccccccttcgc cagcatcctg 1260 aagagcgtgt ggtacaagta ctgcaacaac gccaccaacc tgaagctgaa gaagatctac 1320
ttctactggc tgtgccgcga cacccacgcc ttcgagtggt tcgccgacct gctgcagctg 1380
ctggagagcc agatgcagga gcgcaacaac gccggcttcc tgagctacaa catctacctg 1440
accggctggg acgagagcca ggccaaccac ttcgccgtgc accacgacga ggagaaggac 1500
gtgatcaccg gcctgaagca gaagaccctg tacggccgcc ccaactggga caacgagttc 1560
aagaccatcg ccagccagca ccccaacacc cgcatcggcg tgttcctgtg cggccccgag 1620
gccctggccg agaccctgag caagcagagc atcagcaaca gcgagagcgg cccccgcggc 1680
gtgcacttca tcttcaacaa ggagaacttc taa 1713

<210> SEQ ID NO 19
<211> LENGTH: 1713
<212> TYPE: DNA
<213> ORGANISM: Artificial
<220> FEATURE:
<223> OTHER INFORMATION: Codon optimized Gp91phox

<400> SEQUENCE: 19
atgggcaact gggccgtgaa cgagggcctg agcatcttcg tgatcctggt gtggctgggc 60
ctgaacgtgt tcctgttcgt gtggtactac cgggtgtacg acatcccccc caagttcttc 120
tacacccgga agctgctggg cagcgccctg gccctggcca gagcccctgc cgcctgcctg 180
aacttcaact gcatgctgat cctgctgccc gtgtgccgga acctgctgtc cttcctgcgg 240
ggcagcagcg cctgctgcag caccagagtg cggcggcagc tggaccggaa cctgaccttc 300
cacaagatgg tggcctggat gatcgccctg cacagcgcca tccacaccat cgcccacctg 360
ttcaacgtgg agtggtgcgt gaacgcccgg gtgaacaaca gcgacccccta cagcgtggcc 420 ctgagcgagc tgggcgaccg gcagaacgag agctacctga acttcgcccg gaagcggatc 480
aagaaccccg agggcggcct gtacctggcc gtgaccctgc tggccggcat caccggcgtg 540
gtgatcaccc tgtgcctgat cctgatcatc accagcagca ccaagaccat ccggcggagc 600
tacttcgagg tgttctggta cacccaccac ctgttcgtga tctttttcat cggcctggcc 660
atccacggcg ccgagcggat cgtgaggggc cagaccgccg agagcctggc cgtgcacaac 720
atcaccgtgt gcgagcagaa aatcagcgag tggggcaaga tcaaagagtg ccccatcccc 780
cagttcgccg gcaacccccc catgacctgg aagtggatcg tgggccccat gttcctgtac 840
ctgtgcgagc ggctggtgcg gttctggcgg agccagcaga aagtggtgat taccaaggtg 900
gtgacccacc ccttcaagac catcgagctg cagatgaaga aaaagggctt caagatggaa 960
gtgggccagt acatctttgt gaagtgcccc aaggtgtcca agctggaatg gcacccccttc 1020 accctgacca gcgcccctga agaggacttc ttcagcatcc acatcagaat cgtgggcgac 1080
tggaccgagg gcctgttcaa tgcctgcggc tgcgacaagc aggaattcca ggacgcctgg 1140
aagctgccca agatcgccgt ggacggcccc tttggcaccg ccagcgagga cgtgttcagc 1200
tacgaggtgg tgatgctggt cggagccggc atcggcgtga ccccccttcgc cagcatcctg 1260 aagagcgtgt ggtacaagta ctgcaacaac gccaccaacc tgaagctgaa gaagatctac 1320
ttctactggc tgtgccggga cacccacgcc ttcgagtggt tcgccgatct gctgcagctg 1380
ctggaaagcc agatgcagga acggaacaac gccggcttcc tgagctacaa catctacctg 1440
accggctggg acgagagcca ggccaaccac ttcgccgtgc accacgacga ggaaaaggac 1500
gtgatcaccg gcctgaagca gaaaaccctg tacggcaggc ccaactggga caacgagttt 1560
aagaccatcg ccagccagca ccccaacacc cggatcggcg tgtttctgtg cggccctgag 1620
gccctggccg agacactgag caagcagagc atcagcaaca gcgagagcgg ccccaggggc 1680
gtgcacttca tcttcaacaa agaaaacttc tga 1713

<210> SEQ ID NO 20
<211> LENGTH: 1713
<212> TYPE: DNA
<213> ORGANISM: Artificial
<220> FEATURE:
<223> OTHER INFORMATION: Codon optimized Gp91phox

<400> SEQUENCE: 20
atgggaaact gggccgtgaa tgagggcctg agcatcttcg tgatcctcgt gtggctgggc 60
ctgaacgtgt tcctgttcgt gtggtactac cgggtgtacg acatccctcc taagttcttc 120
tacacccgga agctgctggg ctctgctctg gctcttgcta gagcaccagc cgcctgcctg 180
aacttcaact gcatgctgat cctgctgcct gtgtgccgga acctgctgag ctttctgaga 240
ggcagcagcg cctgctgtag caccagagtt agacggcagc tggacagaaa cctgaccttc 300
cacaagatgg tggcctggat gatcgccctg cacagcgcca ttcacacaat cgcccacctg 360
ttcaacgtcg agtggtgcgt gaacgccaga gtgaacaaca gcgacccttca cagcgtggcc 420 ctgagcgagc tgggcgatag acagaatgag agctacctga atttcgcccg gaagcggatc 480
aagaaccctg aaggcggact gtacctggcc gtgacactgc tggctggaat cacaggcgtg 540
gtcatcaccc tgtgcctgat cctgatcatc accagcagca ccaagaccat ccggcggagc 600
tacttcgagg tgttctggta cacccaccac ctgtttgtga tctttttcat cggcctggcc 660
atccacggcg ccgagagaat cgttagagga cagacagccg agtctctggc cgtgcacaat 720
atcaccgtgt gcgagcagaa aatcagcgag tggggcaaga tcaaagagtg ccccattcct 780
cagttcgccg gcaatcctcc tatgacctgg aagtggatcg tgggccccat gttcctgtac 840
ctgtgcgaaa gactcgtgcg gttctggcgg agccagcaga aggtggtcat taccaaggtc 900
gtgacacacc cctttaagac catcgagctg cagatgaaga aaaagggctt caagatggaa 960
gtgggccagt acatctttgt gaagtgcccc aaggtgtcca agctggaatg gcacccccttc 1020 acactgacaa gcgcccctga agaggacttc ttcagcatcc acatccggat cgtcggcgat 1080
tggaccgagg gcctgtttaa tgcctgcggc tgcgacaagc aagagttcca ggatgcttgg 1140
aagctgccca agatcgccgt ggacggacct tttggaacag ccagcgagga cgtgttcagc 1200
tacgaggtcg tgatgctcgt tggagccggc atcggcgtga caccttttgc cagcatcctg 1260
aagtctgtgt ggtacaagta ctgcaacaac gccaccaacc tgaagctcaa gaagatctac 1320

```
ttctactggc tgtgccggga cacccacgcc tttgagtggt tcgctgatct cctgcagctg   1380

ctggaaagcc agatgcaaga gagaaacaac gccggcttcc tgagctacaa catctacctg   1440

accggctggg atgagagcca ggccaatcac tttgccgtgc accacgacga agagaaggac   1500

gtgatcaccg gcctgaagca gaaaaccctg tacggcagac ccaactggga caacgagttc   1560

aagacaatcg cctctcagca ccccaatacc agaatcggag tgtttctgtg cggccctgag   1620

gctctggccg aaacactgag caagcagagc atcagcaaca gcgagtctgg ccctagaggc   1680

gtgcacttca tcttcaacaa agagaacttc tga                                1713
```

<210> SEQ ID NO 21
<211> LENGTH: 1713
<212> TYPE: DNA
<213> ORGANISM: Artificial
<220> FEATURE:
<223> OTHER INFORMATION: Codon optimized Gp91phox

<400> SEQUENCE: 21

```
atgggtaact gggcagtgaa cgaggggctt tctatctttg tcatactcgt gtggcttggc     60

ctcaacgtgt tcttgttcgt ctggtactac cgagtgtacg acattcctcc taaattcttt    120

tacacacgca aactccttgg gtctgctttg gcgctcgctc gggcacctgc agcgtgcctg    180

aattttaact gtatgctgat cctccttcct gtgtgccgaa accttctttc attcctgcga    240

ggtagttccg cttgctgctc aactcgggtg cgcaggcagc ttgaccgcaa cctgacgttc    300

cataagatgg tagcatggat gattgcgttg cattccgcga tccacactat cgcgcacctc    360

tttaacgtgg aatggtgtgt aaacgcgaga gtaaataaca gcgacccata ctctgtagca    420

ctttccgaac ttggagaccg gcagaacgaa tcttacctta acttcgctag gaagagaatt    480

aaaaacccag aaggtggcct ttatctcgcg gttacgctgc ttgctggcat taccggcgtt    540

gtcataactc tctgtttgat acttataatt acaagctcca ccaagactat aagacgatcc    600

tactttgaag tcttctggta cacgcaccac ctgttcgtaa ttttctttat aggactggct    660

attcacggtg cggaaaggat tgtacgaggt cagacagctg aatccctcgc ggtgcacaac    720

attacggtat gcgagcagaa gataagtgag tggggaaaaa ttaaagagtg ccccatacca    780

cagttcgccg gcaatccacc aatgacatgg aagtggatcg tgggcccaat gttcctctac    840

ctgtgtgagc gccttgtaag gttttggcga agccaacaga aagtagtgat aacgaaagta    900

gttacacacc cgttcaagac aatagagctc cagatgaaaa aaaaaggctt caagatggaa    960

gtcggtcaat acatattcgt gaagtgcccg aaagtctcaa agttggaatg gcacccattc   1020

actctcacat cagcgcctga agaagacttt ttctccattc atattcgcat tgtgggcgat   1080

tggacggaag ggctctttaa cgcttgcggg tgtgataaac aagagtttca agacgcatgg   1140

aaattgccta agatagcagt tgatggcccg ttcggaaccg ccagcgaaga tgttttcagt   1200

tacgaggtcg tcatgctcgt tggtgctgga atcggagtta ctccgtttgc ttccatactt   1260

aagagcgtct ggtacaaata ttgtaataat gccaccaatt tgaaactcaa gaagatttac   1320

ttttattggt tgtgtaggga tactcacgct ttcgaatggt tcgcagacct tctccagctc   1380

cttgaaagcc aaatgcagga acgaaataac gcaggatttt tgagctacaa tatatacctt   1440

acgggttggg acgaatctca ggctaatcat ttcgcggtac accatgatga agaaaaggat   1500

gttataacgg gtttgaaaca aaaaacactc tatggacgac ctaactggga taatgaattt   1560

aaaacaatcg ccagccaaca tcctaacacc cggattggag ttttcctgtg cgggccagag   1620

gcactcgcgg agacgctgag taaacaatca attagcaact ctgagtccgg gccacgcggg   1680
```

gtgcatttta tttttaacaa agagaacttc tag 1713

<210> SEQ ID NO 22
<211> LENGTH: 9854
<212> TYPE: DNA
<213> ORGANISM: Artificial
<220> FEATURE:
<223> OTHER INFORMATION: Lentiviral vector

<400> SEQUENCE: 22
agttccgcgt tacataactt acggtaaatg gcccgcctgg ctgaccgccc aacgaccccc 60
gcccattgac gtcaataatg acgtatgttc ccatagtaac gccaataggg actttccatt 120
gacgtcaatg ggtggagtat ttacggtaaa ctgcccactt ggcagtacat caagtgtatc 180
atatgccaag tacgccccct attgacgtca atgacggtaa atggcccgcc tggcattatg 240
cccagtacat gaccttatgg gactttccta cttggcagta catctacgta ttagtcatcg 300
ctattaccat ggtgatgcgg ttttggcagt acatcaatgg gcgtggatag cggtttgact 360
cacggggatt tccaagtctc caccccattg acgtcaatgg gagtttgttt tggcaccaaa 420
atcaacggga ctttccaaaa tgtcgtaaca actccgcccc attgacgcaa atgggcggta 480
ggcgtgtacg gtgggaggtc tatataagca gagctcgttt agtgaaccgg ggtctctctg 540
gttagaccag atctgagcct gggagctctc tggctaacta gggaacccac tgcttaagcc 600
tcaataaagc ttgccttgag tgcttcaagt agtgtgtgcc cgtctgttgt gtgactctgg 660
taactagaga tccctcagac ccttttagtc agtgtggaaa atctctagca gtggcgcccg 720
aacagggact tgaaagcgaa agggaaacca gaggagctct ctcgacgcag gactcggctt 780
gctgaagcgc gcacggcaag aggcgagggg cggcgactgg tgagtacgcc aaaaattttg 840
actagcggag gctagaagga gagagatggg tgcgagagcg tcagtattaa gcgggggaga 900
attagatcgc gatgggaaaa aattcggtta aggccagggg gaaagaaaaa atataaatta 960
aaacatatag tatgggcaag cagggagcta gaacgattcg cagttaatcc tggcctgtta 1020
gaaacatcag aaggctgtag acaaatactg ggacagctac aaccatccct tcagacagga 1080
tcagaagaac ttagatcatt atataataca gtagcaaccc tctattgtgt gcatcaaagg 1140
atagagataa aagacaccaa ggaagcttta gacaagatag aggaagagca aaacaaaagt 1200
aagaccaccg cacagcaagc ggccgctgat cttcagacct ggaggaggag atatgaggga 1260
caattggaga agtgaattat ataaatataa agtagtaaaa attgaaccat taggagtagc 1320
acccaccaag gcaaagagaa gagtggtgca gagagaaaaa agagcagtgg gaataggagc 1380
tttgttcctt gggttcttgg gagcagcagg aagcactatg ggcgcagcgt caatgacgct 1440
gacggtacag gccagacaat tattgtctgg tatagtgcag cagcagaaca atttgctgag 1500
ggctattgag gcgcaacagc atctgttgca actcacagtc tggggcatca agcagctcca 1560
ggcaagaatc ctggctgtgg aaagatacct aaaggatcaa cagctcctgg ggatttgggg 1620
ttgctctgga aaactcattt gcaccactgc tgtgccttgg aatgctagtt ggagtaataa 1680
atctctggaa cagatttgga atcacacgac ctggatggag tgggacagag aaattaacaa 1740
ttacacaagc ttaatacact ccttaattga agaatcgcaa aaccagcaag aaaagaatga 1800
acaagaatta ttggaattag ataaatgggc aagtttgtgg aattggttta acataacaaa 1860
ttggctgtgg tatataaaat tattcataat gatagtagga ggcttggtag gtttaagaat 1920
agtttttgct gtactttcta tagtgaatag agttaggcag ggatattcac cattatcgtt 1980

```
tcagacccac ctcccaaccc cgaggggacc cgacaggccc gaaggaatag aagaagaagg   2040
tggagagaga gacagagaca gatccattcg attagtgaac ggatctcgac ggtatcggtt   2100
aacttttaaa agaaaagggg ggattggggg gtacagtgca ggggaaagaa tagtagacat   2160
aatagcaaca gacatacaaa ctaaagaatt acaaaaacaa attacaaaaa ttcaaaattt   2220
tatcgatcac gagactagcc tcgagaaatc aaaatacatc ttatttgagg cattaaaact   2280
tttttaagaa aataaaattt aaaataaagt tgtattcttc taaaaataat tttttaaacc   2340
agctgaaaat gaaaaatgca gattatacta agaagcaact gttttacatt ctgctttctg   2400
aatggtattt aaaaactcag ttattttcag aaatgaggaa gtcttgatct gctagatgaa   2460
ggtcggctgc aggtggtgtt tattgcttta tgatggcaac aaaccgtaaa cccatcactc   2520
agtaaatatt aaactggctg aatgaatcca aagcatgtct aacatacagg aaaaacacag   2580
ccctgttaag cagcccttat ctgggcctgg aaatcatttt gcatttctac agtcaagtct   2640
cctttctgaa caaaagatac aacattgaaa actgtcttct gtttcctgaa atgtctactc   2700
actacctcac tttcaacaga taaccttgcc ctctctttca caaaggaaat ggaaaccaca   2760
aagaggaagt ccctcaccct gctgtcccca gccctacaaa tcctcctgca tctgcactct   2820
gctccttccc tctttttaca gagaggctta aaaacccccca acttgccatg cagaaactaa   2880
tttctgtctg gatggcagtc ctagtcttaa gatcagaaag aaacaggaag gtgagagggt   2940
gaggttttat ctgttacctt atatagtctg ggagtcagag gcactcagtg tgcctctatc   3000
tttaatcacg tggtctagca ctagtctctt gggctttctg tctcatagtt ttttttttta   3060
gttgaaaaac aggtcaacta acacaaatgt aagaaggcat atgttggtct aaaagtatat   3120
taagcttttg agtttctgta aagtgttaca ccccataaaa tatgtacttc tttttagttc   3180
cacttcccat tttcttgaaa tatttttttc ttactcagtt tcaatagagc atagaaatct   3240
gctgaagtga ctcaataatc tcccttgcat tagaatggta gtttattgaa atcgggcaag   3300
gcttccggtg acagtaacag agaaacttcc ctttagaagt caatggcaga aagtaaagta   3360
agttagtaag gaagctatgg ggcatgatgg caacgtggat aattgggaag tggctggcaa   3420
taatttagaa gtaactcaaa gcatataaat gcaatctgcc tgatgatggg gaacaaaaaa   3480
ttatgggcag tcacagacag taaagtcctt ccttcctatg ccaccaaccg gttgtctcgc   3540
ctcctttttt aaggaagtgg tgaggattta agtttgttat ggatgcaagc ttttcagttg   3600
accaatgatt attagccaat ttctgataaa agaaaaggaa accgattgcc ccagggctgc   3660
tgttttcatt tcctcattgg aagaagaagc atagtataga agaaaggcaa acacaacaca   3720
ttcaacctct gccaccatgg gcaactgggc cgtgaacgag ggcctgagca tcttcgtgat   3780
cctggtgtgg ctgggcctga acgtgttcct gttcgtgtgg tactaccgcg tgtacgacat   3840
ccccccccaag ttcttctaca cccgcaagct gctgggcagc gccctggccc tggcccgcgc   3900
ccccgccgcc tgcctgaact tcaactgcat gctgatcctg ctgcccgtgt gccgcaacct   3960
gctgagcttc ctgcgcggca gcagcgcctg ctgcagcacc cgcgtgcgcc gccagctgga   4020
ccgcaacctg accttccaca agatggtggc ctggatgatc gccctgcaca gcgccatcca   4080
caccatcgcc cacctgttca acgtggagtg gtgcgtgaac gcccgcgtga acaacagcga   4140
cccctacagc gtggccctga gcgagctggg cgaccgccag aacgagagct acctgaactt   4200
cgcccgcaag cgcatcaaga accccgaggg cggcctgtac ctggccgtga ccctgctggc   4260
cggcatcacc ggcgtggtga tcaccctgtg cctgatcctg atcatcacca gcagcaccaa   4320
gaccatccgc cgcagctact tcgaggtgtt ctggtacacc caccacctgt tcgtgatctt   4380
```

```
cttcatcggc ctggccatcc acggcgccga gcgcatcgtg cgcggccaga ccgccgagag   4440
cctggccgtg cacaacatca ccgtgtgcga gcagaagatc agcgagtggg gcaagatcaa   4500
ggagtgcccc atcccccagt tcgccggcaa cccccccatg acctggaagt ggatcgtggg   4560
ccccatgttc ctgtacctgt gcgagcgcct ggtgcgcttc tggcgcagcc agcagaaggt   4620
ggtgatcacc aaggtggtga cccacccctt caagaccatc gagctgcaga tgaagaagaa   4680
gggcttcaag atggaggtgg gccagtacat cttcgtgaag tgccccaagg tgagcaagct   4740
ggagtggcac cccttcaccc tgaccagcgc ccccgaggag gacttcttca gcatccacat   4800
ccgcatcgtg ggcgactgga ccgagggcct gttcaacgcc tgcggctgcg acaagcagga   4860
gttccaggac gcctggaagc tgcccaagat cgccgtggac ggccccttcg gcaccgccag   4920
cgaggacgtg ttcagctacg aggtggtgat gctggtgggc gccggcatcg gcgtgacccc   4980
cttcgccagc atcctgaaga gcgtgtggta caagtactgc aacaacgcca ccaacctgaa   5040
gctgaagaag atctacttct actggctgtg ccgcgacacc cacgccttcg agtggttcgc   5100
cgacctgctg cagctgctgg agagccagat gcaggagcgc aacaacgccg gcttcctgag   5160
ctacaacatc tacctgaccg gctgggacga gagccaggcc aaccacttcg ccgtgcacca   5220
cgacgaggag aaggacgtga tcaccggcct gaagcagaag accctgtacg gccgccccaa   5280
ctgggacaac gagttcaaga ccatcgccag ccagcacccc aacacccgca tcggcgtgtt   5340
cctgtgcggc cccgaggccc tggccgagac cctgagcaag cagagcatca gcaacagcga   5400
gagcggcccc cgcggcgtgc acttcatctt caacaaggag aacttctaac tgcaggaatt   5460
cgagcatctt accgccattt attcccatat ttgttctgtt tttcttgatt tgggtataca   5520
tttaaatgtt aataaaacaa aatggtgggg caatcattta catttttagg gatatgtaat   5580
tactagttca ggtgtattgc cacaagacaa acatgttaag aaactttccc gttatttacg   5640
ctctgttcct gttaatcaac ctctggatta caaaatttgt gaaagattga ctgatattct   5700
taactatgtt gctcctttta cgctgtgtgg atatgctgct ttaatgcctc tgtatcatgc   5760
tattgcttcc cgtacggctt tcgttttctc ctccttgtat aaatcctggt tgctgtctct   5820
ttatgaggag ttgtggcccg ttgtccgtca acgtggcgtg gtgtgctctg tgtttgctga   5880
cgcaaccccc actggctggg gcattgccac cacctgtcaa ctcctttctg ggactttcgc   5940
tttccccctc ccgatcgcca cggcagaact catcgccgcc tgccttgccc gctgctggac   6000
aggggctagg ttgctgggca ctgataattc cgtggtgttg tcggggaagg gcctgctgcc   6060
ggctctgcgg cctcttccgc gtcttcgcct tcgccctcag acgagtcgga tctccctttg   6120
ggccgcctcc ccgcctggaa ttcgagctcg gtacctttaa gaccaatgac ttacaaggca   6180
gctgtagatc ttagccactt tttaaaagaa aaggggggac tggaagggct aattcactcc   6240
caacgaagac aagatctgct ttttgcttgt actgggtctc tctggttaga ccagatctga   6300
gcctgggagc tctctggcta actagggaac ctactgctta agcctcaata aagcttgcct   6360
tgagtgcttc aagtagtgtg tgcccgtctg ttgtgtgact ctggtaacta gagatccctc   6420
agaccctttt agtcagtgtg gaaaatctct agcagtagta gttcatgtca tcttattatt   6480
cagtatttat aacttgcaaa gaaatgaata tcagagagtg agaggaactt gtttattgca   6540
gcttataatg gttacaaata aagcaatagc atcacaaatt tcacaaataa agcattttttt   6600
tcactgcatt ctagttgtgg tttgtccaaa ctcatcaatg tatcttatca tgtctggctc   6660
tagctatccc gcccctaact ccgcccatcc cgcccctaac tccgcccagt tccgcccatt   6720
```

```
ctccgcccca tggctgacta atttttttta tttatgcaga ggccgaggcc gcctcggcct   6780
ctgagctatt ccagaagtag tgaggaggct tttttggagg cctagggacg tacccaattc   6840
gccctatagt gagtcgtatt acgcgcgctc actggccgtc gttttacaac gtcgtgactg   6900
ggaaaaccct ggcgttaccc aacttaatcg ccttgcagca catccccctt tcgccagctg   6960
gcgtaatagc gaagaggccc gcaccgatcg cccttcccaa cagttgcgca gcctgaatgg   7020
cgaatgggac gcgccctgta gcggcgcatt aagcgcggcg ggtgtggtgg ttacgcgcag   7080
cgtgaccgct acacttgcca gcgccctagc gcccgctcct ttcgctttct tcccttcctt   7140
tctcgccacg ttcgccggct ttccccgtca agctctaaat cgggggctcc ctttagggtt   7200
ccgatttagt gctttacggc acctcgaccc caaaaaactt gattagggtg atggttcacg   7260
tagtgggcca tcgccctgat agacggtttt tcgccctttg acgttggagt ccacgttctt   7320
taatagtgga ctcttgttcc aaactggaac aacactcaac cctatctcgg tctattcttt   7380
tgatttataa gggattttgc cgatttcggc ctattggtta aaaaatgagc tgatttaaca   7440
aaaatttaac gcgaatttta acaaaatatt aacgcttaca atttaggtgg cacttttcgg   7500
ggaaatgtgc gcggaacccc tatttgttta tttttctaaa tacattcaaa tatgtatccg   7560
ctcatgagac aataaccctg ataaatgctt caataatagc acctagatca agagacagga   7620
tgaggatcgt ttcgcatgat tgaacaagat ggattgcacg caggttctcc ggccgcttgg   7680
gtggagaggc tattcggcta tgactgggca caacagacaa tcggctgctc tgatgccgcc   7740
gtgttccggc tgtcagcgca ggggcgcccg gttctttttg tcaagaccga cctgtccggt   7800
gccctgaatg aactgcaaga cgaggcagcg cggctatcgt ggctggccac gacgggcgtt   7860
ccttgcgcag ctgtgctcga cgttgtcact gaagcgggaa gggactggct gctattgggc   7920
gaagtgccgg ggcaggatct cctgtcatct caccttgctc ctgccgagaa agtatccatc   7980
atggctgatg caatgcggcg gctgcatacg cttgatccgg ctacctgccc attcgaccac   8040
caagcgaaac atcgcatcga gcgagcacgt actcggatgg aagccggtct tgtcgatcag   8100
gatgatctgg acgaagagca tcaggggctc gcgccagccg aactgttcgc caggctcaag   8160
gcgagcatgc ccgacggcga ggatctcgtc gtgacccatg gcgatgcctg cttgccgaat   8220
atcatggtgg aaaatggccg cttttctgga ttcatcgact gtggccggct gggtgtggcg   8280
gaccgctatc aggacatagc gttggctacc cgtgatattg ctgaagagct tggcggcgaa   8340
tgggctgacc gcttcctcgt gctttacggt atcgccgctc ccgattcgca gcgcatcgcc   8400
ttctatcgcc ttcttgacga gttcttctga attattaacg cttacaattt cctgatgcgg   8460
tattttctcc ttacgcatct gtgcggtatt tcacaccgca tcaggtggca cttttcgggg   8520
aaatgtgcgc ggaaccccta tttgtttatt tttctaaata cattcaaata tgtatccgct   8580
catgaccaaa atcccttaac gtgagttttc gttccactga gcgtcagacc ccgtagaaaa   8640
gatcaaagga tcttcttgag atcctttttt tctgcgcgta atctgctgct tgcaaacaaa   8700
aaaaccaccg ctaccagcgg tggtttgttt gccggatcaa gagctaccaa ctctttttcc   8760
gaaggtaact ggcttcagca gagcgcagat accaaatact gttcttctag tgtagccgta   8820
gttaggccac cacttcaaga actctgtagc accgcctaca tacctcgctc tgctaatcct   8880
gttaccagtg gctgctgcca gtggcgataa gtcgtgtctt accgggttgg actcaagacg   8940
atagttaccg gataaggcgc agcggtcggg ctgaacgggg ggttcgtgca cacagcccag   9000
cttggagcga acgacctaca ccgaactgag atacctacag cgtgagctat gagaaagcgc   9060
cacgcttccc gaagggagaa aggcggacag gtatccggta agcggcaggg tcggaacagg   9120
```

```
agagcgcacg agggagcttc cagggggaaa cgcctggtat ctttatagtc ctgtcgggtt   9180

tcgccacctc tgacttgagc gtcgattttt gtgatgctcg tcaggggggc ggagcctatg   9240

gaaaaacgcc agcaacgcgg cctttttacg gttcctggcc ttttgctggc cttttgctca   9300

catgttcttt cctgcgttat cccctgattc tgtggataac cgtattaccg cctttgagtg   9360

agctgatacc gctcgccgca gccgaacgac cgagcgcagc gagtcagtga gcgaggaagc   9420

ggaagagcgc ccaatacgca aaccgcctct ccccgcgcgt tggccgattc attaatgcag   9480

ctggcacgac aggtttcccg actggaaagc gggcagtgag cgcaacgcaa ttaatgtgag   9540

ttagctcact cattaggcac cccaggcttt acactttatg cttccggctc gtatgttgtg   9600

tggaattgtg agcggataac aatttcacac aggaaacagc tatgaccatg attacgccaa   9660

gcgcgcaatt aaccctcact aaagggaaca aaagctggag ctgcaagctt ggccattgca   9720

tacgttgtat ccatatcata atatgtacat ttatattggc tcatgtccaa cattaccgcc   9780

atgttgacat tgattattga ctagttatta atagtaatca attacggggt cattagttca   9840

tagcccatat atgg                                                     9854
```

```
<210> SEQ ID NO 23
<211> LENGTH: 529
<212> TYPE: DNA
<213> ORGANISM: Artificial
<220> FEATURE:
<223> OTHER INFORMATION: CMV promoter

<400> SEQUENCE: 23

agttccgcgt tacataactt acggtaaatg gcccgcctgg ctgaccgccc aacgaccccc     60

gcccattgac gtcaataatg acgtatgttc ccatagtaac gccaataggg actttccatt    120

gacgtcaatg ggtggagtat ttacggtaaa ctgcccactt ggcagtacat caagtgtatc    180

atatgccaag tacgccccct attgacgtca atgacggtaa atggcccgcc tggcattatg    240

cccagtacat gaccttatgg gactttccta cttggcagta catctacgta ttagtcatcg    300

ctattaccat ggtgatgcgg ttttggcagt acatcaatgg gcgtggatag cggtttgact    360

cacggggatt tccaagtctc caccccattg acgtcaatgg gagtttgttt tggcaccaaa    420

atcaacggga ctttccaaaa tgtcgtaaca actccgcccc attgacgcaa atgggcggta    480

ggcgtgtacg gtgggaggtc tatataagca gagctcgttt agtgaaccg                529
```

```
<210> SEQ ID NO 24
<211> LENGTH: 180
<212> TYPE: DNA
<213> ORGANISM: Artificial
<220> FEATURE:
<223> OTHER INFORMATION: Component of lentiviral vector

<400> SEQUENCE: 24

gggtctctct ggttagacca gatctgagcc tgggagctct ctggctaact agggaaccca     60

ctgcttaagc ctcaataaag cttgccttga gtgcttcaag tagtgtgtgc ccgtctgttg    120

tgtgactctg gtaactagag atccctcaga cccttttagt cagtgtggaa aatctctagc    180
```

```
<210> SEQ ID NO 25
<211> LENGTH: 138
<212> TYPE: DNA
<213> ORGANISM: Artificial
<220> FEATURE:
<223> OTHER INFORMATION: Packaging signal in lentiviral vector
```

<400> SEQUENCE: 25
tcgacgcagg actcggcttg ctgaagcgcg cacggcaaga ggcgaggggc ggcgactggt 60
gagtacgcca aaaattttga ctagcggagg ctagaaggag agagatgggt gcgagagcgt 120
cagtattaag cgggggag 138

<210> SEQ ID NO 26
<211> LENGTH: 205
<212> TYPE: DNA
<213> ORGANISM: Artificial
<220> FEATURE:
<223> OTHER INFORMATION: RRE in lentiviral vector

<400> SEQUENCE: 26
tccttgggtt cttgggagca gcaggaagca ctatgggcgc agcgtcaatg acgctgacgg 60
tacaggccag acaattattg tctggtatag tgcagcagca gaacaatttg ctgagggcta 120
ttgaggcgca acagcatctg ttgcaactca cagtctgggg catcaagcag ctccaggcaa 180
gaatcctggc tgtggaaaga tacct 205

<210> SEQ ID NO 27
<211> LENGTH: 656
<212> TYPE: DNA
<213> ORGANISM: Artificial
<220> FEATURE:
<223> OTHER INFORMATION: WPRE in lentiviral vector

<400> SEQUENCE: 27
cccatatttg ttctgttttt cttgatttgg gtatacattt aaatgttaat aaaacaaaat 60
ggtggggcaa tcatttacat ttttagggat atgtaattac tagttcaggt gtattgccac 120
aagacaaaca tgttaagaaa ctttcccgtt atttacgctc tgttcctgtt aatcaacctc 180
tggattacaa aatttgtgaa agattgactg atattcttaa ctatgttgct ccttttacgc 240
tgtgtggata tgctgcttta atgcctctgt atcatgctat tgcttcccgt acggctttcg 300
ttttctcctc cttgtataaa tcctggttgc tgtctcttta tgaggagttg tggcccgttg 360
tccgtcaacg tggcgtggtg tgctctgtgt ttgctgacgc aacccccact ggctggggca 420
ttgccaccac ctgtcaactc ctttctggga ctttcgcttt ccccctcccg atcgccacgg 480
cagaactcat cgccgcctgc cttgcccgct gctggacagg ggctaggttg ctgggcactg 540
ataattccgt ggtgttgtcg gggaagggcc tgctgccggc tctgcggcct cttccgcgtc 600
ttcgccttcg ccctcagacg agtcggatct ccctttgggc cgcctccccg cctgga 656

<210> SEQ ID NO 28
<211> LENGTH: 22
<212> TYPE: DNA
<213> ORGANISM: Artificial
<220> FEATURE:
<223> OTHER INFORMATION: PPT in lentiviral vector

<400> SEQUENCE: 28
tttttaaaag aaaagggggg ac 22

<210> SEQ ID NO 29
<211> LENGTH: 233
<212> TYPE: DNA
<213> ORGANISM: Artificial
<220> FEATURE:
<223> OTHER INFORMATION: Component of lentiviral vector

<400> SEQUENCE: 29

```
tggaagggct aattcactcc caacgaagac aagatctgct tttgcttgt actgggtctc     60

tctggttaga ccagatctga gcctgggagc tctctggcta actagggaac ctactgctta    120

agcctcaata aagcttgcct tgagtgcttc aagtagtgtg tgcccgtctg ttgtgtgact    180

ctggtaacta gagatccctc agaccctttt agtcagtgtg gaaaatctct agc           233
```

<210> SEQ ID NO 30
<211> LENGTH: 140
<212> TYPE: DNA
<213> ORGANISM: Artificial
<220> FEATURE:
<223> OTHER INFORMATION: SV40 origin of replication

<400> SEQUENCE: 30

```
atcccgcccc taactccgcc cagttccgcc cattctccgc cccatggctg actaattttt     60

tttatttatg cagaggccga ggccgcctcg gcctctgagc tattccagaa gtagtgagga    120

ggcttttttg gaggcctagg                                                140
```

<210> SEQ ID NO 31
<211> LENGTH: 792
<212> TYPE: DNA
<213> ORGANISM: Artificial
<220> FEATURE:
<223> OTHER INFORMATION: Drug resistance gene

<400> SEQUENCE: 31

```
attgaacaag atggattgca cgcaggttct ccggccgctt gggtggagag gctattcggc     60

tatgactggg cacaacagac aatcggctgc tctgatgccg ccgtgttccg gctgtcagcg    120

caggggcgcc cggttctttt tgtcaagacc gacctgtccg gtgccctgaa tgaactgcaa    180

gacgaggcag cgcggctatc gtggctggcc acgacgggcg ttccttgcgc agctgtgctc    240

gacgttgtca ctgaagcggg aagggactgg ctgctattgg gcgaagtgcc ggggcaggat    300

ctcctgtcat ctcaccttgc tcctgccgag aaagtatcca tcatggctga tgcaatgcgg    360

cggctgcata cgcttgatcc ggctacctgc ccattcgacc accaagcgaa acatcgcatc    420

gagcgagcac gtactcggat ggaagccggt cttgtcgatc aggatgatct ggacgaagag    480

catcaggggc tcgcgccagc cgaactgttc gccaggctca aggcgagcat gcccgacggc    540

gaggatctcg tcgtgaccca tggcgatgcc tgcttgccga atatcatggt ggaaaatggc    600

cgcttttctg gattcatcga ctgtggccgg ctgggtgtgg cggaccgcta tcaggacata    660

gcgttggcta cccgtgatat tgctgaagag cttggcggcg aatgggctga ccgcttcctc    720

gtgctttacg gtatcgccgc tcccgattcg cagcgcatcg ccttctatcg ccttcttgac    780

gagttcttct ga                                                        792
```

<210> SEQ ID NO 32
<211> LENGTH: 620
<212> TYPE: DNA
<213> ORGANISM: Artificial
<220> FEATURE:
<223> OTHER INFORMATION: Drug resistance gene

<400> SEQUENCE: 32

```
agatcaaagg atcttcttga gatccttttt ttctgcgcgt aatctgctgc ttgcaaacaa     60

aaaaaccacc gctaccagcg gtggtttgtt tgccggatca agagctacca actctttttc    120

cgaaggtaac tggcttcagc agagcgcaga taccaaatac tgttcttcta gtgtagccgt    180
```

-continued

```
agttaggcca ccacttcaag aactctgtag caccgcctac atacctcgct ctgctaatcc    240

tgttaccagt ggctgctgcc agtggcgata agtcgtgtct taccgggttg gactcaagac    300

gatagttacc ggataaggcg cagcggtcgg gctgaacggg gggttcgtgc acacagccca    360

gcttggagcg aacgacctac accgaactga gatacctaca gcgtgagcta tgagaaagcg    420

ccacgcttcc cgaagggaga aaggcggaca ggtatccggt aagcggcagg gtcggaacag    480

gagagcgcac gagggagctt ccagggggaa acgcctggta tctttatagt cctgtcgggt    540

ttcgccacct ctgacttgag cgtcgatttt tgtgatgctc gtcagggggg cggagcctat    600

ggaaaaacgc cagcaacgcg                                                620
```